US010737113B2

(12) United States Patent
Papadopoulos et al.

(10) Patent No.: US 10,737,113 B2
(45) Date of Patent: Aug. 11, 2020

(54) HUMAN ANTIBODIES TO PD-1

(71) Applicant: Regeneron Pharmaceuticals, Inc., Tarrytown, NY (US)

(72) Inventors: Nicholas J. Papadopoulos, LaGrangeville, NY (US); Andrew J. Murphy, Croton-on-Hudson, NY (US); Gavin Thurston, Briarcliff Manor, NY (US); Ella Ioffe, Bronx, NY (US); Elena Burova, Mount Kisco, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 77 days.

(21) Appl. No.: 15/905,685

(22) Filed: Feb. 26, 2018

(65) Prior Publication Data

US 2018/0185668 A1 Jul. 5, 2018

Related U.S. Application Data

(63) Continuation of application No. 14/603,776, filed on Jan. 23, 2015, now Pat. No. 9,987,500.

(60) Provisional application No. 61/930,576, filed on Jan. 23, 2014, provisional application No. 62/014,181, filed on Jun. 19, 2014.

(51) Int. Cl.

| | |
|---|---|
| ***C07K 16/28*** | (2006.01) |
| ***C12N 15/13*** | (2006.01) |
| ***C12N 15/63*** | (2006.01) |
| ***A61K 39/395*** | (2006.01) |
| ***A61N 5/10*** | (2006.01) |
| ***A61K 45/06*** | (2006.01) |
| *A61K 39/00* | (2006.01) |

(52) U.S. Cl.

CPC ............ *A61N 5/10* (2013.01); *A61K 39/3955* (2013.01); *A61K 45/06* (2013.01); *C07K 16/2818* (2013.01); *C07K 16/2827* (2013.01); *A61K 2039/505* (2013.01); *A61K 2039/545* (2013.01); *C07K 2317/21* (2013.01); *C07K 2317/31* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 5,629,204 | A | 5/1997 | Honjo et al. |
| 5,698,520 | A | 12/1997 | Honjo et al. |
| 6,596,541 | B2 | 7/2003 | Murphy et al. |
| 6,803,792 | B2 | 10/2004 | Yasuda et al. |
| 6,808,710 | B1 | 10/2004 | Wood et al. |
| 6,936,704 | B1 | 8/2005 | Freeman et al. |
| 7,029,674 | B2 | 4/2006 | Carreno et al. |
| 7,038,013 | B2 | 5/2006 | Freeman et al. |
| 7,087,411 | B2 | 8/2006 | Daly et al. |
| 7,101,550 | B2 | 9/2006 | Wood et al. |
| 7,488,802 | B2 | 2/2009 | Collins et al. |
| 7,521,051 | B2 | 4/2009 | Collins et al. |
| 7,563,869 | B2 | 7/2009 | Honjo et al. |
| 7,595,048 | B2 | 9/2009 | Honjo et al. |
| 7,635,757 | B2 | 12/2009 | Freeman et al. |
| 7,638,492 | B2 | 12/2009 | Wood et al. |
| 7,709,214 | B2 | 5/2010 | Freeman et al. |
| 7,722,868 | B2 | 5/2010 | Freeman et al. |
| 7,794,710 | B2 | 9/2010 | Chen et al. |
| 7,943,742 | B2 | 5/2011 | Violette et al. |
| 7,943,743 | B2 | 5/2011 | Korman et al. |
| 7,998,479 | B2 | 8/2011 | Honjo et al. |
| 8,008,449 | B2 | 8/2011 | Korman et al. |
| 8,088,905 | B2 | 1/2012 | Collins et al. |
| 8,168,179 | B2 | 5/2012 | Honjo et al. |
| 8,168,757 | B2 | 5/2012 | Finnefrock et al. |

(Continued)

FOREIGN PATENT DOCUMENTS

| | | | |
|---|---|---|---|
| EP | 0 670 369 | A2 | 9/1995 |
| EP | 0670369 | A2 | 9/1995 |

(Continued)

OTHER PUBLICATIONS

Al-Lazikani, B. et al., "Standard Conformations for the Canonical Structures of Immunoglobulins," J. Mol. Biol., vol. 273, pp. 927-948 (1997).

Hofmeyer, K et al., "The PD-1/PD-L1 (B7-H1) Pathway in Chronic Infection-Induced Cytotoxic T Lymphocyte Exhaustion," Journal of Biomedicine and Biotechnology, vol. 2011, Article ID 451694, 9 pages, doi:10.1155/2011/451694 (Copyright 2011).

Kasagi, S. et al., "PD-1 and Autoimmunity," Critical Reviews™ in Immunology, vol. 31, No. 4, pp. 265-295 (2011).

(Continued)

*Primary Examiner* — Ilia I Ouspenski

(74) *Attorney, Agent, or Firm* — Fox Rothschild LLP; Aparna G. Patankar

(57) ABSTRACT

The present invention provides antibodies that bind to the T-cell co-inhibitor programmed death-1 (PD-1) protein, and methods of use. In various embodiments of the invention, the antibodies are fully human antibodies that bind to PD-1. In certain embodiments, the present invention provides multi-specific antigen-binding molecules comprising a first binding specificity that binds to PD-1 and a second binding specificity that binds to an autoimmune tissue antigen, another T-cell co-inhibitor, an Fc receptor, or a T-cell receptor. In some embodiments, the antibodies of the invention are useful for inhibiting or neutralizing PD-1 activity, thus providing a means of treating a disease or disorder such as cancer or a chronic viral infection. In other embodiments, the antibodies are useful for enhancing or stimulating PD-1 activity, thus providing a means of treating, for example, an autoimmune disease or disorder.

18 Claims, 4 Drawing Sheets

Specification includes a Sequence Listing.

(56) References Cited

U.S. PATENT DOCUMENTS

| | | | |
|---|---|---|---|
| 8,216,996 | B2 | 7/2012 | Minato et al. |
| 8,217,149 | B2 | 7/2012 | Irving et al. |
| 8,246,955 | B2 | 8/2012 | Honjo et al. |
| 8,246,995 | B2 | 8/2012 | Dai et al. |
| 8,257,740 | B1 | 9/2012 | Sung et al. |
| 8,287,856 | B2 | 10/2012 | Li et al. |
| 8,354,509 | B2 | 1/2013 | Carven et al. |
| 8,383,796 | B2 | 2/2013 | Korman et al. |
| 8,460,927 | B2 | 6/2013 | Chen |
| 8,552,154 | B2 | 10/2013 | Freeman et al. |
| 8,574,872 | B2 | 11/2013 | Minato et al. |
| 8,580,247 | B2 | 11/2013 | Li et al. |
| 8,617,546 | B2 | 12/2013 | Kang et al. |
| 8,709,416 | B2 | 4/2014 | Langermann et al. |
| 8,728,474 | B2 | 5/2014 | Honjo et al. |
| 8,741,295 | B2 | 6/2014 | Olive |
| 8,779,105 | B2 | 7/2014 | Korman et al. |
| 8,779,108 | B2 | 7/2014 | Queva et al. |
| 9,359,437 | B2 | 6/2016 | Davis et al. |
| 9,987,500 | B2 * | 6/2018 | Papadopoulos .... A61K 39/3955 |
| 2004/0101920 | A1 | 5/2004 | Radziejewski et al. |
| 2005/0226876 | A1 | 10/2005 | Graus et al. |
| 2005/0244403 | A1 | 11/2005 | Lazar et al. |
| 2007/0280945 | A1 | 12/2007 | Stevens et al. |
| 2009/0055944 | A1 | 2/2009 | Korman et al. |
| 2009/0217401 | A1 | 8/2009 | Korman et al. |
| 2009/0274666 | A1 | 11/2009 | Chen |
| 2009/0317368 | A1 | 12/2009 | Chen |
| 2010/0203056 | A1 | 8/2010 | Irving et al. |
| 2010/0331527 | A1 | 12/2010 | Davis et al. |
| 2011/0008369 | A1 | 1/2011 | Finnefrock et al. |
| 2011/0171215 | A1 | 7/2011 | Davis et al. |
| 2011/0171220 | A1 | 7/2011 | Davis |
| 2011/0177088 | A1 | 7/2011 | Olive et al. |
| 2011/0195454 | A1 | 8/2011 | McWhirter et al. |
| 2012/0027759 | A1 | 2/2012 | Chen et al. |
| 2012/0121634 | A1 | 5/2012 | Chen et al. |
| 2013/0017199 | A1 | 1/2013 | Langermann |
| 2013/0022595 | A1 | 1/2013 | Rotem-Yehudar et al. |
| 2013/0034559 | A1 | 2/2013 | Queva |
| 2013/0045200 | A1 | 2/2013 | Irving et al. |
| 2013/0045201 | A1 | 2/2013 | Irving et al. |
| 2013/0045202 | A1 | 2/2013 | Irving et al. |
| 2013/0095098 | A1 | 4/2013 | Tyson |
| 2013/0108651 | A1 | 5/2013 | Carven et al. |
| 2013/0109843 | A1 | 5/2013 | Carven et al. |
| 2013/0122014 | A1 | 5/2013 | Korman et al. |
| 2013/0164294 | A1 | 6/2013 | Honjo et al. |
| 2013/0291136 | A1 | 10/2013 | Freeman et al. |
| 2013/0303250 | A1 | 11/2013 | Moore |
| 2014/0088295 | A1 | 3/2014 | Smith et al. |
| 2014/0212422 | A1 | 7/2014 | Korman et al. |
| 2014/0243504 | A1 | 8/2014 | Davis et al. |
| 2014/0271684 | A1 | 9/2014 | Li et al. |
| 2014/0308299 | A1 | 10/2014 | Allison et al. |
| 2015/0166661 | A1 | 6/2015 | Chen et al. |
| 2015/0203579 | A1 | 7/2015 | Papadopoulos et al. |
| 2015/0203580 | A1 | 7/2015 | Papadopoulos et al. |
| 2015/0266966 | A1 | 9/2015 | Smith et al. |
| 2016/0311903 | A1 | 10/2016 | West et al. |
| 2017/0008951 | A1 | 1/2017 | Block et al. |
| 2017/0044259 | A1 | 2/2017 | Tipton et al. |
| 2017/0174779 | A1 | 6/2017 | Varghese et al. |
| 2019/0040137 | A1 * | 2/2019 | Hu ....................... A61K 9/0019 |

FOREIGN PATENT DOCUMENTS

| | | | |
|---|---|---|---|
| EP | 1591527 | A1 | 11/2005 |
| EP | 1 210 424 | B1 | 2/2007 |
| EP | 1210424 | B1 | 2/2007 |
| EP | 2 161 336 | A1 | 3/2010 |
| EP | 2161336 | A1 | 3/2010 |
| EP | 2 172 219 | A1 | 4/2010 |
| EP | 2172219 | A1 | 4/2010 |
| EP | 2 206 517 | A1 | 7/2010 |
| EP | 2206517 | A1 | 7/2010 |
| EP | 1 537 878 | B1 | 9/2010 |
| EP | 1537878 | B1 | 9/2010 |
| EP | 2262837 | A2 | 12/2010 |
| EP | 1 576 014 | B1 | 6/2011 |
| EP | 1576014 | B1 | 6/2011 |
| EP | 2 418 278 | A2 | 2/2012 |
| EP | 2418278 | A2 | 2/2012 |
| EP | 2 468 765 | A1 | 6/2012 |
| EP | 2468765 | A1 | 6/2012 |
| EP | 2504028 | A2 | 10/2012 |
| EP | 2 535 354 | A1 | 12/2012 |
| EP | 2535354 | A1 | 12/2012 |
| EP | 1 297 135 | B1 | 1/2013 |
| EP | 1297135 | B1 | 1/2013 |
| JP | 2006-340714 | A | 12/2006 |
| WO | 99/058572 | A1 | 11/1999 |
| WO | 01/39722 | A2 | 6/2001 |
| WO | 2001039722 | A2 | 6/2001 |
| WO | 02/078731 | A1 | 10/2002 |
| WO | 2002078731 | A1 | 10/2002 |
| WO | 03/042402 | A2 | 5/2003 |
| WO | 2003042402 | A2 | 5/2003 |
| WO | 2004/056875 | A1 | 7/2004 |
| WO | 2004056875 | A1 | 7/2004 |
| WO | 2005/103081 | A2 | 11/2005 |
| WO | 2005103081 | A2 | 11/2005 |
| WO | 2006/121168 | A1 | 11/2006 |
| WO | 2006121168 | A1 | 11/2006 |
| WO | 2007/002223 | A2 | 1/2007 |
| WO | 2007/005874 | A2 | 1/2007 |
| WO | 2007002223 | A2 | 1/2007 |
| WO | 2007005874 | A2 | 1/2007 |
| WO | 2007/093630 | A1 | 8/2007 |
| WO | 2009114335 | A2 | 9/2007 |
| WO | 2008/156712 | A1 | 12/2008 |
| WO | 2009/024531 | A1 | 2/2009 |
| WO | 2009024531 | A1 | 2/2009 |
| WO | 2009030285 | | 3/2009 |
| WO | 2009/101611 | A1 | 8/2009 |
| WO | 2009101611 | A1 | 8/2009 |
| WO | 2009/114335 | A2 | 9/2009 |
| WO | 2010/029434 | A1 | 3/2010 |
| WO | 2010/029435 | A1 | 3/2010 |
| WO | 2010027423 | A2 | 3/2010 |
| WO | 2010029434 | A1 | 3/2010 |
| WO | 2010029435 | A1 | 3/2010 |
| WO | 2010/036959 | A2 | 4/2010 |
| WO | 2010036959 | A2 | 4/2010 |
| WO | 2010/077634 | A1 | 7/2010 |
| WO | 2010077634 | A1 | 7/2010 |
| WO | 2010/089411 | A2 | 8/2010 |
| WO | 2011/066342 | A2 | 6/2011 |
| WO | 2011/066389 | A1 | 6/2011 |
| WO | 2011066342 | A2 | 6/2011 |
| WO | 2011066389 | A1 | 6/2011 |
| WO | 2011/110604 | A1 | 9/2011 |
| WO | 2011/110621 | A1 | 9/2011 |
| WO | 2011110604 | A1 | 9/2011 |
| WO | 2011159877 | | 12/2011 |
| WO | 2012/145493 | A1 | 10/2012 |
| WO | 2012145493 | A1 | 10/2012 |
| WO | 2013/014668 | A1 | 1/2013 |
| WO | 2013014668 | A1 | 1/2013 |
| WO | 2013/019906 | A1 | 2/2013 |
| WO | 2013019906 | A1 | 2/2013 |
| WO | 2013/079174 | A1 | 6/2013 |
| WO | 2013/079945 | A1 | 6/2013 |
| WO | 2013079174 | A1 | 6/2013 |
| WO | 2013079945 | A1 | 6/2013 |
| WO | 2013/166500 | A1 | 11/2013 |
| WO | 2013/169693 | A1 | 11/2013 |
| WO | 2013/173223 | A1 | 11/2013 |
| WO | 2013166500 | A1 | 11/2013 |
| WO | 2013169693 | A1 | 11/2013 |
| WO | 2013173223 | A1 | 11/2013 |
| WO | 2013/181452 | A1 | 12/2013 |
| WO | 2013181452 | A1 | 12/2013 |
| WO | 2014/055648 | A1 | 4/2014 |

(56) References Cited

FOREIGN PATENT DOCUMENTS

| | | | |
|---|---|---|---|
| WO | 2014055648 | A1 | 4/2014 |
| WO | 2014/066834 | A1 | 5/2014 |
| WO | 2014066834 | A1 | 5/2014 |
| WO | 2014/127917 | A1 | 8/2014 |
| WO | 2014127917 | A1 | 8/2014 |
| WO | 2014/151006 | A2 | 9/2014 |
| WO | 2014151006 | A2 | 9/2014 |
| WO | 2014/159562 | A1 | 10/2014 |
| WO | 2014159562 | A1 | 10/2014 |
| WO | 2014/179664 | A1 | 11/2014 |
| WO | 2014179664 | A2 | 11/2014 |
| WO | 2014/194293 | A1 | 12/2014 |
| WO | 2014/209804 | A1 | 12/2014 |
| WO | 2014194293 | A1 | 12/2014 |
| WO | 2014209804 | A1 | 12/2014 |
| WO | 2015/009856 | A2 | 1/2015 |
| WO | 2015009856 | A2 | 1/2015 |
| WO | 2015/016718 | A1 | 2/2015 |
| WO | 2015/026634 | A1 | 2/2015 |
| WO | 2015/026684 | A1 | 2/2015 |
| WO | 2015016718 | A1 | 2/2015 |
| WO | 2015026684 | A1 | 2/2015 |
| WO | 2015/042246 | A1 | 3/2015 |
| WO | 2015042246 | A1 | 3/2015 |
| WO | 2015/048312 | A1 | 4/2015 |
| WO | 2015048312 | A1 | 4/2015 |
| WO | 2015048520 | A1 | 4/2015 |
| WO | 2015/112800 | A1 | 7/2015 |
| WO | 2015/112900 | A1 | 7/2015 |
| WO | 2015112800 | A1 | 7/2015 |
| WO | 2015112900 | A1 | 7/2015 |
| WO | 2015/193352 | A1 | 12/2015 |
| WO | 2015/200119 | A1 | 12/2015 |
| WO | 2015193352 | A1 | 12/2015 |
| WO | 2015200119 | A1 | 12/2015 |
| WO | 2016061142 | A1 | 4/2016 |
| WO | 2008156712 | A1 | 8/2017 |

OTHER PUBLICATIONS

Peng, W., "PD-1 Blockade Enhances T-cell Migration to Tumors by Elevating IFN-γ Inducible Chemokines," Cancer Res., vol. 72, No. 20, pp. 5209-5218 (Published OnlineFirst Aug. 20, 2012).

Powles, T. et al., "MPDL3280A (anti-PD-L1) treatment leads to clinical activity in metastatic bladder cancer," Nature, vol. 515, pp. 558-562 (Nov. 27, 2014).

Raghuraman, S. et al., "Spontaneous Clearance of Chronic Hepatitis C Virus Infection is Associated with Appearance of Neutralizing Antibodies and Reversal of T-Cell Exhaustion," The Journal of Infectious Diseases, vol. 205, pp. 763-771 (Mar. 1, 2012).

Iwai, et al, Involvement of PD-L1 on Tumor Cells in the Escape from Host Immune System and Tumor Immunotherapy by PD-L1 Blockade, PNAS, 99(19):12293-12297 (Sep. 17, 2002).

Ohaegbulam, et al: "Human Cancer Immunotherapy with Antibodies to the PD-1 and PD-L1 Pathway," Trends in Molecular Medicine, 21(1):24-33 (Jan. 2015).

McDermott DF, et al. "PD-1 as a potential target in cancer therapy", Cancer Med., 2013, vol. 2, No. 5, pp. 662-673.

"Study of REGN2810 and REGN1979 in Patients with Lymphoma or Acute Lymphoblastic Leukemia," retrieved from the internet: https://api.liveclinicaltrials.com/trialpage?dcn=10963&city=Baltimore&country=UnitedStates&start=20&state=Maryland&conditions=lymphoma&id=207048402254, 1 page (last updated Nov. 16, 2016).

"A Phase 1 Study to Access Safety and Tolerability of REGN1979, an anti-CD20 x anti-CD3 bispecific monoclonal antibody, and REGN2810, an anti-programmed death-1 (PD-1) monoclonal antibody", EU Clinical Trials Register, https://www.clinicaltrialsregister.eu/ctr-search/search?query=2015-001697-17, 3 pages (Start Date: Dec. 1, 2015).

"Clinical Trials Register: A Phase 1 Study to Access Safety and Tolerability of REGN1979, an anti-CD20 x anti-CD3 bispecific monoclonal antibody, and REGN2810, an anti-programmed death-1 (PD-1) monoclonal antibody, in Patients with B-cell Malignancies", EU Clinical Trials Register, https://www.clinicaltrialsregister.eu/ctr-search/trial/2015-001697-17/ES, 8 pages (Oct. 15, 2015).

Mohiuddin et al., High-Dose Radiation as a Dramatic, Immunological Primer in Locally Advanced Melanoma, CUREUS (2015).

Ramesh Rengan et al., Radiation Therapy Contraindications and Safety Panel: Re-irradiation, Novel Combination Therapies, and Hypofractionation, https://www.astro.org/uploadedFiles/_MAIN_SITE_Meeting_and_Education/Events_(Astro)/2016/Sample_ASTRO_Meeting/Content_Pieces/RTPaneCombined.pdf: 31-32 (2016).

Anonymous, NCT02760498: A Ogase 2 Study of REGN2810, a Fully Human Monoclonal Antibody to Programmed Death-1 (PD-1), in Patients With Advanced Cutaneous Squamous Cell Carcinoma, ClinicalTrials.gov rchive, https://clinicaltrials.gov/archive/NCT02760498/2016_05_02(2016).

Wang et al., "Suppression of type I IFN signaling in tumors mediates resistance to anti-PD-1 treatment that can be overcome by radiotherapy", Cancer Res., 77(4):839-850 (2016).

Shields et al., "Lack of Fucose on Human IgG1 N-Linked Oligosaccharide Improves Binding to Human FcγRIII and Antibody-dependent Cellular Toxicity," J. Biol. Chem., 277(30):26733-26740 (Jul. 26, 2002).

Papadopoulos et al. "REGN2810, A Human Anti-PD-1 Monoclonal Antibody, for Patients with Unresectable Locally Advanced or Metastatic Cutaneous Squamous Cell Carcinoma (CSCC): Initial Safety and Efficacy," ASCO Annual Meeting (2017).

Anonymous, "Clinical Trails Register: A Phase I Study to Assess Safety and Tolerability of REGN1979, an anti-CD20 x anti-CD3 bispecific monoclonal antibody, and REGN2810, and anti-programmed death-1 (PD-1) monoclonal antibody, in Patients with B-cell Malignancies," p. 1, section A.3; p. 3, section E.1 [Retrieved from the Internet Mar. 14, 2017: <URL: https://www.clinicaltrailsregister.eu/ctr-search/trial/2015-001697-17/ES>].

J. R. Brahmer et al: "Phase I Study of Single-Agent Anti-Programmed Death-1 (MDX-1106) in Refractory Solid Tumors: Safety, Clinical Activity, Pharmacodynamics, and Immunologic Correlates", Journal of Clinical Oncology, vol. 28, No. 19, Jun. 1, 2010, pp. 3167-3175.

Extended European Search Report dated Feb. 11, 2019 in European Patent Application No. 18206830.4.

Nagasaka et al., "PD1/PD-L1 inhibition as a potential radiosensitizer in head and neck squamous cell carcinoma: a case report", Journal for Immuno Therapy of Cancer, (2016) 4:83, pp. 1-4.

Saâda-Bouzid et al., "Hyperprogression during anti-PD-1/PD-L1 therapy in patients with recurrent and/or metastatic head and neck squamous cell carcinoma", Annals of Oncology, Oct. 7, 2017, 28 (7): 1605-11.

D'Souza et al., "Combining Radiation Therapy with Immune Checkpoint Blockade for Central Nervous System Malignancies", Frontiers in Oncology, Oct. 7, 2016, 6: 212; pp. 1-8.

Park et al., "PD-1 Restrains Radiotherapy-Induced Abscopal Effect", Cancer Immunology Research, Jun. 2015, 3(6): 610-9.

Office Action dated Jan. 4, 2019 in Malaysian Patent Application No. PI 2016702408.

Reddy, M. et al., "Elimination of Fc Receptor-Dependent Effector Functions of a Modified IgG4 Monoclonal Antibody to Human CD4," J. Immunol, vol. 164, pp. 1925-1933 (2000).

Reineke, U., "Antibody Epitope Mapping Using Arrays of Synthetic Peptides," Methods in Molecular Biology, vol. 248: Antibody Engineering: Methods and Protocols, pp. 443-463 (2004).

Rennert, P., "Last Week's Immune Checkpoint Papers in Nature are Complicated!," SugarCone Biotech, htt://www.sugarconebotech.com/?p=814, pp. 1-4 (Dec. 4, 2014).

Ribas, A., "Tumor Immunotherapy Directed at PD-1," The New England Journal of Medicine, vol. 366, No. 26, pp. 2517-2519 (Jun. 28, 2012).

Riley, J., "PD-1 signaling in Primary T cells," Immunol. Rev., vol. 229, No. 1, pp. 114-125 (May 2009).

Schalper, K. et al., "In situ Tumor PD-L1 mRNA expression is associated with increased TILs and better outcome in breast carci-

(56) References Cited

OTHER PUBLICATIONS nomas," Clinical Cancer Research, Author Manuscript Published OnlineFirst on Mar. 19, 2014; DOI:10.1158/1078-0432.CCR-13/2702.
Sheridan, C., "Cautious optimism surrounds early clinical data for PD-1 blocker," Nature Biotechnology, vol. 30, No. 8, pp. 729-730 (Aug. 2012).
Shetty, R. et al., "PD-1 blockade during chronic SIV infection reduces hyperimmune activation and microbial translocation in rhesus macaques," The Journal of Clinical Investigation, vol. 122, No. 5, pp. 1712-1716 (May 2012).
Shields, R. et al., "Lack of Fucose on Human IgG1 N-Linked Oligosaccharide Improves Binding to Human FcγRIII and Antibody-dependent Cellular Toxicity," J. Biol. Chem., vol. 277, No. 30, pp. 23733-26740 (Jul. 26, 2002).
Sznol, M. et al., "Antagonist Antibodies to PD-1 and B7-H1 (PD-L1) in the Treatment of Advanced Human Cancer," Clinical Cancer Research, vol. 19, No. 5, pp. 1021-1034 (Mar. 1, 2013).
Topalian S., slides presented at MMS Annual Education Program May 9-11, 2013 in Boston MA.
International Search Report and Written Opinion dated Jul. 10, 2015, for corresponding International Patent Application Serial No. PCT/US2015/012589.
Tsai, K. et al., "PD-1 and PD-L1 Antibodies for Melonama", Human Vaccines & Immunotherapeutics (2014) 10: 3111-3116.
Momtaz et al., "Immunoligic Checkpooints in Cancer Therapy: Focus on the Programmed Death-I (PD-I) Receptor Pathway", Pharmacogenomics and Personalized Medicine (2014) 7: 357-365.
Ai-Lazikani, B. et al., "Standard Conformations for the Canonical Structures of Immunoglobulins," J. Mol. Biol., vol. 273, pp. 927-948 (1997).
Altschul, S. et al., "Basic Local Alignment Search Tool," J. Mol. Biol., vol. 215, pp. 403-410 (1990).
Altschul, S. et al., "Gapped BLAST and PSI-BLAST: a new generation of protein database search programs," Nucleic Acids Research, vol. 25, No. 17, pp. 3389-3402 (1997).
Arruebo, M. et al., "Antibody-Conjugated Nanoparticles for Biomedical Applications," Journal of Nanomaterials, vol. 2009, Article ID 439389, 24 pages, doi:10.1155/2009/439389.
Badoual, C. et al., "PD-1-Expressing Tumor-Infiltrating T Cells are a Favorable Prognostic Biomarker in HPV-Associated Head and Neck Cancer," Cancer Research, vol. 73, No. 1, pp. 128-138 (Jan. 1, 2013).
Brahmer, J. et al., "Safety and Activity of Anti-PD-L1 Antibody in Patients with Advanced Cancer," The New England Journal of Medicine, vol. 366, No. 26, pp. 2455-2465 (Jun. 28, 2012).
Brusa, D. et al., "The PD-1/PD-L1 axis contributes to T cell dysfunction in chronic lymphocytic leukemia," Haematologica 2012 [Epub ahead of print), 48 pages (2012).
Chattopadhyay, K., "Sequence, structure, function, immunity: structural genomics of costimulation," Immunol. Rev., vol. 229, No. 1, pp. 356-386 (May 2009).
Chen, D. et al., "Molecular Pathways: Next-Generation Immunotherapy—Inhibiting Programmed Death-Ligand 1 and Programmed Death-1," Clinical Cancer Research, vol. 18, No. 24, pp. 6580-6587 (Dec. 15, 2012).
Chen, L. et al., "Molecular mechanisms of T cell co-stimulation and co-inhibition," Nature Rev Immunol., vol. 13, pp. 227-242 (Apr. 2013).
Chen, L. et al., "Molecular mechanisms of T cell co-stimulation and co-inhibition," Nature Rev Immunol., vol. 13, pp. 227-242 (Apr. 2013) NIH Public Access Author Manuscript; available in PMC Apr. 1, 2014.
Dong, H. et al., "B7-H1, a third member of the B7 family, co-stimulates T-cell proliferation and interleukin-10 secretion," Nature Medicine, vol. 5, No. 12, pp. 1365-1369 (Dec. 1999).
Eggermont, A. et al., "Smart therapeutic strategies in immune-oncology," Nat. Rev. Clin. Oncol., Advance Online Publication, pp. 1-2 (Mar. 4, 2014).
Ehring, H., "Hydrogen Exchange/Electrospray Ionization Mass Spectrometry Studies of Structural Features of Proteins and Protein/Protein Interactions," Analytical Biochemistry, vol. 267, pp. 252-259 (1999).
Eisenhauer, E.A. et al., "New response evaluation criteria in solid tumours: Revised RECIST guideline (version 1.1)," European Journal of Cancer, vol. 45, pp. 228-247 (2009).
Engen, J. et al., "Investigating protein structure and dynamics by hydrogen exchange MS," Analytical Chemistry, vol. 73, No. 9, pp. 256A-265A (May 1, 2001).
Fife, B. et al., "The role of the PD-1 pathway in autoimmunity and peripheral tolerance," Ann. N.Y. Acad. Sci., vol. 1217, pp. 45-59 (2011).
Flies, D. et al., "Blockade of the B7-H1/PD-1 Pathway for Cancer Immunotherapy," Yale Journal of Biology and Medicine, vol. 84, pp. 409-421 (2011).
Francisco, L et al., "The PD-1 Pathway in Tolerance and Autoimmunity," Immunol. Rev. vol. 236, pp. 219-242 (Jul. 2010).
Freeman, G., "Structures of PD-1 with its ligands: Sideways and dancing cheek to cheek," PNAS, vol. 105, No. 30, pp. 10275-10276 (Jul. 29, 2008).
GenBank Accession No. NP_005009 Mar. 15, 2015.
GenBank Accession No. NP_005182 Mar. 15, 2015.
GenBank Accession No. NP_009192 Mar. 15, 2015.
GenBank Accession No. NP_054862 Sep. 25, 2015.
Gonnet, G. et al., "Exhaustive Matching of the Entire Protein Sequence Database," Science, vol. 256, pp. 1443-1445 (Jun. 5, 1992).
Hamid, O. et al., "Anti-programmed death-1 and anti-programmed death-ligand 1 antibodies in cancer therapy," Expert Opin. Biol. Ther. [Early Online], pp. 1-15 (Copyright 2013).
Herbst, R. et al., "Predictive correlates of response to the anti-PD-L1 antibody MPDL3280A in cancer patients," Nature, vol. 515, pp. 563-567 (Nov. 27, 2014).
Hochleitner, E. et al. "Characterization of a discontinuous epitope of the human immunodeficiency virus (HIV) core protein p24 by epitope excision and differential chemical modification followed by mass spectrometric peptide mapping analysis," Protein Science, vol. 9, pp. 487-496 (2000).
Hofmeyer, K. et al., "The PD-1/PD-L1 (B7-H1) Pathway in Chronic Infection-Induced Cytotoxic T Lymphocyte Exhaustion," Journal of Biomedicine and Biotechnology, vol. 2011, Article ID 451694, 9 pages, doi:10.1155/2011/451694 (Copyright 2011). cited byapplicant.
International Search Report and Written Opinion for Application No. PCT/US2015/012595 dated Apr. 14, 2015.
Junghans, R.P. et al., "Anti-Tac-H, a Humanized Antibody to the Interleukin 2 Receptor with New Features for Immunotherapy in Malignant and Immune Disorders," Cancer Research, vol. 50, pp. 1495-1502 (1990).
Kabat, "Sequences of Proteins of Immunological Interest," National Institutes of Health, vol. 1, Bethesda, Md. (1991).
Kasagi, S. et al., "PD-1 and Autoimmunity," Critical Reviews.TM. in Immunology, vol. 31, No. 4, pp. 265-295 (2011).
Kazane, S. et al., "Self-Assembled Antibody Multimers through Peptide Nucleic Acid Conjugation," J. Am. Chem. Soc., vol. 135, pp. 340-346 (2013) published Dec. 4, 2012.
Klein, C. et al., "Progress in overcoming the chain association issue in bispecific heterodimeric IgG antibodies," mAbs, vol. 4, No. 6, pp. 653-663 (Nov./Dec. 2012).
Kufer, P. et al., "A revival of bispecific antibodies," Trends in Biotechnology, vol. 22, No. 5, pp. 238-244 (May 2004).
Langer, R., "New Methods of Drug Delivery," Science, vol. 249, pp. 1527-1533 (Sep. 28, 1990).
Lin, D. et al., "The PD-1/PD-L1 complex resembles the antigen-binding Fv domains of antibodies and T cell receptors," PNAS, vol. 105, No. 8, pp. 3011-3016 (Feb. 26, 2008).
Lipson, E. et al., "Durable Cancer Regression Off-Treatment and Effective Reinduction Therapy with an Anti-PD-1 Antibody," Clinical Cancer Research, vol. 19, No. 2, pp. 462-468 (Jan. 15, 2013).
Martin, A. et al., "Modeling antibody hypervariable loops: A combined algorithm," Proc. Natl. Acad. Sci. USA, vol. 86, pp. 9268-9272 (Dec. 1989).

(56) References Cited

OTHER PUBLICATIONS

Nishino, M. et al., "Developing a Common Language for Tumor Response to Immunotherapy: Immune-Related Response Criteria Using Unidimensional Measurements," Clinical Cancer Research, vol. 19, No. 14, pp. 3936—(Jul. 15, 2013).

Padlan, E. et al., "Identification of specificity-determining residues in antibodies," FASEB J, vol. 9, pp. 133-139 (Jan. 1995).

Pardoll, D., "The blockade of immune checkpoints in cancer immunotherapy," Nature Reviews|Cancer, vol. 12, pp. 252-264 (Apr. 2012).

Pearson, W., "Chapter 26. Using the FASTA Program to Search Protein and DNA Sequence Databases," Methods in Molecular Biology, vol. 24: Computer Analysis of Sequence Data, Part 1, pp. 307-331 (1994).

Peggs, K. et al., "PD-1 blockade: promoting endogenous anti-tumor immunity," Expert Rev. Anticancer Ther., vol. 12, No. 10, pp. 1279-1282 (2012).

Peng, W., "PD-1 Blockade Enhances T-cell Migration to Tumors by Elevating IFN-.gamma. Inducible Chemokines," Cancer Res., vol. 72, No. 20, pp. 5209-5218 (Published OnlineFirst Aug. 20, 2012).

Postow, M. et al., "Targeting Immune Checkpoints: Releasing the Restraints on Anti-tumor Immunity for Patients with Melanoma," Cancer J., vol. 18, No. 2, pp. 153-159 (2012).

Powell, M. et al., "Compendium of Excipients for Parenteral Formulations" PDA Journal of Pharmaceutical & Technology, vol. 52, No. 5, pp. 238-311 (Sep.-Oct. 1998).

Powles et al., "MPDL3280A (anti-PD-L1) treatment leads to clinical activity in metastatic bladder cancer," Nature, vol. 515, pp. 558-562 (Nov. 27, 2014).

Raghuraman et al., "Spontaneous Clearance of Chronic Hepatitis C Virus Infection is Associated with Appearance of Neutralizing Antibodies and Reversal of T-Cell Exhaustion," The Journal of Infectious Diseases, vol. 205, pp. 763-771 (Mar. 1, 2012).

Da Silva, "Anti-PD-1 monoclonal antibody Cancer immunotheraphy"; Drugs of the future; 39(1):15-24 (Jan. 1, 2014).

International Search Report and Written Opinion dated Jul. 10, 2015, for PCT/US2015/012589.

Keir et al., "Programmed Death-1 (PD-1): PD-Ligand 1 Interactions Inhibit TCR-Mediated Positive Selection of Thymocytes"; The Journal of Immunology; 175(11):7372-7379 (Dec. 1, 2005).

Riella et al., "Role of the PD-1 Pathway in the Immune Response"; American Journal of Transplantation, 12 (10):2575-2587 (Oct. 2012).

Zoran et al., "Programmed death 1 (PD-1) lymphocytes and ligand (PD-L1) in colorectal cancer and their relationship to microsatellite instability status"; J Clin Oncol; 32(5s)(abstr 3625), 2 pgs (May 30, 2014), downloaded from the web on Feb. 7, 2015 http://meetinglibrary.asco.org/content/133958-144.

Reddy et al., "Elimination of Fc Receptor-Dependent Effector Functions of a Modified IgG4 Monoclonal Antibody to Human CD4," J. Immunol, vol. 164, pp. 1925-1933 (2000).

Reineke, "Antibody Epitope Mapping Using Arrays of Synthetic Peptides," Methods in Molecular Biology, vol. 248: Antibody Engineering: Methods and Protocols, pp. 443-463 (2004).

Rennert, "Last Week's Immune Checkpoint Papers in Nature are Complicated!," SugarCone Biotech, htt://www.sugarconebotech.com/?p=814, pp. 1-4 (Dec. 4, 2014).

Ribas, "Tumor Immunotherapy Directed at PD-1," The New England Journal of Medicine, vol. 366, No. 26, pp. 2517-2519 (Jun. 28, 2012).

Riley, "PD-1 signaling in Primary T cells," Immunol. Rev., 229(1):114-125 (May 2009).

Schalper et al., "In situ Tumor PD-L1 mRNA expression is associated with increased TILs and better outcome in breast carcinomas," Clinical Cancer Research, Mar. 19, 2014.

Sheridan, "Cautious optimism surrounds early clinical data for PD-1 blocker," Nature Biotechnology, 30(8):729-730 (Aug. 2012).

Shetty et al., "PD-1 blockade during chronic SIV infection reduces hyperimmune activation and microbial translocation in rhesus macaques," The Journal of Clinical Investigation, 122(5):1712-1716 (May 2012).

Shields et al., "Lack of Fucose on Human IgG1 N-Linked Oligosaccharide Improves Binding to Human Fc.gamma. RIII and Antibody-dependent Cellular Toxicity," J. Biol. Chem., 277(30):23733-26740 (Jul. 26, 2002).

Sznol et al., "Antagonist Antibodies to PD-1 and B7-H1 (PD-L1) in the Treatment of Advanced Human Cancer," Clinical Cancer Research, 19(5): 1021-1034 (Mar. 1, 2013).

Topalian S., "Targeted Immunotherapy: Unleashing the Immune System Against Cancer", slides presented at MMS Annual Education Program May 9-11, 2013 in Boston MA.

Topalian, S. et al., "Targeting the PD-1/B7-H1(PD-L1) pathway to activate anti-tumor immunity," Current Opinion in Immunology, vol. 24, pp. 207-212 (2012).

Tumeh, P. et al. "PD-1 blockade induces responses by inhibiting adaptive immune resistance," Nature, vol. 515, pp. 568-571 (Nov. 27, 2014).

Tutt, A. et al., "Trispecific F(ab')3 derivatives that use cooperative signaling via the TCR/CD3 complex and CD2 to activate and redirect resting cytotoxic T cells," J. Immunol, vol. 147, No. 1, pp. 60-69 (Jul. 1, 1991).

Vajdos, F. et al., "Comprehensive Functional Maps of the Antigen-binding Site of an Anti-ErbB2 Antibody Obtained with Shotgun Scanning Mutagenesis," J. Mol. Biol., vol. 320, pp. 415-428 (2002).

Wang, X.F. et al., "PD-1/PDL1 and CD28/CD80 pathways modulate natural killer T cell function to inhibit hepatitis B virus replication," Journal of Viral Hepatitis, vol. 20 (Suppl. 1), p. 27-39 (2013).

Watanabe, N. et al., "Coinhibitory Molecules in Autoimmune Diseases," Clinical and Developmental Immunology, vol. 2012, Article ID 269756, 7 pages, doi:10.1155/2012/269756.

Weber, J., "Immune Checkpoint Proteins: A New Therapeutic Paradigm for Cancer—Preclinical Background: CTLA-4 and PD-1 Blockade," Semin Oncol, vol. 37, pp. 430-439 (2010).

Wu, G. et al., "Receptor-mediated in Vitro Gene Transformation by a Soluble DNA Carrier System," J. Biol. Chem., vol. 262, No. 10, pp. 4429-4432 (Apr. 5, 1987).

Zeng' J. et al., "Anti-PD-1 Blockade and Stereotactic Radiation Produce Long-Term Survival in Mice with Intracranial Gliomas," International Journal of Radiation Oncology, vol. 86, No. 2, pp. 1-7 (2013).

Zielinski, C. et al., "Rationale for targeting the immune system through checkpoint molecule blockade in the treatment of non-small-cell lung cancer," Annals of Oncology, vol. 24, No. 5, pp. 1170-1179 (May 2013).

Zou, W. et al., "Inhibitory B7-family molecules in the tumour microenvironment," Nature Reviews|Immunology, vol. 8, pp. 467-477 (Jun. 2008).

International Search Report and Written Opinion for PCT/US2016/068030 (dated May 26, 2017).

"Study of REGN2810 and REGN1979 in Patients with Lymphoma or Acute Lymphoblastic Leukemia", retrieved from the internet: https://api.liveclinicaltrials.com/trialpage?dcn=109638,city=Baltimore&country=UnitedStates&start=20&state=Maryland&conditions=lymphoma&id=207048402254, 1 page (last updated Nov. 16, 2016).

"A Phase 1 Study to Access Safety and Tolerability of REGN1979, an anti-CD20 x anti-CD3 bispecific monoclonal antibody, and REGN2810, an anti-programmed death-1 (PD-1) monoclonal antibody", EU Clinical Trials Register, <https://www.clinicaltrialsregister.eu/ctr-search/search?query=2015-001697-17,> 3 pages (Start Date: Dec. 1, 2015).

"Clinical Trials Register: A Phase 1 Study to Access Safety and Tolerability of REGN1979, an anti-CD20 x anti-CD3 bispecific monoclonal antibody, and REGN2810, an anti-programmed death-1 (PD-1) monoclonal antibody, in Patients with B-cellMalignancies", EU Clinical Trials Register, https://www.clinicaltrialsregister.eu/ctr-search/tria1/2015-001-697-17/ES, 8 pages (Oct. 15, 2015).

(56) References Cited

OTHER PUBLICATIONS

"Study of REGN2810 and REGN1979 in Patients with Lymphoma or Acute Lymphoblastic Leukemia", Smart Patients, <https://www.smartpatients.com/trials/NCT02651662,> 3 pages (Start Date: Nov. 2015).
Feuchtinger et al., "Leukemia Related Co-Stimulation/Co-Inhibition Predict T-Cell Attack of Acute Lymphoblastic Leukemia Mediated by Blinatumomab," Blood, 126:3764 (2015) (Abstract).
Opposition for Colombian Patent Application No. NC2016/0000106 (dated May 5, 2017).
Topalian et al., "Safety, activity, and immune correlates of anti-PD-1 antibody in cancer", The New England Journal of medicine: 366, 26: 2443-2454 (2012).
Anonymous, Safety, activity, and immune correlates of anti-PD-1 antibody in cancer, <https://clinicaltrials.gov/archive/>NCT02383212/2016_05_02 (2016).
Ahmed et al., "Clinical outcomes of melanoma brain metastases treated with stereotactic radiation and anti-PD-1 therapy", Annals of Oncology 27, 3: 434-441 (2015).
Mohiuddin et al., "High-Dose Radiation as a Dramatic, Immunological Primer in Locally Advanced Melanoma", Cureus (Dec. 18, 2015) 7(12): e417, DOI: 10.7759/cureus.417.
Park et al., "PD-1 Restrains Radiotherapy-Induced Abscopal Effect", Cancer Immunology Research, 3, 6: 610-619 (2015).
Liniker et al., "Safety and Activity of Combined Radiation Therapy (RT) and Anti-PD-1 Antibodies (PD-1) in Patients (pts) With Metastatic Melanoma", International Journal of Radiation: Oncology Biology Phsics, 93, 3: E635 (2015).
Ramesh Rengan et al., "Radiation Therapy Contraindications and Safety Panel: Re-irradiation, Novel Combination Therapies, and Hypofractionation", https://www.astro.org/uploadedFilest_MAIN_SITE_Meeting_and_Education/Events_(ASTRO)/2016/Sample_ASTRO_Meeting/Content_Pieces/RTPaneCombined.pdf: 31-32 (2016).
International Search Report for PCT/US2017/032397, dated Jul. 11, 2017.
International Search Report for PCT/US2017/032408, dated Jul. 6, 2017.
Anonymous, NCT02760498: "A Phase 2 Study of REGN2810, a Fully Human Monoclonal Antibody to Programmed Death-1 (PD-1), in Patients With Advanced Cutaneous Squamous Cell Carcinoma", ClinicalTrials.gov rchive,https://clinicaltrials.gov/archive/NCT02760498/2016_05_02(2016).
Mahoney et al, "The Next Immune-Checkpoint Inhibitors: PD-1/PD-L1 Blockade in Melanoma, Clinical Therapeutics", 37, 4: 764-782 (2015).
ESMO 2014: "Results of a Phase III Randomised Study of Nivolumab in Patients with Advanced Melanoma After Prior Anti-CTLA4 Therapy", European Society for Medical Oncology (2014).
U.S. Appl. No. 15/593,897, filed May 12, 2017.
U.S. Appl. No. 15/593,915, filed May 12, 2017.
DeMaria et al., "Ionizing Radiation Inhibition of Distant Untreated Tumors (Abscopal Effect) is Immune Mediated," Int. J. Radiation Oncology Biol. Phys., 58(3):862-870 (2004).
DeMaria et al., "Immune-Mediated Inhibition of Metastases after Treatment with Local Radiation and CTLA-4 Blockade in a Mouse Model of Breast Cancer," Clinical Cancer Research, 11:728-734 (2005).
Lugade et al., "Local Radiation Therapy of B16 Melanoma Tumors Increases the Generation of Tumor Antigen-Specific Effector Cells That Traffic to the Tumor," J. Immunol, 174:7516-7523 (2005).
Dewan et al., "Fractionated but Not Single-Dose Radiotherapy Induces an Immune-Mediated Abscopal Effect when Combined with Anti-CTLA-4 Antibody," Clin. Cancer Res., 15(17):5379-5388 (2009).
Kachikwu et al., "Radiation Enhances Regulatory T Cell Representation," Int. J. Radiation Oncology Biol. Phys., 81 (4):1128-1135 (2011).
Postow et al., "Immunologic Correlates of the Abscopal Effect in a Patient with Melanoma," The New England Journal of Medicine, 366:925-931 (2012).
Kalbasi, "Radiation and immunotherapy: a synergistic combination," The Journal of Clinical Investigation, 123 (7): 2756-2763 (2013).
Deng et al., "Irradiation and anti-PD-L1 treatment synergistically promote antitumor immunity in mice," The Journal of Clinical Investigation, 124(2):687-695 (2014).
Sharabi et al., "Stereotactic Radiation Therapy Augments Antigen-Specific PD-1 Mediated Anti-Tumor Immune Responses via Cross-Presentation of Tumor Antigen," Cancer Immunol Res, 3:345-355 (2014).
Crittenden et al., "Current Clinical Trials Testing Combinations of Immunotherapy and Radiation," Seminars in Radiation Oncology, 25:54-64 (2015).
Park et al., "PD-1 Restrains Radiotherapy-Induced Abscopal Effect", Cancer Immunol Res, 3(6):610-619 (2015).
Victor et al., "Radiation and dual checkpoint blockade activate non-redundant immune mechanisms in cancer," Nature, 520(7547):373-377 (2015).
Golden et al., "Local radiotherapy and granulocyte-macrophage colony-stimulating factor to generate abscopal responses in patients with metastatic solid tumours: a proof-of-principle trial", Lancet Oncol., 16:795-803 (2015).
Schoenhals et al., "Preclinical Rationale and Clinical Considerations for Radiotherapy Plus Immunotherapy: Going Beyond Local Control", The Cancer Journal, 22:130-137 (2016).
Bernstein et al., "Immunotherapy and stereotactic ablative radiotherapy (ISABR): a curative approach?", Nature Reviews, Clinical Oncology, 3:516-524 (2016).
Rodriguez-Ruiz et al., "Abscopal Effects of Radiotherapy Are Enhanced by Combined Immunostimulatory mAbs and Are Dependent on CD8 T Cells and Crosspriming", Cancer Res., 76:5994-6005 (2016).
Wang et al., "Suppression of type I IFN signaling in tumors mediates resistance to anti-PD-1 treatment that can be overcorne by radiotherapy", Cancer Res., 77(4):839-850 (2016).
Vanpouille-Box, "Towards precision radiotherapy for use with immune checkpoint blockers", Clin. Cancer Res., clincanres.0037.2017 (2017).
Weichselbaum et al., "Radiotherapy and immunotherapy: a beneficial liaison?", Nat Rev Clin Oncol, 14(6):365-379 (2017).
Pearson, "Flexible Sequence Similarity Searching with the FASTA3 Program Package," Methods Mol Biol, 132:185-219 (2000).
Shields et al., "Lack of Fucose on Human IgG1 N-Linked Oligosaccharide Improves Binding to Human FcyRIII and Antibody-dependent Cellular Toxicity," J. Biol. Chem., 277(30):26733-26740 (Jul. 26, 2002).
Borradori et al., "Rescue therapy with anti-programmed cell death protein 1 inhibitors (PD-1) of advanced cutaneous squamous cell carcinoma and basosquamous carcinoma: preliminary experience in 5 cases," Br J Dermatol., 175(6):1382-1386 (2016).
Chang et al., "A Case Report of Unresectable Cutaneous Squamous Cell Carcinoma Responsive to Pembrolizumab, a Programmed Cell Death Protein 1 Inhibitor," JAMA Dermatology, Letters: E1-E3 (2015).
Crammer et al., "Treatment of Unresectable and Metastatic Cutaneous Squamous Cell Carcinoma," The Oncologist 15:1320-1328 (2010).
Degache et al., "Major response to pembrolizumab in two patients with locally advanced cutaneous squamous cell carcinoma," JEADV, Letter to the Editor: 1-2 (2017).
Falchook et al., "Responses of metastatic basal cell and cutaneous squamous cell carcinomas to anti-PD1 monoclonal antibody REGN2810," J Immunother Cancer, 4(70):1-5 (2016).
Papadopoulos et al. "REGN2810, a Human Anti-PD-1 Monoclonal Antibody, for Patients with Unresectable Locally Advanced or Metastatic Cutaneous Squamous Cell Carcinoma (CSCC): Initial Safety and Efficacy," ASCO Annual Meeting (2017). cited byapplicant.
Fisher et al., "Suppressor T Lymphocytes Control the Development of Primary Skin Cancers in Ultraviolet-Irradiated Mice," Science, 216(4)1133-1134 (1982).
Freeman et al., "Comparative Immune Phenotypic Analysis of Cutaneous Squamous Cell Carcinoma and Intraepidermal Carci-

(56) References Cited

OTHER PUBLICATIONS noma in Immune-Competent Individuals: Proportional Representation of CD8+ T-Cells but Not FoxP3+ Regulatory T-Cells Is Associated with Disease Stage," PLOS ONE 9(10), e110928:1-9 (2014).
Mavropoulos et al., "Prospects for personalized targeted therapies for cutaneous squamous cell carcinoma," Seminars in Cutaneous Medicine and Surgery, 33:72-75 (2014).
Muhleisen et al., "Progression of cutaneous squamous cell carcinoma in immunosuppressed patients is associated with reduced CD123+ and FOXP3+ cells in the perineoplastic inflammatory infiltrate," Histopathology, 55:67-76 (2009).
Pickering et al., "Mutational landscape of aggressive cutaneous squamous cell carcinoma," Clin Cancer Res., 20 (24):6582-6592 (2014).
Schaper et al., "The Pattern and Clinicopathological Correlates of PD-L1 Expression in Cutaneous Squamous Cell Carcinoma," Running head: PD-L1 expression in cutaneous squamous cell carcinoma, Research Letter (2016).
Slater et al., "PD-L1 expression in cutaneous squamous cell carcinoma correlates with risk of metastasis," Knoxville Dermatopathology Laboratory, J Cutan Path, 43(8):663-70 (2016).
Soura et al., "Programmed cell death protein-1 inhibitors for immunotherapy of advanced nonmelanoma skin cancer: showing early promise," British Journal of Dermatology 175(6):1150-1151 (2016).
Stevenson et al., "Expression of Programmed Cell Death Ligand in Cutaneous Squamous Cell Carcinoma and Treatment of Locally Advanced Disease With Pembrolizumab," JAMA Dermatol., 153(4):299-303 (2017).
Tran et al., "Follow-up on Programmed Cell Death 1 Inhibitor for Cutaneous Squamous Cell Carcinoma," JAMA Dermatology, Letters: E1-E3 (2016).
Anonymous, "Clinical Trails Register: A Phase 1 Study to Assess Safety and Tolerability of REGN1979, an anti-CD20 x anti-CD3 bispecific monoclonal antibody, and REGN2810, and anti-programmed death-1 (PD-1) monoclonal antibody, in Patients withB-cell Malignancies," p. 1, section A.3; p. 3, section E.1 [Retrieved from the Internet Mar. 14, 2017: <URL: https://www.clinicaltrailsregister.eu/ctr-search/trial/2015-001697-17/ES&-gt;].
Anonymous, "Study of REGN2810 and REGN1979 in Patientcs with Lymphoma or Acute Lymphoblastic Leukemia." [Retrieved from the Internet Mar. 15, 2017: <URL: https://www.api.liveclinicaltrials.com/trialpage?dcn=10963&city=Baltimore-&country=UnitedStates&start=20&state=Maryland&conditions=lymphoma&id=20704-8402254>].
Office Action for Chilean Patent Application No. 1871-2016 (dated Feb. 5, 2018).
Keir, et al: "Programmed Death-1 (PD-1):L PD-Ligand 1 Interaction Inhibit TCR-Mediated Positive Selection of Thymocytes", Journal Immunology, 2005, vol. 175, No. 11, pp. 7372-7379.
Hu, et al. "The Abscopal Effect of Radiation Therapy: What Is It and How Can We Use It in Breast Cancer?" Current Breast Cancer Rep., 2017: 9 (1): 45-51.
Reynders, "The Abscopal Effect of Local Radiotherapy: Using Immunotherapy to Make a Rare Event Clinically Relevant" Cancer Treatment Review, Jun. 2015, 41 (6): 503-510.
Chuang et al., "Regression of a Metastic Lung Mass After Receiving Whole Brain Irradiation: Can the Abscopal Effect Cross the Blood-Brain Barrier?" Asian Pac J Cin Oncol., Oct. 14, 2018, (5): e-548-e550).
Brahmer et al., "Phase I Study of Single-Agent Anti-Programmed Death-1 (MDX-1106) in Refractory Solid Tumors: Safety, Clinical Activity, Pharmacodynamics, and Immunologic Correlates" J of Clin Oncol, 2010, 28(9): 3167-3175.
Da Silva, "Anti-PD-1 Monoclonal Antibody Cancer Immunotherapy" Drugs of the Future, 2014, 39(1): 15-24.

* cited by examiner

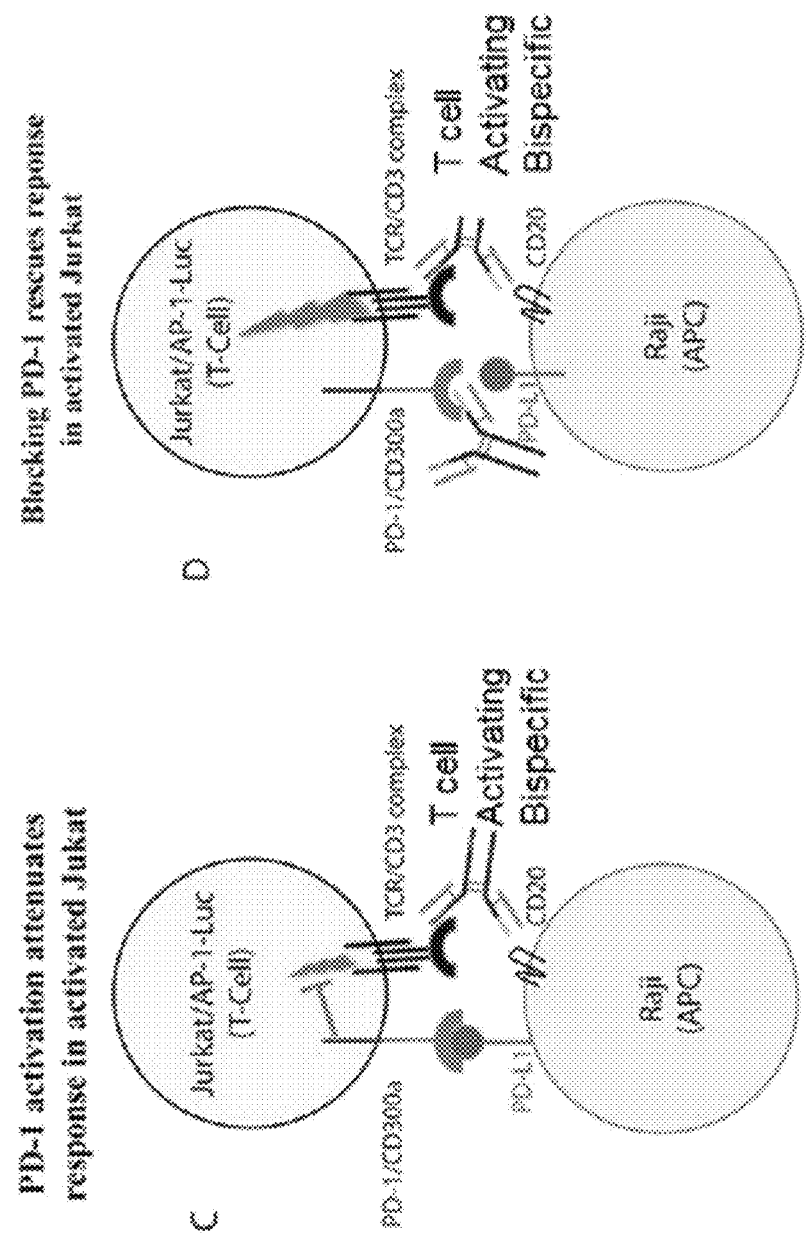
Figure 1 (Contd.)

SEQUENCE LISTING

<160> NUMBER OF SEQ ID NOS: 337

<210> SEQ ID NO 1
<211> LENGTH: 363
<212> TYPE: DNA
<213> ORGANISM: Artificial Sequence
<220> FEATURE:
<223> OTHER INFORMATION: Synthetic

<400> SEQUENCE: 1
gaggtgcagc tgttggagtc tgggggaggc ttggtacagc ctggggggtc cctgagactc 60
tcctgttcag cctctggatt cacctttagc agctatacca tgaactgggt ccgccaggct 120
ccagggaagg ggctggagtg ggtctcaggt attagtgata ccggtggtaa cacatactac 180
acagactccg tgaagggccg gttcaccgtc tccagagaca attccaagaa cacactgtct 240
ctgcaaatga acagcctgag agccgaggac acggccgtat attactgtgc gaaagatcag 300
ggtggaagtt acccctatta ctttcactac tggggccagg gatccctggt caccgtctcc 360
tca 363

<210> SEQ ID NO 2
<211> LENGTH: 121
<212> TYPE: PRT
<213> ORGANISM: Artificial Sequence
<220> FEATURE:
<223> OTHER INFORMATION: Synthetic

<400> SEQUENCE: 2

Glu Val Gln Leu Leu Glu Ser Gly Gly Gly Leu Val Gln Pro Gly Gly
1 5 10 15

Ser Leu Arg Leu Ser Cys Ser Ala Ser Gly Phe Thr Phe Ser Ser Tyr
20 25 30

Thr Met Asn Trp Val Arg Gln Ala Pro Gly Lys Gly Leu Glu Trp Val
35 40 45

Ser Gly Ile Ser Asp Thr Gly Gly Asn Thr Tyr Tyr Thr Asp Ser Val
50 55 60

Lys Gly Arg Phe Thr Val Ser Arg Asp Asn Ser Lys Asn Thr Leu Ser
65 70 75 80

Leu Gln Met Asn Ser Leu Arg Ala Glu Asp Thr Ala Val Tyr Tyr Cys
85 90 95

Ala Lys Asp Gln Gly Gly Ser Tyr Pro Tyr Tyr Phe His Tyr Trp Gly
100 105 110

Gln Gly Ser Leu Val Thr Val Ser Ser
115 120

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcacct ttagcagcta tacc 24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Ser Ser Tyr Thr
1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
attagtgata ccggtggtaa caca 24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Ser Asp Thr Gly Gly Asn Thr
1               5

<210> SEQ ID NO 7
<211> LENGTH: 42
<212> TYPE: DNA
<213> ORGANISM: Artificial Sequence
<220> FEATURE:
<223> OTHER INFORMATION: Synthetic

<400> SEQUENCE: 7
gcgaaagatc agggtggaag ttacccctat tactttcact ac 42

<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

Ala Lys Asp Gln Gly Gly Ser Tyr Pro Tyr Tyr Phe His Tyr
1               5                   10

<210> SEQ ID NO 9
<211> LENGTH: 324
<212> TYPE: DNA
<213> ORGANISM: Artificial Sequence
<220> FEATURE:
<223> OTHER INFORMATION: Synthetic

<400> SEQUENCE: 9
gacatccaga tgacccagtc tccatcctcc ctgtctgcat ctgtaggaga cagagtcacc 60
atcacttgcc gggcaagtca gagcattagc agctatttaa tttggtatca gcagaaacca 120
gggacagccc ctaagttcct gatctatgct gcatccagtt tgcaaagtgg ggtcccatca 180
aggttcagtg gctgtggatc tgggacagat ttcactctca ccatcagcag tctgcaacct 240
gaagattttg caacttacta ctgtcaacag agttacagta cccctccgat caccttcggc 300
caagggacac gactggagat taaa 324

<210> SEQ ID NO 10
<211> LENGTH: 108
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ile Trp Tyr Gln Gln Lys Pro Gly Thr Ala Pro Lys Phe Leu Ile
        35                  40                  45

Tyr Ala Ala Ser Ser Leu Gln Ser Gly Val Pro Ser Arg Phe Ser Gly
    50                  55                  60

Cys Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagagcatta gcagctat 18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Ser Ile Ser Ser Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gctgcatcc 9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Ala Ala Ser
1

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
caacagagtt acagtacccc tccgatcacc 30

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Gln Gln Ser Tyr Ser Thr Pro Pro Ile Thr
1 5 10

<210> SEQ ID NO 17
<211> LENGTH: 366
<212> TYPE: DNA
<213> ORGANISM: Artificial Sequence
<220> FEATURE:
<223> OTHER INFORMATION: Synthetic

<400> SEQUENCE: 17
gaggtgcagc tggtggagtc tggaggaggc ttggtccagc ctggggggtc cctgagactc 60
tcctgtgcag cctctgggtt caccgtcagt aacaactaca tgagctgggt ccgccaggct 120
ccagggaagg ggctggagtg ggtctcagtt atttatagcg gtggtttcac atactacaca 180
gactccgtga agggccgatt caccatctcc agacacaatt ccaagaacac gctgtatctt 240
caaatgaaca gcctgagagc tgaggacacg gccgtgtatt actgtgcgag gtattactat 300
gatactagtg attattggac cttctttgac tactggggcc agggaaccct ggtcaccgtc 360
tcctca 366

<210> SEQ ID NO 18
<211> LENGTH: 122
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Val Ser Asn Asn
20 25 30

Tyr Met Ser Trp Val Arg Gln Ala Pro Gly Lys Gly Leu Glu Trp Val
35 40 45

Ser Val Ile Tyr Ser Gly Gly Phe Thr Tyr Tyr Thr Asp Ser Val Lys
50 55 60

Gly Arg Phe Thr Ile Ser Arg His Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Tyr Tyr Tyr Asp Thr Ser Asp Tyr Trp Thr Phe Phe Asp Tyr Trp

```
            100                 105                 110

Gly Gln Gly Thr Leu Val Thr Val Ser Ser
        115                 120


<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19

gggttcaccg tcagtaacaa ctac                                          24


<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Phe Thr Val Ser Asn Asn Tyr
1               5


<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21

atttatagcg gtggtttcac a                                             21


<210> SEQ ID NO 22
<211> LENGTH: 7
<212> TYPE: PRT
<213> ORGANISM: Artificial Sequence
<220> FEATURE:
<223> OTHER INFORMATION: Synthetic

<400> SEQUENCE: 22

Ile Tyr Ser Gly Gly Phe Thr
1               5


<210> SEQ ID NO 23
<211> LENGTH: 48
<212> TYPE: DNA
<213> ORGANISM: Artificial Sequence
<220> FEATURE:
<223> OTHER INFORMATION: Synthetic

<400> SEQUENCE: 23

gcgaggtatt actatgatac tagtgattat tggaccttct ttgactac                48


<210> SEQ ID NO 24
<211> LENGTH: 16
<212> TYPE: PRT
<213> ORGANISM: Artificial Sequence
<220> FEATURE:
<223> OTHER INFORMATION: Synthetic

<400> SEQUENCE: 24

Ala Arg Tyr Tyr Tyr Asp Thr Ser Asp Tyr Trp Thr Phe Phe Asp Tyr
1               5                   10                  15
```

<210> SEQ ID NO 25
<211> LENGTH: 321
<212> TYPE: DNA
<213> ORGANISM: Artificial Sequence
<220> FEATURE:
<223> OTHER INFORMATION: Synthetic

<400> SEQUENCE: 25

```
gaaatagtga tgacgcagtc tccagccacc ctgtctgtgt ctccagggga aagagccacc     60

ctctcctgca gggccagtca gagtgttagc agcaacttag cctggtacca gcagaaacct    120

ggccaggctc ccaggctcct catctatggt gcatccacca gggccactgg tatcccagcc    180

aggttcagtg gcagtgggtc tgggacagag ttcactctca ccatcagtag cctgcagtct    240

ggagattttg cagtttatta ctgtcagcag tataataact ggccgctcac tttcggcgga    300

gggaccaagg tggagatcaa t                                              321
```

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Gly Asp Phe Ala Val Tyr Tyr Cys Gln Gln Tyr Asn Asn Trp Pro Leu
                85                  90                  95

Thr Phe Gly Gly Gly Thr Lys Val Glu Ile Asn
            100                 105
```

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27

```
cagagtgtta gcagcaac                                                   18
```

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

```
Gln Ser Val Ser Ser Asn
1               5
```

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 ggtgcatcc 9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Gly Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
cagcagtata ataactggcc gctcact 27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Gln Gln Tyr Asn Asn Trp Pro Leu Thr
1 5

<210> SEQ ID NO 33
<211> LENGTH: 366
<212> TYPE: DNA
<213> ORGANISM: Artificial Sequence
<220> FEATURE:
<223> OTHER INFORMATION: Synthetic

<400> SEQUENCE: 33
gaggtgcagc tggtggagtc tggaggaggc ttggtccagc ctgggggtc cctgagactc 60 tcctgtgcag cctctgggtt caccgtcagt aacaactaca tgagctgggt ccgccaggct 120
ccagggaagg ggctggagtg ggtctcagtt atttatagcg gtggtttcac atactacaca 180
gactccgtga agggccgatt caccatctcc agacacaatt ccaagaacac gctgtatctt 240
caaatgaaca gcctgagagc tgaggacacg gccgtgtatt actgtgcgag gtattactat 300
gatactagtg attattggac cttctttgac tactggggcc agggaaccct ggtcaccgtc 360
tcctca 366

<210> SEQ ID NO 34
<211> LENGTH: 122
<212> TYPE: PRT
<213> ORGANISM: Artificial Sequence
<220> FEATURE:
<223> OTHER INFORMATION: Synthetic

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asn Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Phe Thr Tyr Tyr Thr Asp Ser Val Lys
    50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Tyr Tyr Asp Thr Ser Asp Tyr Trp Thr Phe Phe Asp Tyr Trp
            100                 105                 110

Gly Gln Gly Thr Leu Val Thr Val Ser Ser
        115                 120
```

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35

```
gggttcaccg tcagtaacaa ctac                                            24
```

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

```
Gly Phe Thr Val Ser Asn Asn Tyr
1               5
```

<210> SEQ ID NO 37
<211> LENGTH: 21
<212> TYPE: DNA
<213> ORGANISM: Artificial Sequence
<220> FEATURE:
<223> OTHER INFORMATION: Synthetic

<400> SEQUENCE: 37

```
atttatagcg gtggtttcac a                                               21
```

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

```
Ile Tyr Ser Gly Gly Phe Thr
1               5
```

<210> SEQ ID NO 39
<211> LENGTH: 48
<212> TYPE: DNA
<213> ORGANISM: Artificial Sequence
<220> FEATURE:
<223> OTHER INFORMATION: Synthetic

<400> SEQUENCE: 39
gcgaggtatt actatgatac tagtgattat tggaccttct ttgactac 48

<210> SEQ ID NO 40
<211> LENGTH: 16
<212> TYPE: PRT
<213> ORGANISM: Artificial Sequence
<220> FEATURE:
<223> OTHER INFORMATION: Synthetic

<400> SEQUENCE: 40

Ala Arg Tyr Tyr Tyr Asp Thr Ser Asp Tyr Trp Thr Phe Phe Asp Tyr
1 5 10 15

<210> SEQ ID NO 41
<211> LENGTH: 321
<212> TYPE: DNA
<213> ORGANISM: Artificial Sequence
<220> FEATURE:
<223> OTHER INFORMATION: Synthetic

<400> SEQUENCE: 41
gaaatagtga tgacgcagtc tccagccacc ctgtctgtgt ctccagggga aagagccacc 60
ctctcctgca gggccagtca gagtgttagc agcaacttag cctggtacca gcagaaacct 120
ggccaggctc ccaggctcct catctatggt gcatccacca gggccactgg tatcccagcc 180
aggttcagtg gcagtgggtc tgggacagag ttcactctca ccatcagtag cctgcagtct 240
ggagattttg cagtttatta ctgtcagcag tataataact ggccgctcac tttcggcgga 300
gggaccaagg tggagatcaa t 321

<210> SEQ ID NO 42
<211> LENGTH: 107
<212> TYPE: PRT
<213> ORGANISM: Artificial Sequence
<220> FEATURE:
<223> OTHER INFORMATION: Synthetic

<400> SEQUENCE: 42

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Gly Asp Phe Ala Val Tyr Tyr Cys Gln Gln Tyr Asn Asn Trp Pro Leu
85 90 95

Thr Phe Gly Gly Gly Thr Lys Val Glu Ile Asn
100 105

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
cagagtgtta gcagcaac 18

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Ser Val Ser Ser Asn
1 5

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 ggtgcatcc 9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Gly Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
cagcagtata ataactggcc gctcact 27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Gln Gln Tyr Asn Asn Trp Pro Leu Thr
1 5

<210> SEQ ID NO 49
<211> LENGTH: 357
<212> TYPE: DNA
<213> ORGANISM: Artificial Sequence
<220> FEATURE:
<223> OTHER INFORMATION: Synthetic

<400> SEQUENCE: 49

```
caggtgcagc tggtggagtc tgggggaggc gtggtccagt ctgggaggtc cctgagactc     60

tcctgtgcag cgtctggatt caccttcagt agctatggca tgcactgggt ccgccaggct    120

ccaggcaagg ggctggagtg ggtggcagtt atatggtatg atggaagtaa tatatactat    180

tcagactccg tgaagggccg attcaccatc tccagagcca attccaagaa cacgctgtat    240

ctgcaaatga acagcctgag agccgaggac acggctgttt attactgtgc gagaccggga    300

cactggaact acttctttga atactggggc cagggaaccc tggtcaccgt ctcctca       357
```

<210> SEQ ID NO 50
<211> LENGTH: 119
<212> TYPE: PRT
<213> ORGANISM: Artificial Sequence
<220> FEATURE:
<223> OTHER INFORMATION: Synthetic

<400> SEQUENCE: 50

```
Gln Val Gln Leu Val Glu Ser Gly Gly Gly Val Val Gln Ser Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Ile Tyr Tyr Ser Asp Ser Val
    50                  55                  60

Lys Gly Arg Phe Thr Ile Ser Arg Ala Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Gly His Trp Asn Tyr Phe Phe Glu Tyr Trp Gly Gln Gly
            100                 105                 110

Thr Leu Val Thr Val Ser Ser
        115
```

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51

```
ggattcacct tcagtagcta tggc                                            24
```

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

```
Gly Phe Thr Phe Ser Ser Tyr Gly
1               5
```

<210> SEQ ID NO 53
<211> LENGTH: 24

<212> TYPE: DNA
<213> ORGANISM: Artificial Sequence
<220> FEATURE:
<223> OTHER INFORMATION: Synthetic

<400> SEQUENCE: 53
atatggtatg atggaagtaa tata 24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Trp Tyr Asp Gly Ser Asn Ile
1 5

<210> SEQ ID NO 55
<211> LENGTH: 36
<212> TYPE: DNA
<213> ORGANISM: Artificial Sequence
<220> FEATURE:
<223> OTHER INFORMATION: Synthetic

<400> SEQUENCE: 55
gcgagaccgg gacactggaa ctacttcttt gaatac 36

<210> SEQ ID NO 56
<211> LENGTH: 12
<212> TYPE: PRT
<213> ORGANISM: Artificial Sequence
<220> FEATURE:
<223> OTHER INFORMATION: Synthetic

<400> SEQUENCE: 56

Ala Arg Pro Gly His Trp Asn Tyr Phe Phe Glu Tyr
1 5 10

<210> SEQ ID NO 57
<211> LENGTH: 324
<212> TYPE: DNA
<213> ORGANISM: Artificial Sequence
<220> FEATURE:
<223> OTHER INFORMATION: Synthetic

<400> SEQUENCE: 57
gacatccaga tgacccagtc tccatcctcc ctgtctgcat ctgtaggaga cagagtcacc 60
atcacttgcc gggcaagtca gagcattaac aactatttaa attggtatca gcagaaacca 120
gggaaagccc ctaagctcct gatctatact gcatccagtt tgcaaagtgg ggtcccatca 180
aggttcagtg gcagtggatc tgggacagat ttcactctca ccatcagcag tctgcaacct 240
gaagattttg caacttacta ctgtcaacag agttacagta cccctccgct caccttcggc 300
caagggacac aactggagat taaa 324

<210> SEQ ID NO 58
<211> LENGTH: 108
<212> TYPE: PRT
<213> ORGANISM: Artificial Sequence
<220> FEATURE:
<223> OTHER INFORMATION: Synthetic

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
            20                  25                  30

Leu Asn Trp Tyr Gln Gln Lys Pro Gly Lys Ala Pro Lys Leu Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Leu Thr Phe Gly Gln Gly Thr Gln Leu Glu Ile Lys
            100                 105


<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59

cagagcatta acaactat                                                   18


<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Ser Ile Asn Asn Tyr
1               5


<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61

actgcatcc                                                              9


<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Thr Ala Ser
1


<210> SEQ ID NO 63
<211> LENGTH: 30
<212> TYPE: DNA
<213> ORGANISM: Artificial Sequence
<220> FEATURE:
<223> OTHER INFORMATION: Synthetic
```

<400> SEQUENCE: 63
caacagagtt acagtacccc tccgctcacc 30

<210> SEQ ID NO 64
<211> LENGTH: 10
<212> TYPE: PRT
<213> ORGANISM: Artificial Sequence
<220> FEATURE:
<223> OTHER INFORMATION: Synthetic

<400> SEQUENCE: 64

Gln Gln Ser Tyr Ser Thr Pro Pro Leu Thr
1 5 10

<210> SEQ ID NO 65
<211> LENGTH: 366
<212> TYPE: DNA
<213> ORGANISM: Artificial Sequence
<220> FEATURE:
<223> OTHER INFORMATION: Synthetic

<400> SEQUENCE: 65
gaggtgcagc tggtggagtc tgggggaggc ttggtacagc ctggggggtc cctgagactc 60
tcctgtggag cctctggatt caccttcagg aactacgaca tgcactgggt ccgccaaatt 120
acaggaaaag gtctggagtg ggtctcagct attggtagtg ctggtgacac atactatcca 180
gactccgtga agggccgatt caccatctcc agagaaaatg ccaagaactc cttgtatctt 240
caaatgaaca gcctgagagt cggggacacg gctgtgtatt actgtacaag agatatccat 300
tgtagtagta ccaggtgcta cggtatggac gtctggggcc aagggaccac ggtcaccgtc 360
tcctca 366

<210> SEQ ID NO 66
<211> LENGTH: 122
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Val Gln Pro Gly Gly
1 5 10 15

Ser Leu Arg Leu Ser Cys Gly Ala Ser Gly Phe Thr Phe Arg Asn Tyr
20 25 30

Asp Met His Trp Val Arg Gln Ile Thr Gly Lys Gly Leu Glu Trp Val
35 40 45

Ser Ala Ile Gly Ser Ala Gly Asp Thr Tyr Tyr Pro Asp Ser Val Lys
50 55 60

Gly Arg Phe Thr Ile Ser Arg Glu Asn Ala Lys Asn Ser Leu Tyr Leu
65 70 75 80

Gln Met Asn Ser Leu Arg Val Gly Asp Thr Ala Val Tyr Tyr Cys Thr
85 90 95

Arg Asp Ile His Cys Ser Ser Thr Arg Cys Tyr Gly Met Asp Val Trp
100 105 110

Gly Gln Gly Thr Thr Val Thr Val Ser Ser
115 120

<210> SEQ ID NO 67
<211> LENGTH: 24
<212> TYPE: DNA

<213> ORGANISM: Artificial Sequence
<220> FEATURE:
<223> OTHER INFORMATION: Synthetic

<400> SEQUENCE: 67
ggattcacct tcaggaacta cgac 24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Phe Thr Phe Arg Asn Tyr Asp
1 5

<210> SEQ ID NO 69
<211> LENGTH: 21
<212> TYPE: DNA
<213> ORGANISM: Artificial Sequence
<220> FEATURE:
<223> OTHER INFORMATION: Synthetic

<400> SEQUENCE: 69
attggtagtg ctggtgacac a 21

<210> SEQ ID NO 70
<211> LENGTH: 7
<212> TYPE: PRT
<213> ORGANISM: Artificial Sequence
<220> FEATURE:
<223> OTHER INFORMATION: Synthetic

<400> SEQUENCE: 70

Ile Gly Ser Ala Gly Asp Thr
1 5

<210> SEQ ID NO 71
<211> LENGTH: 48
<212> TYPE: DNA
<213> ORGANISM: Artificial Sequence
<220> FEATURE:
<223> OTHER INFORMATION: Synthetic

<400> SEQUENCE: 71
acaagagata tccattgtag tagtaccagg tgctacggta tggacgtc 48

<210> SEQ ID NO 72
<211> LENGTH: 16
<212> TYPE: PRT
<213> ORGANISM: Artificial Sequence
<220> FEATURE:
<223> OTHER INFORMATION: Synthetic

<400> SEQUENCE: 72

Thr Arg Asp Ile His Cys Ser Ser Thr Arg Cys Tyr Gly Met Asp Val
1 5 10 15

<210> SEQ ID NO 73
<211> LENGTH: 324
<212> TYPE: DNA
<213> ORGANISM: Artificial Sequence
<220> FEATURE:
<223> OTHER INFORMATION: Synthetic

```
<400> SEQUENCE: 73

gacatccaga tgacccagtc tccatcctcc ctgtctgcat ctgtaggaga cagagtcacc      60

atcacttgcc gggcaagtca gagcattagc aactatttaa attggtatca gcagaaacca     120

gggaaagccc ctaagctcct gatctatgct gcatccagtt tgcaaagtgg ggtcccatca     180

aggttcagtg gcagtggatc tgggacagat ttcactctca ccatcagcag tctgcaacct     240

gaagattttg caacttacta ctgtcaacag agttacagta cccctccgat caccttcggc     300

caagggacac gactggagat taaa                                            324


<210> SEQ ID NO 74
<211> LENGTH: 108
<212> TYPE: PRT
<213> ORGANISM: Artificial Sequence
<220> FEATURE:
<223> OTHER INFORMATION: Synthetic

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105


<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75

cagagcatta gcaactat                                                    18


<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

Gln Ser Ile Ser Asn Tyr
1               5


<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77
```

gctgcatcc 9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Ala Ala Ser
1

<210> SEQ ID NO 79
<211> LENGTH: 30
<212> TYPE: DNA
<213> ORGANISM: Artificial Sequence
<220> FEATURE:
<223> OTHER INFORMATION: Synthetic

<400> SEQUENCE: 79
caacagagtt acagtacccc tccgatcacc 30

<210> SEQ ID NO 80
<211> LENGTH: 10
<212> TYPE: PRT
<213> ORGANISM: Artificial Sequence
<220> FEATURE:
<223> OTHER INFORMATION: Synthetic

<400> SEQUENCE: 80

Gln Gln Ser Tyr Ser Thr Pro Pro Ile Thr
1 5 10

<210> SEQ ID NO 81
<211> LENGTH: 390
<212> TYPE: DNA
<213> ORGANISM: Artificial Sequence
<220> FEATURE:
<223> OTHER INFORMATION: Synthetic

<400> SEQUENCE: 81
gaggtgcagc tggtggagtc tgggggaggc ttggtaaagc ctggggggtc ccttcgactc 60
tcctgtgcag cctctggatt caaattcagt aatgaatgga tgagctgggt ccgccaggct 120
ccagggaagg ggctggagtg ggttggccgt attaaaagca aaactgatgg tgggacaaca 180
gactacgctg cacccgtgaa aggcagattc accatctcaa gagatgattc aaaaaatacg 240
ctgtatctgc aaatgaacag cctgaaaacc gaggacacag ccgtgtatta ctgtaccaca 300
gatcaagatt tttggagtgg ttattatacc ggggctgact actacggtat ggacgtctgg 360
ggccaaggga ccatggtcac cgtctcctca 390

<210> SEQ ID NO 82
<211> LENGTH: 130
<212> TYPE: PRT
<213> ORGANISM: Artificial Sequence
<220> FEATURE:
<223> OTHER INFORMATION: Synthetic

<400> SEQUENCE: 82

Glu Val Gln Leu Val Glu Ser Gly Gly Gly Leu Val Lys Pro Gly Gly
1 5 10 15

Ser Leu Arg Leu Ser Cys Ala Ala Ser Gly Phe Lys Phe Ser Asn Glu

```
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Gln Asp Phe Trp Ser Gly Tyr Tyr Thr Gly Ala
            100                 105                 110

Asp Tyr Tyr Gly Met Asp Val Trp Gly Gln Gly Thr Met Val Thr Val
        115                 120                 125

Ser Ser
    130


<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83

ggattcaaat tcagtaatga atgg                                            24


<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Gly Phe Lys Phe Ser Asn Glu Trp
1               5


<210> SEQ ID NO 85
<211> LENGTH: 30
<212> TYPE: DNA
<213> ORGANISM: Artificial Sequence
<220> FEATURE:
<223> OTHER INFORMATION: Synthetic

<400> SEQUENCE: 85

attaaaagca aaactgatgg tgggacaaca                                      30


<210> SEQ ID NO 86
<211> LENGTH: 10
<212> TYPE: PRT
<213> ORGANISM: Artificial Sequence
<220> FEATURE:
<223> OTHER INFORMATION: Synthetic

<400> SEQUENCE: 86

Ile Lys Ser Lys Thr Asp Gly Gly Thr Thr
1               5                   10


<210> SEQ ID NO 87
<211> LENGTH: 63
<212> TYPE: DNA
<213> ORGANISM: Artificial Sequence
<220> FEATURE:
```

<223> OTHER INFORMATION: Synthetic

<400> SEQUENCE: 87

```
accacagatc aagatttttg gagtggttat tataccgggg ctgactacta cggtatggac     60

gtc                                                                   63
```

<210> SEQ ID NO 88
<211> LENGTH: 21
<212> TYPE: PRT
<213> ORGANISM: Artificial Sequence
<220> FEATURE:
<223> OTHER INFORMATION: Synthetic

<400> SEQUENCE: 88

```
Thr Thr Asp Gln Asp Phe Trp Ser Gly Tyr Tyr Thr Gly Ala Asp Tyr
1               5                   10                  15

Tyr Gly Met Asp Val
            20
```

<210> SEQ ID NO 89
<211> LENGTH: 324
<212> TYPE: DNA
<213> ORGANISM: Artificial Sequence
<220> FEATURE:
<223> OTHER INFORMATION: Synthetic

<400> SEQUENCE: 89

```
gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttacta ctgtcaacag agttacagta cccctccgat caccttcggc    300

caagggacac gactggagat taaa                                           324
```

<210> SEQ ID NO 90
<211> LENGTH: 108
<212> TYPE: PRT
<213> ORGANISM: Artificial Sequence
<220> FEATURE:
<223> OTHER INFORMATION: Synthetic

<400> SEQUENCE: 90

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 91

<211> LENGTH: 18
<212> TYPE: DNA
<213> ORGANISM: Artificial Sequence
<220> FEATURE:
<223> OTHER INFORMATION: Synthetic

<400> SEQUENCE: 91
cagagcatta gcagctat 18

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Ser Ile Ser Ser Tyr
1 5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 gctgcatcc 9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Ala Ala Ser
1

<210> SEQ ID NO 95
<211> LENGTH: 30
<212> TYPE: DNA
<213> ORGANISM: Artificial Sequence
<220> FEATURE:
<223> OTHER INFORMATION: Synthetic

<400> SEQUENCE: 95
caacagagtt acagtacccc tccgatcacc 30

<210> SEQ ID NO 96
<211> LENGTH: 10
<212> TYPE: PRT
<213> ORGANISM: Artificial Sequence
<220> FEATURE:
<223> OTHER INFORMATION: Synthetic

<400> SEQUENCE: 96

Gln Gln Ser Tyr Ser Thr Pro Pro Ile Thr
1 5 10

<210> SEQ ID NO 97
<211> LENGTH: 348
<212> TYPE: DNA
<213> ORGANISM: Artificial Sequence
<220> FEATURE:

<223> OTHER INFORMATION: Synthetic

<400> SEQUENCE: 97

```
cagatgcagc tccaacagtg gggcgcagga ctattgaagc cttcggagac cctgtccctc     60

acctgcgttg tctatggtgg gtccctcaat ggatactatt ggagctggat ccgccagtcc    120

cccgggaagg ggctggagtg gattggggaa atcgatcata gtggaagcac caactacaac    180

ccgtccctca agaatcgagt caccatgtca gtagacacgt ctaagattca gttctccctg    240

aaactgacct ctgtgaccgt cgcggacacg gctgtgtatt actgtgcgag agaaggatta    300

ttaccctttg actattgggg ccagggaacc ctggtcaccg tctcctca                 348
```

<210> SEQ ID NO 98
<211> LENGTH: 116
<212> TYPE: PRT
<213> ORGANISM: Artificial Sequence
<220> FEATURE:
<223> OTHER INFORMATION: Synthetic

<400> SEQUENCE: 98

```
Gln Met Gln Leu Gln Gln Trp Gly Ala Gly Leu Leu Lys Pro Ser Glu
1               5                   10                  15

Thr Leu Ser Leu Thr Cys Val Val Tyr Gly Gly Ser Leu Asn Gly Tyr
            20                  25                  30

Tyr Trp Ser Trp Ile Arg Gln Ser Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Asn Arg Val Thr Met Ser Val Asp Thr Ser Lys Ile Gln Phe Ser Leu
65                  70                  75                  80

Lys Leu Thr Ser Val Thr Val Ala Asp Thr Ala Val Tyr Tyr Cys Ala
                85                  90                  95

Arg Glu Gly Leu Leu Pro Phe Asp Tyr Trp Gly Gln Gly Thr Leu Val
            100                 105                 110

Thr Val Ser Ser
        115
```

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99

```
ggtgggtccc tcaatggata ctat                                            24
```

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

```
Gly Gly Ser Leu Asn Gly Tyr Tyr
1               5
```

<210> SEQ ID NO 101
<211> LENGTH: 21
<212> TYPE: DNA

<213> ORGANISM: Artificial Sequence
<220> FEATURE:
<223> OTHER INFORMATION: Synthetic

<400> SEQUENCE: 101
atcgatcata gtggaagcac c 21

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Ile Asp His Ser Gly Ser Thr
1 5

<210> SEQ ID NO 103
<211> LENGTH: 30
<212> TYPE: DNA
<213> ORGANISM: Artificial Sequence
<220> FEATURE:
<223> OTHER INFORMATION: Synthetic

<400> SEQUENCE: 103
gcgagagaag gattattacc ctttgactat 30

<210> SEQ ID NO 104
<211> LENGTH: 10
<212> TYPE: PRT
<213> ORGANISM: Artificial Sequence
<220> FEATURE:
<223> OTHER INFORMATION: Synthetic

<400> SEQUENCE: 104

Ala Arg Glu Gly Leu Leu Pro Phe Asp Tyr
1 5 10

<210> SEQ ID NO 105
<211> LENGTH: 324
<212> TYPE: DNA
<213> ORGANISM: Artificial Sequence
<220> FEATURE:
<223> OTHER INFORMATION: Synthetic

<400> SEQUENCE: 105
gaaattgtgt tgacgcagtc tccaggcacc ctgtctttgt ctccagggga aagagtcacc 60
ctctcctgca gggccagtca gagtgtttac agcaactact tagcctggta ccagcagaat 120
cctggccagg ctcccaggct cctcatctat gctgcatcca acagggccac tggcatccca 180
gacaggttca gtggcagtgg gtctgggaca gacttcactc tcaccatcag cagactggag 240
cctgaagatt ttgcggtgta ttactgtcat cagtatgcta cctcaccttg gacgttcggc 300
caagggacca aggtggaaat caaa 324

<210> SEQ ID NO 106
<211> LENGTH: 108
<212> TYPE: PRT
<213> ORGANISM: Artificial Sequence
<220> FEATURE:
<223> OTHER INFORMATION: Synthetic

<400> SEQUENCE: 106

Glu Ile Val Leu Thr Gln Ser Pro Gly Thr Leu Ser Leu Ser Pro Gly

```
1               5                   10                  15

Glu Arg Val Thr Leu Ser Cys Arg Ala Ser Gln Ser Val Tyr Ser Asn
            20                  25                  30

Tyr Leu Ala Trp Tyr Gln Gln Asn Pro Gly Gln Ala Pro Arg Leu Leu
        35                  40                  45

Ile Tyr Ala Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr Ala Thr Ser Pro
                85                  90                  95

Trp Thr Phe Gly Gln Gly Thr Lys Val Glu Ile Lys
            100                 105
```

<210> SEQ ID NO 107
<211> LENGTH: 21
<212> TYPE: DNA
<213> ORGANISM: Artificial Sequence
<220> FEATURE:
<223> OTHER INFORMATION: Synthetic

<400> SEQUENCE: 107

```
cagagtgttt acagcaacta c                                              21
```

<210> SEQ ID NO 108
<211> LENGTH: 7
<212> TYPE: PRT
<213> ORGANISM: Artificial Sequence
<220> FEATURE:
<223> OTHER INFORMATION: Synthetic

<400> SEQUENCE: 108

```
Gln Ser Val Tyr Ser Asn Tyr
1               5
```

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109

```
gctgcatcc                                                             9
```

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

```
Ala Ala Ser
1
```

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
catcagtatg ctacctcacc ttggacg 27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

His Gln Tyr Ala Thr Ser Pro Trp Thr
1 5

<210> SEQ ID NO 113
<211> LENGTH: 369
<212> TYPE: DNA
<213> ORGANISM: Artificial Sequence
<220> FEATURE:
<223> OTHER INFORMATION: Synthetic

<400> SEQUENCE: 113
cagctgcagc tgcaggagtc gggcccagat ctggtgaagc cttcggatac cctgtccctc 60
acctgcactg tctctgatga ctccatcagc agtactactt actactgggc ctggatccgc 120
cagcccccag ggaaggggct ggaatggatt ggcagtatgt cttataatgg gaacaactac 180
tacaacccgt ccctcaagag tcgagtcgcc atatccgcag gcacgtccca gaaacagttc 240
tccctgaaac tgacctctgt gactgccgca gacacggctg tttatcactg tgcgagacat 300
cttggatata acggcaactg gtaccccttt gacttctggg gccagggaat tctggtcacc 360
gtctcctct 369

<210> SEQ ID NO 114
<211> LENGTH: 123
<212> TYPE: PRT
<213> ORGANISM: Artificial Sequence
<220> FEATURE:
<223> OTHER INFORMATION: Synthetic

<400> SEQUENCE: 114

Gln Leu Gln Leu Gln Glu Ser Gly Pro Asp Leu Val Lys Pro Ser Asp
1 5 10 15

Thr Leu Ser Leu Thr Cys Thr Val Ser Asp Asp Ser Ile Ser Ser Thr
20 25 30

Thr Tyr Tyr Trp Ala Trp Ile Arg Gln Pro Pro Gly Lys Gly Leu Glu
35 40 45

Trp Ile Gly Ser Met Ser Tyr Asn Gly Asn Asn Tyr Tyr Asn Pro Ser
50 55 60

Leu Lys Ser Arg Val Ala Ile Ser Ala Gly Thr Ser Gln Lys Gln Phe
65 70 75 80

Ser Leu Lys Leu Thr Ser Val Thr Ala Ala Asp Thr Ala Val Tyr His
85 90 95

Cys Ala Arg His Leu Gly Tyr Asn Gly Asn Trp Tyr Pro Phe Asp Phe
100 105 110

Trp Gly Gln Gly Ile Leu Val Thr Val Ser Ser
115 120

<210> SEQ ID NO 115
<211> LENGTH: 30
<212> TYPE: DNA
<213> ORGANISM: Artificial Sequence
<220> FEATURE:
<223> OTHER INFORMATION: Synthetic

<400> SEQUENCE: 115
gatgactcca tcagcagtac tacttactac 30

<210> SEQ ID NO 116
<211> LENGTH: 10
<212> TYPE: PRT
<213> ORGANISM: Artificial Sequence
<220> FEATURE:
<223> OTHER INFORMATION: Synthetic

<400> SEQUENCE: 116

Asp Asp Ser Ile Ser Ser Thr Thr Tyr Tyr
1 5 10

<210> SEQ ID NO 117
<211> LENGTH: 21
<212> TYPE: DNA
<213> ORGANISM: Artificial Sequence
<220> FEATURE:
<223> OTHER INFORMATION: Synthetic

<400> SEQUENCE: 117
atgtcttata atgggaacaa c 21

<210> SEQ ID NO 118
<211> LENGTH: 7
<212> TYPE: PRT
<213> ORGANISM: Artificial Sequence
<220> FEATURE:
<223> OTHER INFORMATION: Synthetic

<400> SEQUENCE: 118

Met Ser Tyr Asn Gly Asn Asn
1 5

<210> SEQ ID NO 119
<211> LENGTH: 45
<212> TYPE: DNA
<213> ORGANISM: Artificial Sequence
<220> FEATURE:
<223> OTHER INFORMATION: Synthetic

<400> SEQUENCE: 119
gcgagacatc ttggatataa cggcaactgg tacccctttg acttc 45

<210> SEQ ID NO 120
<211> LENGTH: 15
<212> TYPE: PRT
<213> ORGANISM: Artificial Sequence
<220> FEATURE:
<223> OTHER INFORMATION: Synthetic

<400> SEQUENCE: 120

Ala Arg His Leu Gly Tyr Asn Gly Asn Trp Tyr Pro Phe Asp Phe
1 5 10 15

<210> SEQ ID NO 121
<211> LENGTH: 324
<212> TYPE: DNA
<213> ORGANISM: Artificial Sequence
<220> FEATURE:
<223> OTHER INFORMATION: Synthetic

<400> SEQUENCE: 121
gaaattgtgt tgacgcagtc tccaggcacc ctgtctttgt ctccaggaga aagagccacc 60
ctctcctgca gggccagtca gagtgttagt agtagttatt tagcctggta ccagcagaaa 120
cctggccagg ctcccaggct cctcatctat ggtgcatcca gcaggaccac tggcatccca 180
gacaggttca gtggcagtgg gtctgggaca gacttcactc tcaccatcag cagactggag 240
cctgaagatt ttgcagtgta ttactgtcag cagtatggta gctcaccttg gacgttcggc 300
caagggacca aggtggaaat caaa 324

<210> SEQ ID NO 122
<211> LENGTH: 108
<212> TYPE: PRT
<213> ORGANISM: Artificial Sequence
<220> FEATURE:
<223> OTHER INFORMATION: Synthetic

<400> SEQUENCE: 122

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Thr Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 123
<211> LENGTH: 21
<212> TYPE: DNA
<213> ORGANISM: Artificial Sequence
<220> FEATURE:
<223> OTHER INFORMATION: Synthetic

<400> SEQUENCE: 123
cagagtgtta gtagtagtta t 21

<210> SEQ ID NO 124
<211> LENGTH: 7
<212> TYPE: PRT
<213> ORGANISM: Artificial Sequence
<220> FEATURE:
<223> OTHER INFORMATION: Synthetic

<400> SEQUENCE: 124

```
Gln Ser Val Ser Ser Ser Tyr
1               5
```

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 ggtgcatcc 9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Gly Ala Ser
1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
cagcagtatg gtagctcacc ttggacg 27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Gln Tyr Gly Ser Ser Pro Trp Thr
1 5

<210> SEQ ID NO 129
<211> LENGTH: 366
<212> TYPE: DNA
<213> ORGANISM: Artificial Sequence
<220> FEATURE:
<223> OTHER INFORMATION: Synthetic

<400> SEQUENCE: 129
gaagtgcagg tggtagagtc tgggggcggc ttggtcgagc ctggcaggtc cctgagactc 60
tcctgtaaag cctctggatt cacctttgat gattatgcca tgcactgggt ccgacaaact 120
ccagggaagg ccctggagtg ggtctcgggt attaattgga gtggtaataa cataggctat 180
gcggactctg tgaagggccg attcaccatc tccaaggacg acgccaagaa ctccctgtat 240
ctgcaaatga acagtctgag acctgaggac acggccttat attactgtac aaaagatata 300
agtataactg gaaccctcga tgcttttgat gtctggggcc aagggacaat ggtcaccgtc 360
tcttca 366

<210> SEQ ID NO 130
<211> LENGTH: 122
<212> TYPE: PRT
<213> ORGANISM: Artificial Sequence
<220> FEATURE:
<223> OTHER INFORMATION: Synthetic

<400> SEQUENCE: 130

Glu Val Gln Val Val Glu Ser Gly Gly Gly Leu Val Glu Pro Gly Arg
1 5 10 15

Ser Leu Arg Leu Ser Cys Lys Ala Ser Gly Phe Thr Phe Asp Asp Tyr
20 25 30

```
Ala Met His Trp Val Arg Gln Thr Pro Gly Lys Ala Leu Glu Trp Val
        35                  40                  45

Ser Gly Ile Asn Trp Ser Gly Asn Asn Ile Gly Tyr Ala Asp Ser Val
    50                  55                  60

Lys Gly Arg Phe Thr Ile Ser Lys Asp Asp Ala Lys Asn Ser Leu Tyr
65                  70                  75                  80

Leu Gln Met Asn Ser Leu Arg Pro Glu Asp Thr Ala Leu Tyr Tyr Cys
                85                  90                  95

Thr Lys Asp Ile Ser Ile Thr Gly Thr Leu Asp Ala Phe Asp Val Trp
            100                 105                 110

Gly Gln Gly Thr Met Val Thr Val Ser Ser
        115                 120


<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131

ggattcacct ttgatgatta tgcc                                          24


<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Phe Thr Phe Asp Asp Tyr Ala
1               5


<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133

attaattgga gtggtaataa cata                                          24


<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Ile Asn Trp Ser Gly Asn Asn Ile
1               5


<210> SEQ ID NO 135
<211> LENGTH: 45
<212> TYPE: DNA
<213> ORGANISM: Artificial Sequence
<220> FEATURE:
<223> OTHER INFORMATION: Synthetic

<400> SEQUENCE: 135
```

acaaaagata taagtataac tggaaccctc gatgcttttg atgtc 45

<210> SEQ ID NO 136
<211> LENGTH: 15
<212> TYPE: PRT
<213> ORGANISM: Artificial Sequence
<220> FEATURE:
<223> OTHER INFORMATION: Synthetic

<400> SEQUENCE: 136

Thr Lys Asp Ile Ser Ile Thr Gly Thr Leu Asp Ala Phe Asp Val
1 5 10 15

<210> SEQ ID NO 137
<211> LENGTH: 321
<212> TYPE: DNA
<213> ORGANISM: Artificial Sequence
<220> FEATURE:
<223> OTHER INFORMATION: Synthetic

<400> SEQUENCE: 137
gacatccaga tgacccagtc tccaatttcc gtgtctgcat ctgtaggaga cagagtcacc 60
atcacttgtc gggcgagtca gggtattagc aactggttag cctggtatca gcagaaacca 120
gggatagccc ctaaactcct gatctattct gcatccagtt tacaaagtgg ggtcccatca 180
aggttcagag gcagtggatc tgggacagac ttcactctca ccatcggcag cctgcagcct 240
gaagattttg caacttacta ttgtcaacag gctcacagtt tcccgctcac tttcggcgga 300
gggaccaagg tggagatcaa a 321

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Asp Ile Gln Met Thr Gln Ser Pro Ile Ser Val Ser Ala Ser Val Gly
1 5 10 15

Asp Arg Val Thr Ile Thr Cys Arg Ala Ser Gln Gly Ile Ser Asn Trp
20 25 30

Leu Ala Trp Tyr Gln Gln Lys Pro Gly Ile Ala Pro Lys Leu Leu Ile
35 40 45

Tyr Ser Ala Ser Ser Leu Gln Ser Gly Val Pro Ser Arg Phe Arg Gly
50 55 60

Ser Gly Ser Gly Thr Asp Phe Thr Leu Thr Ile Gly Ser Leu Gln Pro
65 70 75 80

Glu Asp Phe Ala Thr Tyr Tyr Cys Gln Gln Ala His Ser Phe Pro Leu
85 90 95

Thr Phe Gly Gly Gly Thr Lys Val Glu Ile Lys
100 105

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139
cagggtatta gcaactgg 18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

Gln Gly Ile Ser Asn Trp
1               5

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 tctgcatcc 9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Ser Ala Ser
1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
caacaggctc acagtttccc gctcact 27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Gln Gln Ala His Ser Phe Pro Leu Thr
1               5

<210> SEQ ID NO 145
<211> LENGTH: 348
<212> TYPE: DNA
<213> ORGANISM: Artificial Sequence
<220> FEATURE:
<223> OTHER INFORMATION: Synthetic

<400> SEQUENCE: 145
caggtgcaat tagtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcaatt atatggtctg atggagatag tgaatataat 180
ctagactccg taaagggccg attcaccatc tccagagaca attccaagaa cacgctgtat 240
ctgcaaatga acagtctgag agtcgaagac tcggctgtat attactgtgc gagagatcga 300
gaccttgagg atatctgggg ccaagggaca atggtcaccg tctcttca 348

<210> SEQ ID NO 146
<211> LENGTH: 116
<212> TYPE: PRT
<213> ORGANISM: Artificial Sequence
<220> FEATURE:
<223> OTHER INFORMATION: Synthetic

<400> SEQUENCE: 146

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Ile Ile Trp Ser Asp Gly Asp Ser Glu Tyr Asn Leu Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Val Glu Asp Ser Ala Val Tyr Tyr Cys
85 90 95

Ala Arg Asp Arg Asp Leu Glu Asp Ile Trp Gly Gln Gly Thr Met Val
100 105 110

Thr Val Ser Ser
115

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggattcacct tcagtagcta tggc 24

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Phe Thr Phe Ser Ser Tyr Gly
1 5

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
atatggtctg atggagatag tgaa 24

```
<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Trp Ser Asp Gly Asp Ser Glu
1               5


<210> SEQ ID NO 151
<211> LENGTH: 27
<212> TYPE: DNA
<213> ORGANISM: Artificial Sequence
<220> FEATURE:
<223> OTHER INFORMATION: Synthetic

<400> SEQUENCE: 151

gcgagagatc gagaccttga ggatatc                                          27


<210> SEQ ID NO 152
<211> LENGTH: 9
<212> TYPE: PRT
<213> ORGANISM: Artificial Sequence
<220> FEATURE:
<223> OTHER INFORMATION: Synthetic

<400> SEQUENCE: 152

Ala Arg Asp Arg Asp Leu Glu Asp Ile
1               5


<210> SEQ ID NO 153
<211> LENGTH: 321
<212> TYPE: DNA
<213> ORGANISM: Artificial Sequence
<220> FEATURE:
<223> OTHER INFORMATION: Synthetic

<400> SEQUENCE: 153

gacatccaga tgacccagtc tccatcctcc ctgtctgcat ctgtcggaga cagagtcacc     60

atcacttgcc gggcaagtca gggcattaga aatgatttag gctggtatca gcagaaacca    120

gggaaagccc ctaagcgcct gatctatgct gcatccaatt tgcaaagtgg ggtcccatca    180

aggttcagcg gcagtggatc tgggacagag ttcactctca caatcagcag cctgcagcct    240

gaagattttg caacttatta ctgtctacag cataatagtt atccgctcac tttcggcgga    300

gggaccaagg tggagatcaa a                                              321


<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Asn Leu Gln Ser Gly Val Pro Ser Arg Phe Ser Gly
```

```
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105


<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155

cagggcatta gaaatgat                                                   18


<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Gln Gly Ile Arg Asn Asp
1               5


<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157

gctgcatcc                                                              9


<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Ala Ala Ser
1


<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159

ctacagcata atagttatcc gctcact                                         27


<210> SEQ ID NO 160
<211> LENGTH: 9
<212> TYPE: PRT
<213> ORGANISM: Artificial Sequence
<220> FEATURE:
```

<223> OTHER INFORMATION: Synthetic

<400> SEQUENCE: 160

Leu Gln His Asn Ser Tyr Pro Leu Thr
1 5

<210> SEQ ID NO 161
<211> LENGTH: 351
<212> TYPE: DNA
<213> ORGANISM: Artificial Sequence
<220> FEATURE:
<223> OTHER INFORMATION: Synthetic

<400> SEQUENCE: 161
gaggtgcagt tgttggagtc tgggggagtt ttggtacagc ctggggggtc cctgagactc 60
tcctgtgcag cctctggatt cacctttagt aattttggca tgacgtgggt ccgccaggct 120
ccagggaagg gactggagtg ggtctcaggt attagtggtg gcggtcgtga cacatacttc 180
gcagactccg tgaagggccg gttcaccatc tccagagaca attccaagaa tacgttgtat 240
ctacagatga acagcctgaa aggcgaggac acggccgtat attactgtgt gaagtgggga 300
aatatttact ttgactactg gggccaggga accctggtca ccgtctcatc a 351

<210> SEQ ID NO 162
<211> LENGTH: 117
<212> TYPE: PRT
<213> ORGANISM: Artificial Sequence
<220> FEATURE:
<223> OTHER INFORMATION: Synthetic

<400> SEQUENCE: 162

Glu Val Gln Leu Leu Glu Ser Gly Gly Val Leu Val Gln Pro Gly Gly
1 5 10 15

Ser Leu Arg Leu Ser Cys Ala Ala Ser Gly Phe Thr Phe Ser Asn Phe
20 25 30

Gly Met Thr Trp Val Arg Gln Ala Pro Gly Lys Gly Leu Glu Trp Val
35 40 45

Ser Gly Ile Ser Gly Gly Gly Arg Asp Thr Tyr Phe Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Lys Gly Glu Asp Thr Ala Val Tyr Tyr Cys
85 90 95

Val Lys Trp Gly Asn Ile Tyr Phe Asp Tyr Trp Gly Gln Gly Thr Leu
100 105 110

Val Thr Val Ser Ser
115

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163
ggattcacct ttagtaattt tggc 24

<210> SEQ ID NO 164
<211> LENGTH: 8
<212> TYPE: PRT

<213> ORGANISM: Artificial Sequence
<220> FEATURE:
<223> OTHER INFORMATION: Synthetic

<400> SEQUENCE: 164

Gly Phe Thr Phe Ser Asn Phe Gly
1               5

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
attagtggtg gcggtcgtga caca 24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ile Ser Gly Gly Gly Arg Asp Thr
1               5

<210> SEQ ID NO 167
<211> LENGTH: 30
<212> TYPE: DNA
<213> ORGANISM: Artificial Sequence
<220> FEATURE:
<223> OTHER INFORMATION: Synthetic

<400> SEQUENCE: 167
gtgaagtggg gaaatattta ctttgactac 30

<210> SEQ ID NO 168
<211> LENGTH: 10
<212> TYPE: PRT
<213> ORGANISM: Artificial Sequence
<220> FEATURE:
<223> OTHER INFORMATION: Synthetic

<400> SEQUENCE: 168

Val Lys Trp Gly Asn Ile Tyr Phe Asp Tyr
1               5                   10

<210> SEQ ID NO 169
<211> LENGTH: 321
<212> TYPE: DNA
<213> ORGANISM: Artificial Sequence
<220> FEATURE:
<223> OTHER INFORMATION: Synthetic

<400> SEQUENCE: 169
gacatccaga tgacccagtc tccatcctcc ctgtctgcat ctgtcggaga cagcatcacc 60
atcacttgcc gggcgagtct gtccattaac accttttttaa attggtatca gcagaaacca 120
gggaaagccc ctaacctcct gatctatgct gcgtccagtt tacatggtgg ggtcccatca 180
aggttcagtg gcagcggctc tgggacagat ttcactctca ccatcagaac tcttcaacct 240
gaagattttg caacttacta ctgtcaacag agttccaata ccccattcac tttcggccct 300

```
gggaccgtag tggatttcag a                                               321


<210> SEQ ID NO 170
<211> LENGTH: 107
<212> TYPE: PRT
<213> ORGANISM: Artificial Sequence
<220> FEATURE:
<223> OTHER INFORMATION: Synthetic

<400> SEQUENCE: 170

Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Gly Val Pro Ser Arg Phe Ser Gly
    50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg
            100                 105


<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171

ctgtccatta acaccttt                                                    18


<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

Leu Ser Ile Asn Thr Phe
1               5


<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173

gctgcgtcc                                                               9


<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174
```

```
Ala Ala Ser
1


<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175

caacagagtt ccaataccc attcact                                          27


<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Gln Gln Ser Ser Asn Thr Pro Phe Thr
1               5


<210> SEQ ID NO 177
<211> LENGTH: 363
<212> TYPE: DNA
<213> ORGANISM: Artificial Sequence
<220> FEATURE:
<223> OTHER INFORMATION: Synthetic

<400> SEQUENCE: 177

gaggtgcagc tggtggagtc tgggggagga gtggtacggc cggggggtc cctgagactc      60

tcctgtgcag cctctggatt cacttttgat gactatggca tgagttgggt ccgccaagtt    120

ccagggaagg ggctggagtg ggtctcaggt attagttgga atgatggtaa gacagtttat    180

gcagagtctg tgaagggccg attcatcatc tccagagaca acgccaagaa ctccctgtat    240

ctggaaatga atagtctgag agccgaggac acggccttat attactgtgc gagagattgg    300

cagtacttga tagagcggta ctttgactac tggggccagg gaaccctggt caccgtctcc    360

tca                                                                  363


<210> SEQ ID NO 178
<211> LENGTH: 121
<212> TYPE: PRT
<213> ORGANISM: Artificial Sequence
<220> FEATURE:
<223> OTHER INFORMATION: Synthetic

<400> SEQUENCE: 178

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Val Pro Gly Lys Gly Leu Glu Trp Val
        35                  40                  45

Ser Gly Ile Ser Trp Asn Asp Gly Lys Thr Val Tyr Ala Glu Ser Val
    50                  55                  60

Lys Gly Arg Phe Ile Ile Ser Arg Asp Asn Ala Lys Asn Ser Leu Tyr
65                  70                  75                  80

Leu Glu Met Asn Ser Leu Arg Ala Glu Asp Thr Ala Leu Tyr Tyr Cys
```

```
                85                  90                  95

Ala Arg Asp Trp Gln Tyr Leu Ile Glu Arg Tyr Phe Asp Tyr Trp Gly
            100                 105                 110

Gln Gly Thr Leu Val Thr Val Ser Ser
        115                 120


<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179

ggattcactt ttgatgacta tggc                                            24


<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

Gly Phe Thr Phe Asp Asp Tyr Gly
1               5


<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181

attagttgga atgatggtaa gaca                                            24


<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182

Ile Ser Trp Asn Asp Gly Lys Thr
1               5


<210> SEQ ID NO 183
<211> LENGTH: 42
<212> TYPE: DNA
<213> ORGANISM: Artificial Sequence
<220> FEATURE:
<223> OTHER INFORMATION: Synthetic

<400> SEQUENCE: 183

gcgagagatt ggcagtactt gatagagcgg tactttgact ac                        42


<210> SEQ ID NO 184
<211> LENGTH: 14
<212> TYPE: PRT
<213> ORGANISM: Artificial Sequence
<220> FEATURE:
<223> OTHER INFORMATION: Synthetic

<400> SEQUENCE: 184
```

```
Ala Arg Asp Trp Gln Tyr Leu Ile Glu Arg Tyr Phe Asp Tyr
1               5                   10


<210> SEQ ID NO 185
<211> LENGTH: 324
<212> TYPE: DNA
<213> ORGANISM: Artificial Sequence
<220> FEATURE:
<223> OTHER INFORMATION: Synthetic

<400> SEQUENCE: 185

gaaatagttt tgacacagag tcccggcaca ctgtcactct ctcccgggga aagagccacc     60

ttgtcatgta gagcaagtca gtcagtctct agctcttatc tcgcctggta ccagcagaag    120

ccgggacagg cccctagact gctgatctac ggggcaagtt ccagggccac cggaatcccc    180

gaccggttca gtggaagcgg aagcggaacc gattttactt tgacgatttc tagactggag    240

ccagaggatt tcgccgttta ctattgtcaa cagtacggaa gcagcccgtg gacgtttggc    300

cagggcacga aggtagaaat caag                                           324


<210> SEQ ID NO 186
<211> LENGTH: 108
<212> TYPE: PRT
<213> ORGANISM: Artificial Sequence
<220> FEATURE:
<223> OTHER INFORMATION: Synthetic

<400> SEQUENCE: 186

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105


<210> SEQ ID NO 187
<211> LENGTH: 21
<212> TYPE: DNA
<213> ORGANISM: Artificial Sequence
<220> FEATURE:
<223> OTHER INFORMATION: Synthetic

<400> SEQUENCE: 187

cagtcagtct ctagctctta t                                               21


<210> SEQ ID NO 188
<211> LENGTH: 7
<212> TYPE: PRT
<213> ORGANISM: Artificial Sequence
<220> FEATURE:
<223> OTHER INFORMATION: Synthetic

<400> SEQUENCE: 188
```

```
Gln Ser Val Ser Ser Ser Tyr
1               5


<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189

ggggcaagt                                                              9


<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Gly Ala Ser
1


<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191

caacagtacg gaagcagccc gtggacg                                         27


<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Gln Gln Tyr Gly Ser Ser Pro Trp Thr
1               5


<210> SEQ ID NO 193
<211> LENGTH: 363
<212> TYPE: DNA
<213> ORGANISM: Artificial Sequence
<220> FEATURE:
<223> OTHER INFORMATION: Synthetic

<400> SEQUENCE: 193

gaggtgcagc tggtggagtc tgggggaggt gtggtacggc ctgggggggtc cctgagactc     60

tcctgtacag cctctggatt cacctttgat gattatggca tgagctgggt ccgccaagct    120

ccagggaagg ggctggagtg gatctctggt attggttgga ctggtggtcg gtcaagttat    180

gcagactctg tgaggggccg attcaccatc tccagagaca acgccaagaa ttccctgtat    240

ctgcaaatga acagtctggg agccgaggac acggccttgt attattgtgc aagagatcgg    300

cagtggctgg tgcagtggta ctttgactac tggggccagg gaaccctggt caccgtctcc    360

tca                                                                  363


<210> SEQ ID NO 194
```

<211> LENGTH: 121
<212> TYPE: PRT
<213> ORGANISM: Artificial Sequence
<220> FEATURE:
<223> OTHER INFORMATION: Synthetic

<400> SEQUENCE: 194

```
Glu Val Gln Leu Val Glu Ser Gly Gly Gly Val Val Arg Pro Gly Gly
1               5                   10                  15

Ser Leu Arg Leu Ser Cys Thr Ala Ser Gly Phe Thr Phe Asp Asp Tyr
            20                  25                  30

Gly Met Ser Trp Val Arg Gln Ala Pro Gly Lys Gly Leu Glu Trp Ile
        35                  40                  45

Ser Gly Ile Gly Trp Thr Gly Gly Arg Ser Ser Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Gly Ala Glu Asp Thr Ala Leu Tyr Tyr Cys
                85                  90                  95

Ala Arg Asp Arg Gln Trp Leu Val Gln Trp Tyr Phe Asp Tyr Trp Gly
            100                 105                 110

Gln Gly Thr Leu Val Thr Val Ser Ser
        115                 120
```

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195
ggattcacct ttgatgatta tggc 24

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

```
Gly Phe Thr Phe Asp Asp Tyr Gly
1               5
```

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
attggttgga ctggtggtcg gtca 24

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

```
Ile Gly Trp Thr Gly Gly Arg Ser
1               5


<210> SEQ ID NO 199
<211> LENGTH: 42
<212> TYPE: DNA
<213> ORGANISM: Artificial Sequence
<220> FEATURE:
<223> OTHER INFORMATION: Synthetic

<400> SEQUENCE: 199

gcaagagatc ggcagtggct ggtgcagtgg tactttgact ac                          42


<210> SEQ ID NO 200
<211> LENGTH: 14
<212> TYPE: PRT
<213> ORGANISM: Artificial Sequence
<220> FEATURE:
<223> OTHER INFORMATION: Synthetic

<400> SEQUENCE: 200

Ala Arg Asp Arg Gln Trp Leu Val Gln Trp Tyr Phe Asp Tyr
1               5                   10


<210> SEQ ID NO 201
<211> LENGTH: 324
<212> TYPE: DNA
<213> ORGANISM: Artificial Sequence
<220> FEATURE:
<223> OTHER INFORMATION: Synthetic

<400> SEQUENCE: 201

gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccgtca    180

aggttcagtg gcagtggatc tgggacagat ttcactctca ccatcagcag tctgcaacct    240

gaagattttg caacttacta ctgtcaacag agttacagta cccctccgat caccttcggc    300

caagggacac gactggagat taaa                                           324


<210> SEQ ID NO 202
<211> LENGTH: 108
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
```

100 105

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
cagagcatta gcagctat 18

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Ser Ile Ser Ser Tyr
1 5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 gctgcatcc 9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Ala Ala Ser
1

<210> SEQ ID NO 207
<211> LENGTH: 30
<212> TYPE: DNA
<213> ORGANISM: Artificial Sequence
<220> FEATURE:
<223> OTHER INFORMATION: Synthetic

<400> SEQUENCE: 207
caacagagtt acagtacccc tccgatcacc 30

<210> SEQ ID NO 208
<211> LENGTH: 10
<212> TYPE: PRT
<213> ORGANISM: Artificial Sequence
<220> FEATURE:
<223> OTHER INFORMATION: Synthetic

<400> SEQUENCE: 208

Gln Gln Ser Tyr Ser Thr Pro Pro Ile Thr
1 5 10

<210> SEQ ID NO 209

<211> LENGTH: 363
<212> TYPE: DNA
<213> ORGANISM: Artificial Sequence
<220> FEATURE:
<223> OTHER INFORMATION: Synthetic

<400> SEQUENCE: 209
gaggtgcagc tggtggagtc tgggggaaga gtggtacggc cggggggggtc cctgagactc 60 tcctgtgcag cctctggatt cacttttgat gactatggca tgagttgggt ccgccaactt 120
ccagggaagg gcctggagtg ggtcgcaggt attagttgga atgatggtaa gacagtttat 180
gcagagtctg tgaagggccg attcatcatc tccagagaca acgccaagaa ctccctgcat 240
ctggagatga acagtctgag agccgaggac acggccttat attactgtgc gcgagattgg 300
caatacttaa tagatcgtta ctttgacttc tggggtcagg gaaccctggt caccgtctcc 360
tca 363

<210> SEQ ID NO 210
<211> LENGTH: 121
<212> TYPE: PRT
<213> ORGANISM: Artificial Sequence
<220> FEATURE:
<223> OTHER INFORMATION: Synthetic

<400> SEQUENCE: 210

Glu Val Gln Leu Val Glu Ser Gly Gly Arg Val Val Arg Pro Gly Gly
1 5 10 15

Ser Leu Arg Leu Ser Cys Ala Ala Ser Gly Phe Thr Phe Asp Asp Tyr
20 25 30

Gly Met Ser Trp Val Arg Gln Leu Pro Gly Lys Gly Leu Glu Trp Val
35 40 45

Ala Gly Ile Ser Trp Asn Asp Gly Lys Thr Val Tyr Ala Glu Ser Val
50 55 60

Lys Gly Arg Phe Ile Ile Ser Arg Asp Asn Ala Lys Asn Ser Leu His
65 70 75 80

Leu Glu Met Asn Ser Leu Arg Ala Glu Asp Thr Ala Leu Tyr Tyr Cys
85 90 95

Ala Arg Asp Trp Gln Tyr Leu Ile Asp Arg Tyr Phe Asp Phe Trp Gly
100 105 110

Gln Gly Thr Leu Val Thr Val Ser Ser
115 120

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211
ggattcactt ttgatgacta tggc 24

<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Gly Phe Thr Phe Asp Asp Tyr Gly 1 5

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213
attagttgga atgatggtaa gaca 24

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Ile Ser Trp Asn Asp Gly Lys Thr
1 5

<210> SEQ ID NO 215
<211> LENGTH: 42
<212> TYPE: DNA
<213> ORGANISM: Artificial Sequence
<220> FEATURE:
<223> OTHER INFORMATION: Synthetic

<400> SEQUENCE: 215
gcgcgagatt ggcaatactt aatagatcgt tactttgact tc 42

<210> SEQ ID NO 216
<211> LENGTH: 14
<212> TYPE: PRT
<213> ORGANISM: Artificial Sequence
<220> FEATURE:
<223> OTHER INFORMATION: Synthetic

<400> SEQUENCE: 216

Ala Arg Asp Trp Gln Tyr Leu Ile Asp Arg Tyr Phe Asp Phe
1 5 10

<210> SEQ ID NO 217
<211> LENGTH: 363
<212> TYPE: DNA
<213> ORGANISM: Artificial Sequence
<220> FEATURE:
<223> OTHER INFORMATION: Synthetic

<400> SEQUENCE: 217
gaagtgcagc tggtggagtc tgggggaggc ttggtgcagc ctggcgggtc cctgagactc 60
tcctgtgcag cctctggatt cacctttgat gattatgcca tgcactgggt ccggcaagct 120
ccagggaagg gcctggagtg ggtctcaggt attggttgga gtagtggtag cataggctat 180
gcggactctg tgaagggccg attcaccatc tccagagaca acgccaagaa ctccttgtat 240
ctgcaaatgg acagtctgag acctgaggac tcagccttat attactgtgc aaaagcctat 300
acatttatga ttaccctcta ctttgactac tggggccagg gaaccctggt caccgtctcc 360
tca 363

<210> SEQ ID NO 218
<211> LENGTH: 121

<212> TYPE: PRT
<213> ORGANISM: Artificial Sequence
<220> FEATURE:
<223> OTHER INFORMATION: Synthetic

<400> SEQUENCE: 218

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Gly Trp Ser Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Pro Glu Asp Ser Ala Leu Tyr Tyr Cys
                85                  90                  95

Ala Lys Ala Tyr Thr Phe Met Ile Thr Leu Tyr Phe Asp Tyr Trp Gly
            100                 105                 110

Gln Gly Thr Leu Val Thr Val Ser Ser
        115                 120
```

<210> SEQ ID NO 219
<211> LENGTH: 24
<212> TYPE: DNA
<213> ORGANISM: Artificial Sequence
<220> FEATURE:
<223> OTHER INFORMATION: Synthetic

<400> SEQUENCE: 219
ggattcacct ttgatgatta tgcc 24

<210> SEQ ID NO 220
<211> LENGTH: 8
<212> TYPE: PRT
<213> ORGANISM: Artificial Sequence
<220> FEATURE:
<223> OTHER INFORMATION: Synthetic

<400> SEQUENCE: 220

```
Gly Phe Thr Phe Asp Asp Tyr Ala
1               5
```

<210> SEQ ID NO 221
<211> LENGTH: 24
<212> TYPE: DNA
<213> ORGANISM: Artificial Sequence
<220> FEATURE:
<223> OTHER INFORMATION: Synthetic

<400> SEQUENCE: 221
attggttgga gtagtggtag cata 24

<210> SEQ ID NO 222
<211> LENGTH: 8
<212> TYPE: PRT
<213> ORGANISM: Artificial Sequence
<220> FEATURE:
<223> OTHER INFORMATION: Synthetic

<400> SEQUENCE: 222

```
Ile Gly Trp Ser Ser Gly Ser Ile
```

1 5

<210> SEQ ID NO 223
<211> LENGTH: 42
<212> TYPE: DNA
<213> ORGANISM: Artificial Sequence
<220> FEATURE:
<223> OTHER INFORMATION: Synthetic

<400> SEQUENCE: 223
gcaaaagcct atacatttat gattaccctc tactttgact ac 42

<210> SEQ ID NO 224
<211> LENGTH: 14
<212> TYPE: PRT
<213> ORGANISM: Artificial Sequence
<220> FEATURE:
<223> OTHER INFORMATION: Synthetic

<400> SEQUENCE: 224

Ala Lys Ala Tyr Thr Phe Met Ile Thr Leu Tyr Phe Asp Tyr
1 5 10

<210> SEQ ID NO 225
<211> LENGTH: 363
<212> TYPE: DNA
<213> ORGANISM: Artificial Sequence
<220> FEATURE:
<223> OTHER INFORMATION: Synthetic

<400> SEQUENCE: 225
gaagtgcagc tggtggagtc tgggggaggc ttggtacagc ctggcaggtc cctgagactc 60
tcctgtgcag cctctggatt cacctttgat gattatgaca tgcactgggt ccggcaagct 120
ccagggaagg gcctggagtg ggtgtcaggg agtggttgga ataggggtag tttaggctat 180
gcggattctg tgaagggccg attcaccatc tccagagaca acgccaagaa gtccctgtat 240
ctgcaaatga acagtgtgag agttgaggac acggccttgt attactgtgc aaaaggcttt 300
gtagtggtat cagctgctta ctttgactac tggggccagg gaaccctggt caccgtctcc 360
tca 363

<210> SEQ ID NO 226
<211> LENGTH: 121
<212> TYPE: PRT
<213> ORGANISM: Artificial Sequence
<220> FEATURE:
<223> OTHER INFORMATION: Synthetic

<400> SEQUENCE: 226

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Asp Met His Trp Val Arg Gln Ala Pro Gly Lys Gly Leu Glu Trp Val
35 40 45

Ser Gly Ser Gly Trp Asn Arg Gly Ser Leu Gly Tyr Ala Asp Ser Val
50 55 60

Lys Gly Arg Phe Thr Ile Ser Arg Asp Asn Ala Lys Lys Ser Leu Tyr
65 70 75 80

Leu Gln Met Asn Ser Val Arg Val Glu Asp Thr Ala Leu Tyr Tyr Cys
85 90 95

```
Ala Lys Gly Phe Val Val Val Ser Ala Ala Tyr Phe Asp Tyr Trp Gly
            100                 105                 110

Gln Gly Thr Leu Val Thr Val Ser Ser
        115                 120
```

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227

```
ggattcacct ttgatgatta tgac                                            24
```

<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

```
Gly Phe Thr Phe Asp Asp Tyr Asp
1               5
```

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229

```
agtggttgga ataggggtag ttta                                            24
```

<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

```
Ser Gly Trp Asn Arg Gly Ser Leu
1               5
```

<210> SEQ ID NO 231
<211> LENGTH: 42
<212> TYPE: DNA
<213> ORGANISM: Artificial Sequence
<220> FEATURE:
<223> OTHER INFORMATION: Synthetic

<400> SEQUENCE: 231

```
gcaaaaggct ttgtagtggt atcagctgct tactttgact ac                        42
```

<210> SEQ ID NO 232
<211> LENGTH: 14
<212> TYPE: PRT
<213> ORGANISM: Artificial Sequence
<220> FEATURE:
<223> OTHER INFORMATION: Synthetic

<400> SEQUENCE: 232

```
Ala Lys Gly Phe Val Val Val Ser Ala Ala Tyr Phe Asp Tyr
```

1 5 10

<210> SEQ ID NO 233
<211> LENGTH: 363
<212> TYPE: DNA
<213> ORGANISM: Artificial Sequence
<220> FEATURE:
<223> OTHER INFORMATION: Synthetic

<400> SEQUENCE: 233
caggtgcagc tggtgcagtc tggggctgag gtgaagaggc ctgggtcctc ggtgaaggtc 60
tcctgcaagg tatctggagt caccttcagg aattttgcta tcatctgggt gcgacaggcc 120
cctggacaag ggcttgagtg gatgggagga atcatccctt tctttagtgc agcaaattac 180
gcacagagct tccagggcag agtcacgatt accccggacg aatccacgag cacagccttc 240
atggagctgg ccagtctgag atctgaggac acggccgttt attattgtgc gagagagggg 300
gaacgtggac acacctatgg gtttgactac tggggccagg gaaccctggt caccgtctcc 360
tca 363

<210> SEQ ID NO 234
<211> LENGTH: 121
<212> TYPE: PRT
<213> ORGANISM: Artificial Sequence
<220> FEATURE:
<223> OTHER INFORMATION: Synthetic

<400> SEQUENCE: 234

Gln Val Gln Leu Val Gln Ser Gly Ala Glu Val Lys Arg Pro Gly Ser
1 5 10 15

Ser Val Lys Val Ser Cys Lys Val Ser Gly Val Thr Phe Arg Asn Phe
20 25 30

Ala Ile Ile Trp Val Arg Gln Ala Pro Gly Gln Gly Leu Glu Trp Met
35 40 45

Gly Gly Ile Ile Pro Phe Phe Ser Ala Ala Asn Tyr Ala Gln Ser Phe
50 55 60

Gln Gly Arg Val Thr Ile Thr Pro Asp Glu Ser Thr Ser Thr Ala Phe
65 70 75 80

Met Glu Leu Ala Ser Leu Arg Ser Glu Asp Thr Ala Val Tyr Tyr Cys
85 90 95

Ala Arg Glu Gly Glu Arg Gly His Thr Tyr Gly Phe Asp Tyr Trp Gly
100 105 110

Gln Gly Thr Leu Val Thr Val Ser Ser
115 120

<210> SEQ ID NO 235
<211> LENGTH: 24
<212> TYPE: DNA
<213> ORGANISM: Artificial Sequence
<220> FEATURE:
<223> OTHER INFORMATION: Synthetic

<400> SEQUENCE: 235
ggagtcacct tcaggaattt tgct 24

<210> SEQ ID NO 236
<211> LENGTH: 8
<212> TYPE: PRT
<213> ORGANISM: Artificial Sequence
<220> FEATURE:
<223> OTHER INFORMATION: Synthetic

<400> SEQUENCE: 236

Gly Val Thr Phe Arg Asn Phe Ala
1 5

<210> SEQ ID NO 237
<211> LENGTH: 24
<212> TYPE: DNA
<213> ORGANISM: Artificial Sequence
<220> FEATURE:
<223> OTHER INFORMATION: Synthetic

<400> SEQUENCE: 237
atcatccctt tctttagtgc agca 24

<210> SEQ ID NO 238
<211> LENGTH: 8
<212> TYPE: PRT
<213> ORGANISM: Artificial Sequence
<220> FEATURE:
<223> OTHER INFORMATION: Synthetic

<400> SEQUENCE: 238

Ile Ile Pro Phe Phe Ser Ala Ala
1 5

<210> SEQ ID NO 239
<211> LENGTH: 42
<212> TYPE: DNA
<213> ORGANISM: Artificial Sequence
<220> FEATURE:
<223> OTHER INFORMATION: Synthetic

<400> SEQUENCE: 239
gcgagagagg gggaacgtgg acacacctat gggtttgact ac 42

<210> SEQ ID NO 240
<211> LENGTH: 14
<212> TYPE: PRT
<213> ORGANISM: Artificial Sequence
<220> FEATURE:
<223> OTHER INFORMATION: Synthetic

<400> SEQUENCE: 240

Ala Arg Glu Gly Glu Arg Gly His Thr Tyr Gly Phe Asp Tyr
1 5 10

<210> SEQ ID NO 241
<211> LENGTH: 363
<212> TYPE: DNA
<213> ORGANISM: Artificial Sequence
<220> FEATURE:
<223> OTHER INFORMATION: Synthetic

<400> SEQUENCE: 241
gaagtgcagc tggtggagtc tgggggaggc ttggtacagt ctggcaggtc cctgagactc 60
tcctgtgcag cctctggatt cacctttgat gattatgcca tgcactgggt ccgacaacct 120
ccagggaagg gcctggaatg ggtctcaggt attaactgga atagaggtag gacaggctat 180
gcggactctg tgaagggccg attcaccatc tccagagaca acgccaagaa ctccctgtat 240
ctgcaaatga acgatctgag agttgaggat acggccttgt attactgtgc aaaagccgaa 300
cagtggctgg acgagggata ctttgactac tggggccagg gaaccctggt caccgtctcc 360
tca 363

<210> SEQ ID NO 242
<211> LENGTH: 121
<212> TYPE: PRT
<213> ORGANISM: Artificial Sequence
<220> FEATURE:
<223> OTHER INFORMATION: Synthetic

<400> SEQUENCE: 242

```
Glu Val Gln Leu Val Glu Ser Gly Gly Gly Leu Val Gln Ser Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Pro Pro Gly Lys Gly Leu Glu Trp Val
        35                  40                  45

Ser Gly Ile Asn Trp Asn Arg Gly Arg Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Asp Leu Arg Val Glu Asp Thr Ala Leu Tyr Tyr Cys
                85                  90                  95

Ala Lys Ala Glu Gln Trp Leu Asp Glu Gly Tyr Phe Asp Tyr Trp Gly
            100                 105                 110

Gln Gly Thr Leu Val Thr Val Ser Ser
        115                 120
```

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243

```
ggattcacct ttgatgatta tgcc                                            24
```

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

```
Gly Phe Thr Phe Asp Asp Tyr Ala
1               5
```

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245

```
attaactgga atagaggtag gaca                                            24
```

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Asn Trp Asn Arg Gly Arg Thr
1               5

<210> SEQ ID NO 247
<211> LENGTH: 42
<212> TYPE: DNA
<213> ORGANISM: Artificial Sequence
<220> FEATURE:
<223> OTHER INFORMATION: Synthetic

<400> SEQUENCE: 247
gcaaaagccg aacagtggct ggacgaggga tactttgact ac 42

<210> SEQ ID NO 248
<211> LENGTH: 14
<212> TYPE: PRT
<213> ORGANISM: Artificial Sequence
<220> FEATURE:
<223> OTHER INFORMATION: Synthetic

<400> SEQUENCE: 248

Ala Lys Ala Glu Gln Trp Leu Asp Glu Gly Tyr Phe Asp Tyr
1               5                   10

<210> SEQ ID NO 249
<211> LENGTH: 363
<212> TYPE: DNA
<213> ORGANISM: Artificial Sequence
<220> FEATURE:
<223> OTHER INFORMATION: Synthetic

<400> SEQUENCE: 249
gaggtgcagc tggtggagtc tgggggaggc ttggtgcagc gggggggggtc cctgagactc 60 tcctgtgcag cctctggatt cagctttagc agctatgcca tgaactgggt ccgccaggct 120
ccagggaagg ggctggagtg ggtctcaact attagtgata gtggtggtag tacatactac 180
gcagactccg tgaagggccg gttcaccatt tccagagaca attccaagaa cacgctgtct 240
ctgcaaatga acagcctgag agccgaggac acggccgtat attactgtgc gaaagatcag 300
ggtgggagtt acccctacta ctttcactac tggggccagg gaaccctggt caccgtctcc 360
tca 363

<210> SEQ ID NO 250
<211> LENGTH: 121
<212> TYPE: PRT
<213> ORGANISM: Artificial Sequence
<220> FEATURE:
<223> OTHER INFORMATION: Synthetic

<400> SEQUENCE: 250

Glu Val Gln Leu Val Glu Ser Gly Gly Gly Leu Val Gln Arg Gly Gly
1               5                   10                  15

Ser Leu Arg Leu Ser Cys Ala Ala Ser Gly Phe Ser Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Asp Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Ser
65                  70                  75                  80

```
Leu Gln Met Asn Ser Leu Arg Ala Glu Asp Thr Ala Val Tyr Tyr Cys
                85                  90                  95

Ala Lys Asp Gln Gly Gly Ser Tyr Pro Tyr Tyr Phe His Tyr Trp Gly
            100                 105                 110

Gln Gly Thr Leu Val Thr Val Ser Ser
        115                 120


<210> SEQ ID NO 251
<211> LENGTH: 24
<212> TYPE: DNA
<213> ORGANISM: Artificial Sequence
<220> FEATURE:
<223> OTHER INFORMATION: Synthetic

<400> SEQUENCE: 251

ggattcagct ttagcagcta tgcc                                            24


<210> SEQ ID NO 252
<211> LENGTH: 8
<212> TYPE: PRT
<213> ORGANISM: Artificial Sequence
<220> FEATURE:
<223> OTHER INFORMATION: Synthetic

<400> SEQUENCE: 252

Gly Phe Ser Phe Ser Ser Tyr Ala
1               5


<210> SEQ ID NO 253
<211> LENGTH: 24
<212> TYPE: DNA
<213> ORGANISM: Artificial Sequence
<220> FEATURE:
<223> OTHER INFORMATION: Synthetic

<400> SEQUENCE: 253

attagtgata gtggtggtag taca                                            24


<210> SEQ ID NO 254
<211> LENGTH: 8
<212> TYPE: PRT
<213> ORGANISM: Artificial Sequence
<220> FEATURE:
<223> OTHER INFORMATION: Synthetic

<400> SEQUENCE: 254

Ile Ser Asp Ser Gly Gly Ser Thr
1               5


<210> SEQ ID NO 255
<211> LENGTH: 42
<212> TYPE: DNA
<213> ORGANISM: Artificial Sequence
<220> FEATURE:
<223> OTHER INFORMATION: Synthetic

<400> SEQUENCE: 255

gcgaaagatc agggtgggag ttacccctac tactttcact ac                        42


<210> SEQ ID NO 256
<211> LENGTH: 14
<212> TYPE: PRT
<213> ORGANISM: Artificial Sequence
<220> FEATURE:
<223> OTHER INFORMATION: Synthetic
```

<400> SEQUENCE: 256

```
Ala Lys Asp Gln Gly Gly Ser Tyr Pro Tyr Tyr Phe His Tyr
1               5                   10
```

<210> SEQ ID NO 257
<211> LENGTH: 363
<212> TYPE: DNA
<213> ORGANISM: Artificial Sequence
<220> FEATURE:
<223> OTHER INFORMATION: Synthetic

<400> SEQUENCE: 257

```
gaagtgcagc tggtggagtc tgggggaggc ttggtacagc ctggcaggtc cctgagactc      60

tcctgtgcag cctctggatt cacctttgag gattatgcca tgcactgggt ccggcaagct     120

ccagggaagg gcctggagtg ggtctcaggt attggttgga gtaatgtaaa gataggctat     180

gcggactctg tgaagggccg attcaccatc tccagagaca atgtcaggaa ctccctatat     240

ctgcaaatga acagtctgag aactgaggac acggccttct attactgtgt aaaagcctat     300

acatctatgc ttaccctcta ctttgactat tggggccagg gaaccctggt caccgtctcc     360

tca                                                                   363
```

<210> SEQ ID NO 258
<211> LENGTH: 121
<212> TYPE: PRT
<213> ORGANISM: Artificial Sequence
<220> FEATURE:
<223> OTHER INFORMATION: Synthetic

<400> SEQUENCE: 258

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Glu Asp Tyr
            20                  25                  30

Ala Met His Trp Val Arg Gln Ala Pro Gly Lys Gly Leu Glu Trp Val
        35                  40                  45

Ser Gly Ile Gly Trp Ser Asn Val Lys Ile Gly Tyr Ala Asp Ser Val
    50                  55                  60

Lys Gly Arg Phe Thr Ile Ser Arg Asp Asn Val Arg Asn Ser Leu Tyr
65                  70                  75                  80

Leu Gln Met Asn Ser Leu Arg Thr Glu Asp Thr Ala Phe Tyr Tyr Cys
                85                  90                  95

Val Lys Ala Tyr Thr Ser Met Leu Thr Leu Tyr Phe Asp Tyr Trp Gly
            100                 105                 110

Gln Gly Thr Leu Val Thr Val Ser Ser
        115                 120
```

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259

```
ggattcacct ttgaggatta tgcc                                             24
```

<210> SEQ ID NO 260
<211> LENGTH: 8

<212> TYPE: PRT
<213> ORGANISM: Artificial Sequence
<220> FEATURE:
<223> OTHER INFORMATION: Synthetic

<400> SEQUENCE: 260

Gly Phe Thr Phe Glu Asp Tyr Ala
1 5

<210> SEQ ID NO 261
<211> LENGTH: 24
<212> TYPE: DNA
<213> ORGANISM: Artificial Sequence
<220> FEATURE:
<223> OTHER INFORMATION: Synthetic

<400> SEQUENCE: 261
attggttgga gtaatgtaaa gata 24

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Ile Gly Trp Ser Asn Val Lys Ile
1 5

<210> SEQ ID NO 263
<211> LENGTH: 42
<212> TYPE: DNA
<213> ORGANISM: Artificial Sequence
<220> FEATURE:
<223> OTHER INFORMATION: Synthetic

<400> SEQUENCE: 263
gtaaaagcct atacatctat gcttaccctc tactttgact at 42

<210> SEQ ID NO 264
<211> LENGTH: 14
<212> TYPE: PRT
<213> ORGANISM: Artificial Sequence
<220> FEATURE:
<223> OTHER INFORMATION: Synthetic

<400> SEQUENCE: 264

Val Lys Ala Tyr Thr Ser Met Leu Thr Leu Tyr Phe Asp Tyr
1 5 10

<210> SEQ ID NO 265
<211> LENGTH: 354
<212> TYPE: DNA
<213> ORGANISM: Artificial Sequence
<220> FEATURE:
<223> OTHER INFORMATION: Synthetic

<400> SEQUENCE: 265
caggtgcagc tggtgcagtc tggggctgag gtgaagaggc ctggggcctc agtgaaggtt 60
tcctgcaagg catctggata caccttcacc agcttctata tgtactgggt gcgacaggcc 120
cctggacaag ggcttgagtg gatgggaata atcaacccta gtgatggtag cacaagcaac 180
gcacagaagt tccagggcag agtcaccatg accagggaca cgtccacgag tacagtctac 240
atggagctga gcagcctgag atctgaggac acggccgtgt attactgtgc gagacgggtg 300
gctggggata tttttgatat ctggggccaa gggacaatgg tcaccgtctc ttca 354

<210> SEQ ID NO 266
<211> LENGTH: 118
<212> TYPE: PRT
<213> ORGANISM: Artificial Sequence
<220> FEATURE:
<223> OTHER INFORMATION: Synthetic

<400> SEQUENCE: 266

Gln Val Gln Leu Val Gln Ser Gly Ala Glu Val Lys Arg Pro Gly Ala
1 5 10 15

Ser Val Lys Val Ser Cys Lys Ala Ser Gly Tyr Thr Phe Thr Ser Phe
20 25 30

Tyr Met Tyr Trp Val Arg Gln Ala Pro Gly Gln Gly Leu Glu Trp Met
35 40 45

Gly Ile Ile Asn Pro Ser Asp Gly Ser Thr Ser Asn Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Arg Val Ala Gly Asp Ile Phe Asp Ile Trp Gly Gln Gly Thr
100 105 110

Met Val Thr Val Ser Ser
115

<210> SEQ ID NO 267
<211> LENGTH: 24
<212> TYPE: DNA
<213> ORGANISM: Artificial Sequence
<220> FEATURE:
<223> OTHER INFORMATION: Synthetic

<400> SEQUENCE: 267
ggatacacct tcaccagctt ctat 24

<210> SEQ ID NO 268
<211> LENGTH: 8
<212> TYPE: PRT
<213> ORGANISM: Artificial Sequence
<220> FEATURE:
<223> OTHER INFORMATION: Synthetic

<400> SEQUENCE: 268

Gly Tyr Thr Phe Thr Ser Phe Tyr
1 5

<210> SEQ ID NO 269
<211> LENGTH: 24
<212> TYPE: DNA
<213> ORGANISM: Artificial Sequence
<220> FEATURE:
<223> OTHER INFORMATION: Synthetic

<400> SEQUENCE: 269
atcaacccta gtgatggtag caca 24

<210> SEQ ID NO 270
<211> LENGTH: 8
<212> TYPE: PRT
<213> ORGANISM: Artificial Sequence

```
<220> FEATURE:
<223> OTHER INFORMATION: Synthetic

<400> SEQUENCE: 270

Ile Asn Pro Ser Asp Gly Ser Thr
1               5


<210> SEQ ID NO 271
<211> LENGTH: 33
<212> TYPE: DNA
<213> ORGANISM: Artificial Sequence
<220> FEATURE:
<223> OTHER INFORMATION: Synthetic

<400> SEQUENCE: 271

gcgagacggg tggctgggga tatttttgat atc                                    33


<210> SEQ ID NO 272
<211> LENGTH: 11
<212> TYPE: PRT
<213> ORGANISM: Artificial Sequence
<220> FEATURE:
<223> OTHER INFORMATION: Synthetic

<400> SEQUENCE: 272

Ala Arg Arg Val Ala Gly Asp Ile Phe Asp Ile
1               5                   10


<210> SEQ ID NO 273
<211> LENGTH: 357
<212> TYPE: DNA
<213> ORGANISM: Artificial Sequence
<220> FEATURE:
<223> OTHER INFORMATION: Synthetic

<400> SEQUENCE: 273

caggtgcagc tgcaggagtc gggcccagga ctggtgaagc cttcggagac cctgtccctc      60

acctgcactg tctctggtgg ctccatcagt agttaccact ggaactggat ccggcagagt     120

ccagggaagg gactggaatg gattggatat atctattata ttgggagcac cgactataat     180

ccctccctcg agagtcgagt caccatatca gtagacacgt ccaagaacca gttctccctg     240

aagctgagtt ctgtgaccgc tgcggacacg gccgtgtatt actgtgcgag agtccccgtg     300

ggagctacag ggcttctga tgtctggggc caagggacaa tggtcaccgt ctcttca         357


<210> SEQ ID NO 274
<211> LENGTH: 119
<212> TYPE: PRT
<213> ORGANISM: Artificial Sequence
<220> FEATURE:
<223> OTHER INFORMATION: Synthetic

<400> SEQUENCE: 274

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

His Trp Asn Trp Ile Arg Gln Ser Pro Gly Lys Gly Leu Glu Trp Ile
        35                  40                  45

Gly Tyr Ile Tyr Tyr Ile Gly Ser Thr Asp Tyr Asn Pro Ser Leu Glu
    50                  55                  60

Ser Arg Val Thr Ile Ser Val Asp Thr Ser Lys Asn Gln Phe Ser Leu
65                  70                  75                  80
```

```
Lys Leu Ser Ser Val Thr Ala Ala Asp Thr Ala Val Tyr Tyr Cys Ala
                85                  90                  95

Arg Val Pro Val Gly Ala Thr Gly Ala Ser Asp Val Trp Gly Gln Gly
            100                 105                 110

Thr Met Val Thr Val Ser Ser
        115


<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275

ggtggctcca tcagtagtta ccac                                            24


<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

Gly Gly Ser Ile Ser Ser Tyr His
1               5


<210> SEQ ID NO 277
<211> LENGTH: 21
<212> TYPE: DNA
<213> ORGANISM: Artificial Sequence
<220> FEATURE:
<223> OTHER INFORMATION: Synthetic

<400> SEQUENCE: 277

atctattata ttgggagcac c                                               21


<210> SEQ ID NO 278
<211> LENGTH: 7
<212> TYPE: PRT
<213> ORGANISM: Artificial Sequence
<220> FEATURE:
<223> OTHER INFORMATION: Synthetic

<400> SEQUENCE: 278

Ile Tyr Tyr Ile Gly Ser Thr
1               5


<210> SEQ ID NO 279
<211> LENGTH: 39
<212> TYPE: DNA
<213> ORGANISM: Artificial Sequence
<220> FEATURE:
<223> OTHER INFORMATION: Synthetic

<400> SEQUENCE: 279

gcgagagtcc ccgtgggagc tacaggggct tctgatgtc                            39


<210> SEQ ID NO 280
<211> LENGTH: 13
<212> TYPE: PRT
<213> ORGANISM: Artificial Sequence
<220> FEATURE:
<223> OTHER INFORMATION: Synthetic
```

<400> SEQUENCE: 280

Ala Arg Val Pro Val Gly Ala Thr Gly Ala Ser Asp Val
1 5 10

<210> SEQ ID NO 281
<211> LENGTH: 363
<212> TYPE: DNA
<213> ORGANISM: Artificial Sequence
<220> FEATURE:
<223> OTHER INFORMATION: Synthetic

<400> SEQUENCE: 281
gaggtgcagc tggtggagtc tgggggaagt gtggttcgac ctgggggtc cctgagactc 60 tcctgtgtag tctctggatt cacctttgag gattatggtt tgagctgggt ccgccaaatt 120
ccagggaaag gactggagtg ggtctctggt attagttgga ctggtggtaa cacaggttat 180
gcagactctg tgaagggccg cttcaccatc tccagagaca acgccaagaa ctccctgtat 240
ctgcaaatga acagtctgag agccgaagac acggccctgt atcactgtac gagagatcga 300
cagtggctga tgcagtggta ttttgactat tggggccagg gaaccctggt caccgtctcc 360
tca 363

<210> SEQ ID NO 282
<211> LENGTH: 121
<212> TYPE: PRT
<213> ORGANISM: Artificial Sequence
<220> FEATURE:
<223> OTHER INFORMATION: Synthetic

<400> SEQUENCE: 282

Glu Val Gln Leu Val Glu Ser Gly Gly Ser Val Val Arg Pro Gly Gly
1 5 10 15

Ser Leu Arg Leu Ser Cys Val Val Ser Gly Phe Thr Phe Glu Asp Tyr
20 25 30

Gly Leu Ser Trp Val Arg Gln Ile Pro Gly Lys Gly Leu Glu Trp Val
35 40 45

Ser Gly Ile Ser Trp Thr Gly Gly Asn Thr Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr His Cys
85 90 95

Thr Arg Asp Arg Gln Trp Leu Met Gln Trp Tyr Phe Asp Tyr Trp Gly
100 105 110

Gln Gly Thr Leu Val Thr Val Ser Ser
115 120

<210> SEQ ID NO 283
<211> LENGTH: 24
<212> TYPE: DNA
<213> ORGANISM: Artificial Sequence
<220> FEATURE:
<223> OTHER INFORMATION: Synthetic

<400> SEQUENCE: 283
ggattcacct ttgaggatta tggt 24

<210> SEQ ID NO 284
<211> LENGTH: 8

<212> TYPE: PRT
<213> ORGANISM: Artificial Sequence
<220> FEATURE:
<223> OTHER INFORMATION: Synthetic

<400> SEQUENCE: 284

Gly Phe Thr Phe Glu Asp Tyr Gly
1               5

<210> SEQ ID NO 285
<211> LENGTH: 24
<212> TYPE: DNA
<213> ORGANISM: Artificial Sequence
<220> FEATURE:
<223> OTHER INFORMATION: Synthetic

<400> SEQUENCE: 285
attagttgga ctggtggtaa caca 24

<210> SEQ ID NO 286
<211> LENGTH: 8
<212> TYPE: PRT
<213> ORGANISM: Artificial Sequence
<220> FEATURE:
<223> OTHER INFORMATION: Synthetic

<400> SEQUENCE: 286

Ile Ser Trp Thr Gly Gly Asn Thr
1               5

<210> SEQ ID NO 287
<211> LENGTH: 42
<212> TYPE: DNA
<213> ORGANISM: Artificial Sequence
<220> FEATURE:
<223> OTHER INFORMATION: Synthetic

<400> SEQUENCE: 287
acgagagatc gacagtggct gatgcagtgg tattttgact at 42

<210> SEQ ID NO 288
<211> LENGTH: 14
<212> TYPE: PRT
<213> ORGANISM: Artificial Sequence
<220> FEATURE:
<223> OTHER INFORMATION: Synthetic

<400> SEQUENCE: 288

Thr Arg Asp Arg Gln Trp Leu Met Gln Trp Tyr Phe Asp Tyr
1               5                   10

<210> SEQ ID NO 289
<211> LENGTH: 357
<212> TYPE: DNA
<213> ORGANISM: Artificial Sequence
<220> FEATURE:
<223> OTHER INFORMATION: Synthetic

<400> SEQUENCE: 289
caggtgcagc tggtggagtc tgggggaggc gtggtccagc ctgggaggtc cctgagactc 60
tcctgttcag cctctggatt caccttcagt gcctatgcca tgcactgggt ccgccaggct 120
ccaggcaagg ggctggaatg ggtggcagct atctcatatg gtggaagtga taaatactat 180
gcagactccg tgaagggccg attcaccatc tccagagaca attccaagaa cacgctatat 240
ctgcaaatga acagcctgag aactgacgac acggctgtgt attactgtgc gaaatccgct 300
cactggaact tcttctttga ctactggggc cagggaaccc tggtcactgt ctcctca 357

<210> SEQ ID NO 290
<211> LENGTH: 119
<212> TYPE: PRT
<213> ORGANISM: Artificial Sequence
<220> FEATURE:
<223> OTHER INFORMATION: Synthetic

<400> SEQUENCE: 290

Gln Val Gln Leu Val Glu Ser Gly Gly Gly Val Val Gln Pro Gly Arg
1 5 10 15

Ser Leu Arg Leu Ser Cys Ser Ala Ser Gly Phe Thr Phe Ser Ala Tyr
20 25 30

Ala Met His Trp Val Arg Gln Ala Pro Gly Lys Gly Leu Glu Trp Val
35 40 45

Ala Ala Ile Ser Tyr Gly Gly Ser Asp Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Thr Asp Asp Thr Ala Val Tyr Tyr Cys
85 90 95

Ala Lys Ser Ala His Trp Asn Phe Phe Phe Asp Tyr Trp Gly Gln Gly
100 105 110

Thr Leu Val Thr Val Ser Ser
115

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggattcacct tcagtgccta tgcc 24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Gly Phe Thr Phe Ser Ala Tyr Ala
1 5

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
atctcatatg gtggaagtga taaa 24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

Ile Ser Tyr Gly Gly Ser Asp Lys
1               5

<210> SEQ ID NO 295
<211> LENGTH: 36
<212> TYPE: DNA
<213> ORGANISM: Artificial Sequence
<220> FEATURE:
<223> OTHER INFORMATION: Synthetic

<400> SEQUENCE: 295
gcgaaatccg ctcactggaa cttcttcttt gactac 36

<210> SEQ ID NO 296
<211> LENGTH: 12
<212> TYPE: PRT
<213> ORGANISM: Artificial Sequence
<220> FEATURE:
<223> OTHER INFORMATION: Synthetic

<400> SEQUENCE: 296

Ala Lys Ser Ala His Trp Asn Phe Phe Phe Asp Tyr
1               5                   10

<210> SEQ ID NO 297
<211> LENGTH: 363
<212> TYPE: DNA
<213> ORGANISM: Artificial Sequence
<220> FEATURE:
<223> OTHER INFORMATION: Synthetic

<400> SEQUENCE: 297
gaagtgcagc tggtggagtc tgggggaggc ttggtacagc ctggcaggtc cctgagactc 60
tcctgtgtag cctctggatt cgcccttcat gattatgcca tgcactgggt ccggcaagtt 120
ccagggaagg gcctggagtg ggtctcaagt attagttgga atagtggtgt cataggctat 180
gcggactctc tgaagggccg cttcaccatc tccagagaca acgccaagaa ctccctgtat 240
ctgcaaatga acagtctgag agcagaggac acggccttat actactgtgc aaaaggtagt 300
gggagctact acgtcagttg gttcgacccc tggggccagg gaaccctggt caccgtctcc 360
tca 363

<210> SEQ ID NO 298
<211> LENGTH: 121
<212> TYPE: PRT
<213> ORGANISM: Artificial Sequence
<220> FEATURE:
<223> OTHER INFORMATION: Synthetic

<400> SEQUENCE: 298

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Ala Leu His Asp Tyr
            20                  25                  30

Ala Met His Trp Val Arg Gln Val Pro Gly Lys Gly Leu Glu Trp Val
        35                  40                  45

Ser Ser Ile Ser Trp Asn Ser Gly Val Ile Gly Tyr Ala Asp Ser Leu
    50                  55                  60

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Ser Gly Ser Tyr Tyr Val Ser Trp Phe Asp Pro Trp Gly
            100                 105                 110

Gln Gly Thr Leu Val Thr Val Ser Ser
        115                 120


<210> SEQ ID NO 299
<211> LENGTH: 24
<212> TYPE: DNA
<213> ORGANISM: Artificial Sequence
<220> FEATURE:
<223> OTHER INFORMATION: Synthetic

<400> SEQUENCE: 299

ggattcgccc ttcatgatta tgcc                                            24


<210> SEQ ID NO 300
<211> LENGTH: 8
<212> TYPE: PRT
<213> ORGANISM: Artificial Sequence
<220> FEATURE:
<223> OTHER INFORMATION: Synthetic

<400> SEQUENCE: 300

Gly Phe Ala Leu His Asp Tyr Ala
1               5


<210> SEQ ID NO 301
<211> LENGTH: 24
<212> TYPE: DNA
<213> ORGANISM: Artificial Sequence
<220> FEATURE:
<223> OTHER INFORMATION: Synthetic

<400> SEQUENCE: 301

attagttgga atagtggtgt cata                                            24


<210> SEQ ID NO 302
<211> LENGTH: 8
<212> TYPE: PRT
<213> ORGANISM: Artificial Sequence
<220> FEATURE:
<223> OTHER INFORMATION: Synthetic

<400> SEQUENCE: 302

Ile Ser Trp Asn Ser Gly Val Ile
1               5


<210> SEQ ID NO 303
<211> LENGTH: 42
<212> TYPE: DNA
<213> ORGANISM: Artificial Sequence
<220> FEATURE:
<223> OTHER INFORMATION: Synthetic

<400> SEQUENCE: 303

gcaaaaggta gtgggagcta ctacgtcagt tggttcgacc cc                        42


<210> SEQ ID NO 304
<211> LENGTH: 14
<212> TYPE: PRT
<213> ORGANISM: Artificial Sequence
```

<220> FEATURE:
<223> OTHER INFORMATION: Synthetic

<400> SEQUENCE: 304

```
Ala Lys Gly Ser Gly Ser Tyr Tyr Val Ser Trp Phe Asp Pro
1               5                   10
```

<210> SEQ ID NO 305
<211> LENGTH: 369
<212> TYPE: DNA
<213> ORGANISM: Artificial Sequence
<220> FEATURE:
<223> OTHER INFORMATION: Synthetic

<400> SEQUENCE: 305

```
cagctgcagc tgcaggagtc gggcccagga ctggttcagc cttcggagac cctgtccctc     60

acctgcactg tctctggtga ctccatcagt agtactgctt accactggga ctggatccgc    120

cagcccccg ggaagggact ggagtggatt gggaccatca cttataatgg gaacacctac    180

ttcaacccgt ccctcaagag tcgagtcacc atatccgttg acacgtccaa gaaccagttc    240

tccctgaagc tactctctat gaccgccgca gaaacggctg ttttttactg tgcgcgacat    300

ctaggatata acagtgactt ctttcccttt gacttctggg gccagggaac cctggtcact    360

gtctcctca                                                            369
```

<210> SEQ ID NO 306
<211> LENGTH: 123
<212> TYPE: PRT
<213> ORGANISM: Artificial Sequence
<220> FEATURE:
<223> OTHER INFORMATION: Synthetic

<400> SEQUENCE: 306

```
Gln Leu Gln Leu Gln Glu Ser Gly Pro Gly Leu Val Gln Pro Ser Glu
1               5                   10                  15

Thr Leu Ser Leu Thr Cys Thr Val Ser Gly Asp Ser Ile Ser Ser Thr
            20                  25                  30

Ala Tyr His Trp Asp Trp Ile Arg Gln Pro Pro Gly Lys Gly Leu Glu
        35                  40                  45

Trp Ile Gly Thr Ile Thr Tyr Asn Gly Asn Thr Tyr Phe Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Leu Ser Met Thr Ala Ala Glu Thr Ala Val Phe Tyr
                85                  90                  95

Cys Ala Arg His Leu Gly Tyr Asn Ser Asp Phe Phe Pro Phe Asp Phe
            100                 105                 110

Trp Gly Gln Gly Thr Leu Val Thr Val Ser Ser
        115                 120
```

<210> SEQ ID NO 307
<211> LENGTH: 30
<212> TYPE: DNA
<213> ORGANISM: Artificial Sequence
<220> FEATURE:
<223> OTHER INFORMATION: Synthetic

<400> SEQUENCE: 307

```
ggtgactcca tcagtagtac tgcttaccac                                      30
```

<210> SEQ ID NO 308
<211> LENGTH: 10
<212> TYPE: PRT
<213> ORGANISM: Artificial Sequence
<220> FEATURE:
<223> OTHER INFORMATION: Synthetic

<400> SEQUENCE: 308

Gly Asp Ser Ile Ser Ser Thr Ala Tyr His
1 5 10

<210> SEQ ID NO 309
<211> LENGTH: 21
<212> TYPE: DNA
<213> ORGANISM: Artificial Sequence
<220> FEATURE:
<223> OTHER INFORMATION: Synthetic

<400> SEQUENCE: 309
atcacttata atgggaacac c 21

<210> SEQ ID NO 310
<211> LENGTH: 7
<212> TYPE: PRT
<213> ORGANISM: Artificial Sequence
<220> FEATURE:
<223> OTHER INFORMATION: Synthetic

<400> SEQUENCE: 310

Ile Thr Tyr Asn Gly Asn Thr
1 5

<210> SEQ ID NO 311
<211> LENGTH: 45
<212> TYPE: DNA
<213> ORGANISM: Artificial Sequence
<220> FEATURE:
<223> OTHER INFORMATION: Synthetic

<400> SEQUENCE: 311
gcgcgacatc taggatataa cagtgacttc tttccctttg acttc 45

<210> SEQ ID NO 312
<211> LENGTH: 15
<212> TYPE: PRT
<213> ORGANISM: Artificial Sequence
<220> FEATURE:
<223> OTHER INFORMATION: Synthetic

<400> SEQUENCE: 312

Ala Arg His Leu Gly Tyr Asn Ser Asp Phe Phe Pro Phe Asp Phe
1 5 10 15

<210> SEQ ID NO 313
<211> LENGTH: 357
<212> TYPE: DNA
<213> ORGANISM: Artificial Sequence
<220> FEATURE:
<223> OTHER INFORMATION: Synthetic

<400> SEQUENCE: 313
gaggtgcagc tggtggagtc tgggggaggc ctggtacggc cggggggtc cctgagactc 60 tcctgtgcag cctctggatt cacctttagc acctatgcca tggcctgggt ccgccagact 120
ccagggaagg ggctggaggg ggtctcagct attgggggta gtggtgatag tacctattat 180
gtcgactccg tgaagggccg gttcaccatc tccagggaca actccaagag cacgcttttt 240

```
ctgcaaatga atagcctgag agccgaggac acggccgttt attactgtgt gaaagtccgg    300

aattacgacg gttcttttga tatctggggc caagggacaa tggtcaccgt ctcttca       357


<210> SEQ ID NO 314
<211> LENGTH: 119
<212> TYPE: PRT
<213> ORGANISM: Artificial Sequence
<220> FEATURE:
<223> OTHER INFORMATION: Synthetic

<400> SEQUENCE: 314

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Thr Tyr
            20                  25                  30

Ala Met Ala Trp Val Arg Gln Thr Pro Gly Lys Gly Leu Glu Gly Val
        35                  40                  45

Ser Ala Ile Gly Gly Ser Gly Asp Ser Thr Tyr Tyr Val Asp Ser Val
    50                  55                  60

Lys Gly Arg Phe Thr Ile Ser Arg Asp Asn Ser Lys Ser Thr Leu Phe
65                  70                  75                  80

Leu Gln Met Asn Ser Leu Arg Ala Glu Asp Thr Ala Val Tyr Tyr Cys
                85                  90                  95

Val Lys Val Arg Asn Tyr Asp Gly Ser Phe Asp Ile Trp Gly Gln Gly
            100                 105                 110

Thr Met Val Thr Val Ser Ser
        115


<210> SEQ ID NO 315
<211> LENGTH: 24
<212> TYPE: DNA
<213> ORGANISM: Artificial Sequence
<220> FEATURE:
<223> OTHER INFORMATION: Synthetic

<400> SEQUENCE: 315

ggattcacct ttagcaccta tgcc                                            24


<210> SEQ ID NO 316
<211> LENGTH: 8
<212> TYPE: PRT
<213> ORGANISM: Artificial Sequence
<220> FEATURE:
<223> OTHER INFORMATION: Synthetic

<400> SEQUENCE: 316

Gly Phe Thr Phe Ser Thr Tyr Ala
1               5


<210> SEQ ID NO 317
<211> LENGTH: 24
<212> TYPE: DNA
<213> ORGANISM: Artificial Sequence
<220> FEATURE:
<223> OTHER INFORMATION: Synthetic

<400> SEQUENCE: 317

attgggggta gtggtgatag tacc                                            24


<210> SEQ ID NO 318
<211> LENGTH: 8
```

<212> TYPE: PRT
<213> ORGANISM: Artificial Sequence
<220> FEATURE:
<223> OTHER INFORMATION: Synthetic

<400> SEQUENCE: 318

Ile Gly Gly Ser Gly Asp Ser Thr
1               5

<210> SEQ ID NO 319
<211> LENGTH: 36
<212> TYPE: DNA
<213> ORGANISM: Artificial Sequence
<220> FEATURE:
<223> OTHER INFORMATION: Synthetic

<400> SEQUENCE: 319
gtgaaagtcc ggaattacga cggttctttt gatatc                              36

<210> SEQ ID NO 320
<211> LENGTH: 12
<212> TYPE: PRT
<213> ORGANISM: Artificial Sequence
<220> FEATURE:
<223> OTHER INFORMATION: Synthetic

<400> SEQUENCE: 320

Val Lys Val Arg Asn Tyr Asp Gly Ser Phe Asp Ile
1               5                   10

<210> SEQ ID NO 321
<211> LENGTH: 174
<212> TYPE: PRT
<213> ORGANISM: Artificial Sequence
<220> FEATURE:
<223> OTHER INFORMATION: hPD-1-MMH
<220> FEATURE:
<223> OTHER INFORMATION: 1-146: aa 25-170 of NP_005009.2 with C93S
<220> FEATURE:
<223> OTHER INFORMATION: 147-174: myc-myc-hexahistidine

<400> SEQUENCE: 321

Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Ser Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Thr
    130                 135                 140

Leu Val Glu Gln Lys Leu Ile Ser Glu Glu Asp Leu Gly Gly Glu Gln
145                 150                 155                 160

```
Lys Leu Ile Ser Glu Glu Asp Leu His His His His His His
                165                 170


<210> SEQ ID NO 322
<211> LENGTH: 174
<212> TYPE: PRT
<213> ORGANISM: Artificial Sequence
<220> FEATURE:
<223> OTHER INFORMATION: MfPD-1-MMH
<220> FEATURE:
<223> OTHER INFORMATION: 1-146: M.fascicularis PD-1 with C93S
<220> FEATURE:
<223> OTHER INFORMATION: 147-174: myc-myc-hexahistidine

<400> SEQUENCE: 322

Leu Glu Ser Pro Asp Arg Pro Trp Asn Pro Pro Thr Phe Ser Pro Ala
1               5                   10                  15

Leu Leu Leu Val Thr Glu Gly Asp Asn Ala Thr Phe Thr Cys Ser Phe
            20                  25                  30

Ser Asn Ala Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Arg Asp Ser Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Ala
    130                 135                 140

Leu Val Glu Gln Lys Leu Ile Ser Glu Glu Asp Leu Gly Gly Glu Gln
145                 150                 155                 160

Lys Leu Ile Ser Glu Glu Asp Leu His His His His His His
                165                 170


<210> SEQ ID NO 323
<211> LENGTH: 379
<212> TYPE: PRT
<213> ORGANISM: Artificial Sequence
<220> FEATURE:
<223> OTHER INFORMATION: hPD-1-mFc
<220> FEATURE:
<223> OTHER INFORMATION: 1-146: aa 25-170 of NP-005009.2 with C93S
<220> FEATURE:
<223> OTHER INFORMATION: 147-379: mFc: aa 98-330 of P01863

<400> SEQUENCE: 323

Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Ser Arg Phe Arg Val Thr Gln Leu Pro Asn Gly Arg
65                  70                  75                  80
```

```
Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Thr
    130                 135                 140

Leu Val Glu Pro Arg Gly Pro Thr Ile Lys Pro Cys Pro Pro Cys Lys
145                 150                 155                 160

Cys Pro Ala Pro Asn Leu Leu Gly Gly Pro Ser Val Phe Ile Phe Pro
                165                 170                 175

Pro Lys Ile Lys Asp Val Leu Met Ile Ser Leu Ser Pro Ile Val Thr
            180                 185                 190

Cys Val Val Val Asp Val Ser Glu Asp Asp Pro Asp Val Gln Ile Ser
        195                 200                 205

Trp Phe Val Asn Asn Val Glu Val His Thr Ala Gln Thr Gln Thr His
    210                 215                 220

Arg Glu Asp Tyr Asn Ser Thr Leu Arg Val Val Ser Ala Leu Pro Ile
225                 230                 235                 240

Gln His Gln Asp Trp Met Ser Gly Lys Glu Phe Lys Cys Lys Val Asn
                245                 250                 255

Asn Lys Asp Leu Pro Ala Pro Ile Glu Arg Thr Ile Ser Lys Pro Lys
            260                 265                 270

Gly Ser Val Arg Ala Pro Gln Val Tyr Val Leu Pro Pro Pro Glu Glu
        275                 280                 285

Glu Met Thr Lys Lys Gln Val Thr Leu Thr Cys Met Val Thr Asp Phe
    290                 295                 300

Met Pro Glu Asp Ile Tyr Val Glu Trp Thr Asn Asn Gly Lys Thr Glu
305                 310                 315                 320

Leu Asn Tyr Lys Asn Thr Glu Pro Val Leu Asp Ser Asp Gly Ser Tyr
                325                 330                 335

Phe Met Tyr Ser Lys Leu Arg Val Glu Lys Lys Asn Trp Val Glu Arg
            340                 345                 350

Asn Ser Tyr Ser Cys Ser Val Val His Glu Gly Leu His Asn His His
        355                 360                 365

Thr Thr Lys Ser Phe Ser Arg Thr Pro Gly Lys
    370                 375
```

<210> SEQ ID NO 324
<211> LENGTH: 373
<212> TYPE: PRT
<213> ORGANISM: Artificial Sequence
<220> FEATURE:
<223> OTHER INFORMATION: hPD-1-hFc
<220> FEATURE:
<223> OTHER INFORMATION: 1-146: aa 25-170 of NP_005009.2 with C93S
<220> FEATURE:
<223> OTHER INFORMATION: 147-373: hFc: aa 104-330 of P01857

<400> SEQUENCE: 324

```
Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45
```

```
Ser Asn Gln Thr Asp Lys Leu Ala Ala Phe Pro Glu Asp Arg Ser Gln
    50                  55                  60

Pro Gly Gln Asp Ser Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Thr
    130                 135                 140

Leu Val Asp Lys Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser His Glu Asp Pro Glu Val Lys Phe Asn Trp Tyr Val Asp Gly Val
        195                 200                 205

Glu Val His Asn Ala Lys Thr Lys Pro Arg Glu Glu Gln Tyr Asn Ser
    210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
                245                 250                 255

Pro Ile Glu Lys Thr Ile Ser Lys Ala Lys Gly Gln Pro Arg Glu Pro
            260                 265                 270

Gln Val Tyr Thr Leu Pro Pro Ser Arg Asp Glu Leu Thr Lys Asn Gln
        275                 280                 285

Val Ser Leu Thr Cys Leu Val Lys Gly Phe Tyr Pro Ser Asp Ile Ala
    290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Lys Leu
                325                 330                 335

Thr Val Asp Lys Ser Arg Trp Gln Gln Gly Asn Val Phe Ser Cys Ser
            340                 345                 350

Val Met His Glu Ala Leu His Asn His Tyr Thr Gln Lys Ser Leu Ser
        355                 360                 365

Leu Ser Pro Gly Lys
    370
```

<210> SEQ ID NO 325
<211> LENGTH: 448
<212> TYPE: PRT
<213> ORGANISM: Artificial Sequence
<220> FEATURE:
<223> OTHER INFORMATION: hPD-L1-hFc
<220> FEATURE:
<223> OTHER INFORMATION: 1-221: aa 19-239 of NP_054862.1
<220> FEATURE:
<223> OTHER INFORMATION: 222-448: hFc: aa 104-330 of P01857

<400> SEQUENCE: 325

```
Phe Thr Val Thr Val Pro Lys Asp Leu Tyr Val Val Glu Tyr Gly Ser
```

-continued

```
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430
```

```
Leu His Asn His Tyr Thr Gln Lys Ser Leu Ser Leu Ser Pro Gly Lys
        435                 440                 445


<210> SEQ ID NO 326
<211> LENGTH: 454
<212> TYPE: PRT
<213> ORGANISM: Artificial Sequence
<220> FEATURE:
<223> OTHER INFORMATION: hPD-L1-mFc
<220> FEATURE:
<223> OTHER INFORMATION: 1-221: aa 19-239 of NP_054862.1
<220> FEATURE:
<223> OTHER INFORMATION: 222-454: mFc: aa 98-330 of P01863

<400> SEQUENCE: 326

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr Glu Pro Arg
    210                 215                 220

Gly Pro Thr Ile Lys Pro Cys Pro Pro Cys Lys Cys Pro Ala Pro Asn
225                 230                 235                 240

Leu Leu Gly Gly Pro Ser Val Phe Ile Phe Pro Pro Lys Ile Lys Asp
                245                 250                 255

Val Leu Met Ile Ser Leu Ser Pro Ile Val Thr Cys Val Val Val Asp
            260                 265                 270

Val Ser Glu Asp Asp Pro Asp Val Gln Ile Ser Trp Phe Val Asn Asn
        275                 280                 285

Val Glu Val His Thr Ala Gln Thr Gln Thr His Arg Glu Asp Tyr Asn
    290                 295                 300

Ser Thr Leu Arg Val Val Ser Ala Leu Pro Ile Gln His Gln Asp Trp
305                 310                 315                 320

Met Ser Gly Lys Glu Phe Lys Cys Lys Val Asn Asn Lys Asp Leu Pro
```

```
                325                 330                 335

Ala Pro Ile Glu Arg Thr Ile Ser Lys Pro Lys Gly Ser Val Arg Ala
            340                 345                 350

Pro Gln Val Tyr Val Leu Pro Pro Pro Glu Glu Glu Met Thr Lys Lys
        355                 360                 365

Gln Val Thr Leu Thr Cys Met Val Thr Asp Phe Met Pro Glu Asp Ile
    370                 375                 380

Tyr Val Glu Trp Thr Asn Asn Gly Lys Thr Glu Leu Asn Tyr Lys Asn
385                 390                 395                 400

Thr Glu Pro Val Leu Asp Ser Asp Gly Ser Tyr Phe Met Tyr Ser Lys
                405                 410                 415

Leu Arg Val Glu Lys Lys Asn Trp Val Glu Arg Asn Ser Tyr Ser Cys
            420                 425                 430

Ser Val Val His Glu Gly Leu His Asn His His Thr Thr Lys Ser Phe
        435                 440                 445

Ser Arg Thr Pro Gly Lys
    450


<210> SEQ ID NO 327
<211> LENGTH: 288
<212> TYPE: PRT
<213> ORGANISM: Artificial Sequence
<220> FEATURE:
<223> OTHER INFORMATION: hPD-1 NP_005009.2

<400> SEQUENCE: 327

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
```

```
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 328
<211> LENGTH: 290
<212> TYPE: PRT
<213> ORGANISM: Artificial Sequence
<220> FEATURE:
<223> OTHER INFORMATION: hPD-L1 NP_054862.1

<400> SEQUENCE: 328

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290
```

```
<210> SEQ ID NO 329
<211> LENGTH: 379
<212> TYPE: PRT
<213> ORGANISM: Artificial Sequence
<220> FEATURE:
<223> OTHER INFORMATION: aa1-146: M.fascicularis PD-1 (with C93S change)
      aa147-379: mFc tag (aa 98-330 of P01863)

<400> SEQUENCE: 329

Leu Glu Ser Pro Asp Arg Pro Trp Asn Pro Pro Thr Phe Ser Pro Ala
1               5                   10                  15

Leu Leu Leu Val Thr Glu Gly Asp Asn Ala Thr Phe Thr Cys Ser Phe
            20                  25                  30

Ser Asn Ala Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Arg Asp Ser Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Ala
    130                 135                 140

Leu Val Glu Pro Arg Gly Pro Thr Ile Lys Pro Cys Pro Pro Cys Lys
145                 150                 155                 160

Cys Pro Ala Pro Asn Leu Leu Gly Gly Pro Ser Val Phe Ile Phe Pro
                165                 170                 175

Pro Lys Ile Lys Asp Val Leu Met Ile Ser Leu Ser Pro Ile Val Thr
            180                 185                 190

Cys Val Val Val Asp Val Ser Glu Asp Asp Pro Asp Val Gln Ile Ser
        195                 200                 205

Trp Phe Val Asn Asn Val Glu Val His Thr Ala Gln Thr Gln Thr His
    210                 215                 220

Arg Glu Asp Tyr Asn Ser Thr Leu Arg Val Val Ser Ala Leu Pro Ile
225                 230                 235                 240

Gln His Gln Asp Trp Met Ser Gly Lys Glu Phe Lys Cys Lys Val Asn
                245                 250                 255

Asn Lys Asp Leu Pro Ala Pro Ile Glu Arg Thr Ile Ser Lys Pro Lys
            260                 265                 270

Gly Ser Val Arg Ala Pro Gln Val Tyr Val Leu Pro Pro Pro Glu Glu
        275                 280                 285

Glu Met Thr Lys Lys Gln Val Thr Leu Thr Cys Met Val Thr Asp Phe
    290                 295                 300

Met Pro Glu Asp Ile Tyr Val Glu Trp Thr Asn Asn Gly Lys Thr Glu
305                 310                 315                 320

Leu Asn Tyr Lys Asn Thr Glu Pro Val Leu Asp Ser Asp Gly Ser Tyr
                325                 330                 335

Phe Met Tyr Ser Lys Leu Arg Val Glu Lys Lys Asn Trp Val Glu Arg
            340                 345                 350

Asn Ser Tyr Ser Cys Ser Val Val His Glu Gly Leu His Asn His His
        355                 360                 365
```

```
Thr Thr Lys Ser Phe Ser Arg Thr Pro Gly Lys
    370                 375


<210> SEQ ID NO 330
<211> LENGTH: 444
<212> TYPE: PRT
<213> ORGANISM: Artificial Sequence
<220> FEATURE:
<223> OTHER INFORMATION: H4H7798N
      aa1-117: HCVR
      aa118-444: HC constant

<400> SEQUENCE: 330

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Gly Arg Asp Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
```

```
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440


<210> SEQ ID NO 331
<211> LENGTH: 214
<212> TYPE: PRT
<213> ORGANISM: Artificial Sequence
<220> FEATURE:
<223> OTHER INFORMATION: H4H7798N
      aa1-107: LCVR
      aa108-214: LC constant

<400> SEQUENCE: 331

Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Gly Val Pro Ser Arg Phe Ser Gly
    50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 332
<211> LENGTH: 449
<212> TYPE: PRT
<213> ORGANISM: Artificial Sequence
```

```
<220> FEATURE:
<223> OTHER INFORMATION: H4H7795N2
      aa1-122: HCVR
      aa123-449: HC constant

<400> SEQUENCE: 332

Glu Val Gln Val Val Glu Ser Gly Gly Gly Leu Val Glu Pro Gly Arg
1               5                   10                  15

Ser Leu Arg Leu Ser Cys Lys Ala Ser Gly Phe Thr Phe Asp Asp Tyr
            20                  25                  30

Ala Met His Trp Val Arg Gln Thr Pro Gly Lys Ala Leu Glu Trp Val
        35                  40                  45

Ser Gly Ile Ser Trp Ser Gly Asn Asn Ile Gly Tyr Ala Asp Ser Val
    50                  55                  60

Lys Gly Arg Phe Thr Ile Ser Lys Asp Asp Ala Lys Asn Ser Leu Tyr
65                  70                  75                  80

Leu Gln Met Asn Ser Leu Arg Pro Glu Asp Thr Ala Leu Tyr Tyr Cys
                85                  90                  95

Thr Lys Asp Ile Ser Ile Thr Gly Thr Leu Asp Ala Phe Asp Val Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys


<210> SEQ ID NO 333
<211> LENGTH: 214
<212> TYPE: PRT
<213> ORGANISM: Artificial Sequence
<220> FEATURE:
<223> OTHER INFORMATION: H4H7795N2
      aa1-107: LCVR
      aa108-214: LC constant

<400> SEQUENCE: 333

Asp Ile Gln Met Thr Gln Ser Pro Ile Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Ile Ala Pro Lys Leu Leu Ile
        35                  40                  45

Tyr Ser Ala Ser Ser Leu Gln Ser Gly Val Pro Ser Arg Phe Arg Gly
    50                  55                  60

Ser Gly Ser Gly Thr Asp Phe Thr Leu Thr Ile Gly Ser Leu Gln Pro
65                  70                  75                  80

Glu Asp Phe Ala Thr Tyr Tyr Cys Gln Gln Ala His Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 334
<211> LENGTH: 446
<212> TYPE: PRT
<213> ORGANISM: Artificial Sequence
<220> FEATURE:
<223> OTHER INFORMATION: H4H9008P
      aa1-119: HCVR
      aa120-446: HC constant

<400> SEQUENCE: 334
```

```
Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Thr Tyr
            20                  25                  30

Ala Met Ala Trp Val Arg Gln Thr Pro Gly Lys Gly Leu Glu Gly Val
        35                  40                  45

Ser Ala Ile Gly Gly Ser Gly Asp Ser Thr Tyr Tyr Val Asp Ser Val
    50                  55                  60

Lys Gly Arg Phe Thr Ile Ser Arg Asp Asn Ser Lys Ser Thr Leu Phe
65                  70                  75                  80

Leu Gln Met Asn Ser Leu Arg Ala Glu Asp Thr Ala Val Tyr Tyr Cys
                85                  90                  95

Val Lys Val Arg Asn Tyr Asp Gly Ser Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415
```

```
Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445


<210> SEQ ID NO 335
<211> LENGTH: 215
<212> TYPE: PRT
<213> ORGANISM: Artificial Sequence
<220> FEATURE:
<223> OTHER INFORMATION: H4H9008P
      aa1-108: LCVR
      aa109-215: LC constant

<400> SEQUENCE: 335

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 336
<211> LENGTH: 448
<212> TYPE: PRT
<213> ORGANISM: Artificial Sequence
<220> FEATURE:
<223> OTHER INFORMATION: H4H9048P2
      aa1-121: HCVR
      aa122-448: HC constant

<400> SEQUENCE: 336

Gln Val Gln Leu Val Gln Ser Gly Ala Glu Val Lys Arg Pro Gly Ser
1               5                   10                  15

Ser Val Lys Val Ser Cys Lys Val Ser Gly Val Thr Phe Arg Asn Phe
            20                  25                  30

Ala Ile Ile Trp Val Arg Gln Ala Pro Gly Gln Gly Leu Glu Trp Met
```

```
        35                  40                  45

Gly Gly Ile Ile Pro Phe Phe Ser Ala Ala Asn Tyr Ala Gln Ser Phe
    50                  55                  60

Gln Gly Arg Val Thr Ile Thr Pro Asp Glu Ser Thr Ser Thr Ala Phe
65                  70                  75                  80

Met Glu Leu Ala Ser Leu Arg Ser Glu Asp Thr Ala Val Tyr Tyr Cys
                85                  90                  95

Ala Arg Glu Gly Glu Arg Gly His Thr Tyr Gly Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```

<210> SEQ ID NO 337

-continued

```
<211> LENGTH: 215
<212> TYPE: PRT
<213> ORGANISM: Artificial Sequence
<220> FEATURE:
<223> OTHER INFORMATION: H4H9048P2
      aa1-108: LCVR
      aa109-215: LC constant

<400> SEQUENCE: 337

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

HUMAN ANTIBODIES TO PD-1

CROSS-REFERENCE TO RELATED APPLICATIONS

This is a Continuation of U.S. patent application Ser. No. 14/603,776, filed Jan. 23, 2015, which claims the benefit under 35 U.S.C. § 119(e) of U.S. provisional application Nos. 61/930,576, filed on Jan. 23, 2014; and 62/014,181, filed on Jun. 19, 2014, the disclosures of each herein incorporated by reference in their entireties.

FIELD OF THE INVENTION

The present invention is related to human antibodies and antigen-binding fragments of human antibodies that specifically bind to the immunomodulatory receptor programmed death-1 (PD-1), and therapeutic and diagnostic methods of using those antibodies.

STATEMENT OF RELATED ART

Programmed death-1 (PD-1) (also called CD279) is a 288 amino acid protein receptor expressed on activated T-cells and B-cells, natural killer cells and monocytes. PD-1 is a member of the CD28/CTLA-4 (cytotoxic T lymphocyte antigen)/ICOS (inducible co-stimulator) family of T-cell co-inhibitory receptors (Chen et al 2013, Nat. Rev. Immunol. 13: 227-242). The primary function of PD-1 is to attenuate the immune response (Riley 2009, Immunol. Rev. 229: 114-125). PD-1 has two ligands, PD-ligand1 (PD-L1) and PD-L2. PD-L1 (CD274, B7H1) is expressed widely on both lymphoid and non-lymphoid tissues such as CD4 and CD8 T-cells, macrophage lineage cells, peripheral tissues as well as on tumor cells, virally-infected cells and autoimmune tissue cells. PD-L2 (CD273, B7-DC) has a more restricted expression than PD-L1, being expressed on activated dendritic cells and macrophages (Dong et al 1999, Nature Med.). PD-L1 is expressed in most human cancers, including melanoma, glioma, non-small cell lung cancer, squamous cell carcinoma of head and neck, leukemia, pancreatic cancer, renal cell carcinoma, and hepatocellular carcinoma, and may be inducible in nearly all cancer types (Zou and Chen 2008, Nat. Rev. Immunol. 8: 467-77). PD-1 binding to its ligands results in decreased T-cell proliferation and cytokine secretion, compromising humoral and cellular immune responses in diseases such as cancer, viral infection and autoimmune disease. Blockade of PD-1 binding to reverse immunosuppression has been studied in autoimmune, viral and tumor immunotherapy (Ribas 2012, NEJM 366: 2517-2519; Watanabe et al 2012, Clin. Dev. Immunol. Volume 2012, Article ID: 269756; Wang et al 2013, J. Viral Hep. 20: 27-39).

T-cell co-stimulatory and co-inhibitory molecules (collectively named co-signaling molecules) play a crucial role in regulating T-cell activation, subset differentiation, effector function and survival (Chen et al 2013, Nature Rev. Immunol. 13: 227-242). Following recognition of cognate peptide-MHC complexes on antigen-presenting cells by the T-cell receptor, co-signaling receptors co-localize with T-cell receptors at the immune synapse, where they synergize with TCR signaling to promote or inhibit T-cell activation and function (Flies et al 2011, Yale J. Biol. Med. 84: 409-421). The ultimate immune response is regulated by a balance between co-stimulatory and co-inhibitory signals ("immune checkpoints") (Pardoll 2012, Nature 12: 252-264). PD-1 functions as one such 'immune checkpoint' in mediating peripheral T-cell tolerance and in avoiding autoimmunity. PD-1 binds to PD-L1 or PD-L2 and inhibits T-cell activation. The ability of PD1 to inhibit T-cell activation is exploited by chronic viral infections and tumors to evade immune response. In chronic viral infections, PD-1 is highly expressed on virus-specific T-cells and these T-cells become "exhausted" with loss of effector functions and proliferative capacity (Freeman 2008, PNAS 105: 10275-10276). PD-L1 is expressed on a wide variety of tumors and studies on animal models have shown that PD-L1 on tumors inhibits T-cell activation and lysis of tumor cells and may lead to increased death of tumor-specific T-cells. The PD-1: PD-L1 system also plays an important role in induced T-regulatory (Treg) cell development and in sustaining Treg function (Francisco et al 2010, Immunol. Rev. 236: 219-242).

Since PD-1 plays an important role in autoimmunity, tumor immunity and infectious immunity, it is an ideal target for immunotherapy. Blocking PD-1 with antagonists, including monoclonal antibodies, has been studied in treatments of cancer and chronic viral infections (Sheridan 2012, Nature Biotechnology 30: 729-730).

Monoclonal antibodies to PD-1 are known in the art and have been described, for example, in US Patent/Publication Nos. U.S. Pat. Nos. 8,008,449, 8,168,757, 20110008369, 20130017199, 20130022595, and in WO2006121168, WO20091154335, WO2012145493, WO2013014668, WO2009101611, EP2262837, and EP2504028.

BRIEF SUMMARY OF THE INVENTION

The present invention provides antibodies and antigen-binding fragments thereof that bind PD-1. The antibodies of the present invention are useful, inter alia, for targeting T cells expressing PD-1, and for modulating PD-1 activity. In certain embodiments, the antibodies of the invention are useful for inhibiting or neutralizing PD-1 activity and/or for stimulating T cell activation, e.g., under circumstances where T cell-mediated killing is beneficial or desirable. In alternate embodiments, the antibodies enhance PD-1 binding and/or activity and may be used to inhibit T-cell activation. The anti-PD-1 antibodies of the invention, or antigen-binding portions thereof, may be included as part of a multi-specific antigen-binding molecule, for example, to modulate the immune response and/or to target the antibodies to a specific cell type, such as a tumor cell, an autoimmune tissue cell or a virally infected cell. The antibodies are useful in treating a disease or disorder such as cancer, viral infection and autoimmune disease.

The antibodies of the invention can be full-length (for example, an IgG1 or IgG4 antibody) or may comprise only an antigen-binding portion (for example, a Fab, $F(ab')_2$ or scFv fragment), and may be modified to affect functionality, e.g., to eliminate residual effector functions (Reddy et al., 2000, J. Immunol. 164:1925-1933). In certain embodiments, the antibodies may be bispecific.

In a first aspect, the present invention provides isolated recombinant monoclonal antibodies or antigen-binding fragments thereof that bind specifically to PD-1. In certain embodiments, the antibodies are fully human. Exemplary anti-PD-1 antibodies of the present invention are listed in Tables 1-3 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-PD-1 antibodies. Table 2 sets forth the nucleic acid sequence identifiers of the HCVRs, LCVRs, HCDR1, HCDR2 HCDR3, LCDR1, LCDR2 and LCDR3 of the exemplary anti-PD-1 antibodies. Table 3 sets forth the amino acid sequence identifiers of heavy chain and light chain sequences of exemplary anti-PD-1 antibodies.

The present invention provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-PD-1 antibodies listed in Table 1. In certain embodiments, the HCVR/LCVR amino acid sequence pair is selected from the group consisting of SEQ ID NOs: 2/10, 18/26, 34/42, 50/58, 66/74, 82/90, 98/106, 114/122, 130/138, 146/154, 162/170, 178/186, 194/202, 210/202, 218/202, 226/202, 234/202, 242/202, 250/202, 258/202, 266/202, 274/202, 282/202, 290/202, 298/186, 306/186 and 314/186. In certain embodiments, the HCVR/LCVR amino acid sequence pair is selected from one of SEQ ID NOs: 130/138 (e.g., H2M7795N), 162/170 (e.g., H2M7798N), 234/202 (e.g., H4xH9048P), or 314/186 (e.g., H4xH9008P).

The present invention also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-PD-1 antibodies listed in Table 1. In certain embodiments, the HCDR3/LCDR3 amino acid sequence pair is selected from the group consisting of SEQ ID NOs: 136/144 (e.g., H2M7795N), 168/176 (e.g., H2M7798N), 240/208 (e.g., H4xH9048P), and 320/192 (e.g., H4xH9008P).

The present invention provides antibodies, or antigen-binding fragments thereof, comprising a heavy chain comprising an amino acid sequence selected from any of the HC amino acid sequences listed in Table 3, or a substantially similar sequence thereof having at least 90%, at least 95%, at least 98% or at least 99% sequence identity thereto.

The present invention also provides antibodies, or antigen-binding fragments thereof, comprising a light chain comprising an amino acid sequence selected from any of the LC amino acid sequences listed in Table 3, or a substantially similar sequence thereof having at least 90%, at least 95%, at least 98% or at least 99% sequence identity thereto.

The present invention also provides antibodies, or antigen-binding fragments thereof, comprising a HC and a LC amino acid sequence pair (HC/LC) comprising any of the HC amino acid sequences listed in Table 3 paired with any of the LC amino acid sequences listed in Table 3. According to certain embodiments, the present invention provides antibodies, or antigen-binding fragments thereof, comprising an HC/LC amino acid sequence pair contained within any of the exemplary anti-PD-1 antibodies listed in Table 3. In certain embodiments, the HC/LC amino acid sequence pair is selected from the group consisting of SEQ ID NOs: 330/331, 332/333, 334/335, and 336/337.

The present invention also provides antibodies, or antigen-binding fragments thereof, comprising a set of six CDRs HCDR1-HCDR2-HCDR3-LCDR1-LCDR2-LCDR3) contained within any of the exemplary anti-PD-1 antibodies listed in Table 1. In certain embodiments, the HCDR1-HCDR2-HCDR3-LCDR1-LCDR2-LCDR3 amino acid sequence set is selected from the group consisting of SEQ ID NOs: 132-134-136-140-142-144 (e.g., H2M7795N); 164-166-168-172-174-176 (e.g., H2M7798N); 236-238-240-204-206-208 (e.g., H4xH9048P); and 316-318-320-188-190-192 (e.g., H4xH9008P).

In a related embodiment, the present invention provides antibodies, or antigen-binding fragments thereof, comprising a set of six CDRs HCDR1-HCDR2-HCDR3-LCDR1-LCDR2-LCDR3) contained within an HCVR/LCVR amino acid sequence pair as defined by any of the exemplary anti-PD-1 antibodies listed in Table 1. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 130/138 (e.g., H2M7795N); 162/170 (e.g., H2M7798N); 234/202 (e.g., H4xH9048P); and 314/186 (e.g., H4xH9008P). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, “Sequences of Proteins of Immunological Interest,” National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention includes anti-PD-1 antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

The present invention also provides for antibodies and antigen-binding fragments thereof that compete for specific binding to PD-1 with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides isolated antibodies and antigen-binding fragments thereof that block PD-1 binding to PD-L1 or PD-L2. In some embodiments, the antibody or antigen-binding fragment thereof that blocks PD-1 binding to PD-L1 may bind to the same epitope on PD-1 as PD-L1 or may bind to a different epitope on PD-1 as PD-L1.

In alternate embodiments, the present invention provides antibodies and antigen-binding fragments thereof that stimulate PD-1 binding to PD-L1. In certain embodiments, the present invention provides isolated antibodies or antigen-binding fragments thereof that bind PD-1, wherein the antibodies or antigen-binding fragments thereof enhance PD-1 binding to PD-L1. In some embodiments, the isolated antibodies or antigen-binding fragments thereof comprise the CDRs of a HCVR, wherein the HCVR has an amino acid sequence selected from the group consisting of SEQ ID NOs: 2, 98, and 250; and the CDRs of a LCVR, wherein the LCVR has an amino acid sequence selected from the group consisting of SEQ ID NOs: 10, 106, and 202. In some embodiments, the isolated antibodies or antigen-binding fragments thereof comprise an HCVR/LCVR amino acid sequence pair selected from the group consisting of SEQ ID NOs: 2/10 (e.g., H1M7789N), 98/106 (e.g., H2M7791N), and 250/202 (e.g., H4H9068P2).

The present invention also provides antibodies and antigen-binding fragments thereof that bind specifically to PD-1 from human or other species. In certain embodiments, the antibodies may bind to human PD-1 and/or to cynomolgus PD-1.

The present invention also provides antibodies and antigen-binding fragments thereof that cross-compete for binding to PD-1 with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

In one embodiment, the invention provides an isolated antibody or antigen-binding fragment that has one or more of the following characteristics: (a) blocks the binding of PD-1 to PD-L1 or PD-L2; (b) binds specifically to human PD-1 and/or cynomolgus PD-1; (c) blocks PD-1-induced T-cell down regulation and rescues T-cell signaling; (d) suppresses tumor growth and increases survival in subjects with colon cancer; (e) inhibits T-cell proliferation in a mixed lymphocyte reaction (MLR) assay; and (f) increases IL-2 and/or interferon-gamma secretion in a MLR assay.

In some embodiments, the antibody or antigen binding fragment thereof may bind specifically to PD-1 in an agonist manner, i.e., it may enhance or stimulate PD-1 binding and/or activity; in other embodiments, the antibody may bind specifically to PD-1 in an antagonist manner, i.e., it may block PD-1 from binding to its ligand.

In certain embodiments, the antibodies or antigen-binding fragments of the present invention are bispecific comprising a first binding specificity to PD-1 and a second binding specificity for a second target epitope. The second target epitope may be another epitope on PD-1 or on a different protein. In certain embodiments, the target epitope may be on a different cell including a different T-cell, a B-cell, a tumor cell, an autoimmune tissue cell or a virally infected cell.

In a second aspect, the present invention provides nucleic acid molecules encoding anti-PD-1 antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-PD-1 antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-PD-1 antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-PD-1 antibody listed in Table 1.

The present invention provides nucleic acid molecules encoding any of the heavy chain amino acid sequences listed in Table 3. The present invention also provides nucleic acid molecules encoding any of the light chain amino acid sequences listed in Table 3.

The present invention also provides nucleic acid molecules encoding both heavy chain (HC) and a light chain (LC), wherein the HC comprises an amino acid sequence of any of the HC amino acid sequences listed in Table 3, and wherein the LC comprises an amino acid sequence of any of the LC amino acid sequences listed in Table 3.

In a related aspect, the present invention provides recombinant expression vectors capable of expressing a polypeptide comprising a heavy or light chain variable region of an anti-PD-1 antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. The present invention also provides recombinant expression vectors capable of expressing a polypeptide comprising a heavy or light chain of an anti-PD-1 antibody. For example, the present invention includes recombinant expression vectors comprising any of the nucleic acid molecules mentioned above, i.e., nucleic acid molecules encoding any of the heavy chain or light chain sequences as set forth in Table 3. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In a third aspect, the present invention provides multi-specific antigen-binding molecules and antigen-binding fragments thereof comprising a first antigen-binding specificity that binds specifically to PD-1 and a second antigen-binding specificity that binds specifically to an antigen selected from the group consisting of a tumor cell-specific antigen, an autoimmune tissue-specific antigen, an infected-cell-specific antigen, a T-cell co-inhibitor, a T-cell receptor, a Fc receptor, PD-L1, and PD-1. In certain embodiments, the first antigen-binding specificity may comprise three CDRs derived from a HCVR with an amino acid sequence selected from the HCVR sequences in Table 1 and three CDRs derived from a LCVR with an amino acid sequence selected from the LCVR sequences in Table 1. In one embodiment, the first antigen-binding specificity may comprise the extracellular domain of PD-L1. The second antigen-binding specificity may target an antigen on the same cell as PD-1 or on a different cell of the same tissue type or of a different tissue type. For example, the multi-specific antigen-binding molecule may bind to a T-cell wherein the first antigen-binding specificity may bind specifically to PD-1 and the second antigen-binding specificity may bind to a T-cell receptor on the T-cell. Alternatively, in another embodiment, the first antigen-binding specificity may bind specifically to PD-1 on a T-cell and the second antigen-binding specificity may be targeted to an antigen/receptor on a B-cell or a macrophage or antigen-presenting cell. In certain embodiments, the second antigen-binding specificity may be directed to an antigen associated with an autoimmune tissue. In one embodiment, the first antigen-binding specificity may comprise an extracellular domain of PD-L1 and the second antigen-binding specificity may bind to another epitope on PD-1. In certain embodiments, the first antigen-binding specificity binds to PD-1 with a lower affinity, for example, with a $K_D$ more than $10^{-7}$ M, more than $10^{-6}$ M, more than $10^{-5}$ M, or more than $10^{-4}$ M.

In a fourth aspect, the invention provides a pharmaceutical composition comprising a recombinant human antibody or fragment thereof which specifically binds PD-1 and a pharmaceutically acceptable carrier. In a related aspect, the invention features a composition which is a combination of an anti-PD-1 antibody and a second therapeutic agent. In one embodiment, the second therapeutic agent is any agent that is advantageously combined with an anti-PD-1 antibody. Exemplary agents that may be advantageously combined with an anti-PD-1 antibody include, without limitation, other agents that bind and/or modulate PD-1 signaling (including other antibodies or antigen-binding fragments thereof, etc.) and/or agents which do not directly bind PD-1 but nonetheless modulate immune cell activation. Additional combination therapies and co-formulations involving the anti-PD-1 antibodies of the present invention are disclosed elsewhere herein.

In a fifth aspect, the invention provides methods to modulate the immune response in a subject, the method comprising administering a therapeutically effective amount of an anti-PD-1 antibody or antigen-binding fragment thereof of the invention to the subject in need thereof. In certain embodiments, the invention provides methods to enhance the immune response in a subject, the methods comprising administering to the subject an effective amount of an antibody or fragment thereof of the invention that binds PD-1 and blocks PD-1 binding to PD-L1. In one embodiment, the invention provides a method to stimulate or enhance T-cell stimulation in a subject. In one embodiment, the invention provides methods to inhibit a T-regulatory (Treg) cell in a subject, the methods comprising administering a therapeutically effective amount of a blocking antibody or antigen-binding fragment thereof of the invention to the subject in need thereof. In certain embodiments, the subject in need thereof may suffer from a disease or disorder such as cancer or viral infection. In alternate embodiments, the invention provides for methods to inhibit or suppress T-cell activation in a subject, the methods comprising administering a therapeutically effective amount of an activating antibody or fragment thereof of the invention to the subject in need thereof. In one embodiment, the subject may suffer from an autoimmune disease or disorder.

In a sixth aspect, the invention provides therapeutic methods for treating a disease or disorder such as cancer, autoimmune disease or viral infection in a subject using an anti-PD-1 antibody or antigen-binding portion of an antibody of the invention, wherein the therapeutic methods comprise administering a therapeutically effective amount of a pharmaceutical composition comprising an antibody or fragment of an antibody of the invention to the subject in need thereof. The disorder treated is any disease or condition which is improved, ameliorated, inhibited or prevented by stimulation or inhibition of PD-1 activity or signaling. In certain embodiments, the antibody or antigen-binding fragment thereof the invention is administered in combination with a second therapeutic agent to the subject in need thereof. The second therapeutic agent may be selected from the group consisting of an antibody to another T-cell co-inhibitor, an antibody to a tumor cell antigen, an antibody to a T-cell receptor, an antibody to a Fc receptor, an antibody to an epitope on a virally infected cell, an antibody to an autoimmune tissue antigen, an antibody to PD-L1, a cytotoxic agent, an anti-cancer drug, an anti-viral drug, an anti-inflammatory drug (e.g., corticosteroids), chemotherapeutic agent, radiation therapy, an immunosuppressant and any other drug or therapy known in the art. In certain embodiments, the second therapeutic agent may be an agent that helps to counteract or reduce any possible side effect(s) associated with an antibody or antigen-binding fragment thereof of the invention, if such side effect(s) should occur.

In certain embodiments, the present invention provides methods for suppressing tumor growth. In certain embodiments, the present invention provides methods to enhance survival of cancer patients. Examples of cancer include, but are not limited to, primary and/or recurrent cancer, including brain cancer (e.g., glioblastoma multiforme), lung cancer (e.g., non-small cell lung cancer), squamous cell carcinoma of head and neck, renal cell carcinoma, melanoma, multiple myeloma, prostate cancer, and colon cancer. The methods comprise administering a pharmaceutical composition comprising a therapeutically effective amount of an anti-PD-1 antibody of the present invention in combination with a second therapeutic agent selected from the group consisting of a vascular endothelial growth factor (VEGF) antagonist (e.g., aflibercept, bevacizumab), an angiopoietin-2 (Ang2) inhibitor (e.g., an anti-Ang2 antibody such as nesvacumab), a lymphocyte activation gene 3 (LAG-3) inhibitor, a cytotoxic T-lymphocyte antigen 4 (CTLA-4) inhibitor (e.g., ipilimumab), a chemotherapeutic agent, and radiation therapy. Additional examples of additional therapies/therapeutic agents that can be used in combination with an anti-PD-1 antibody of the invention for use in treating cancer are described elsewhere herein.

The antibody or fragment thereof may be administered subcutaneously, intravenously, intradermally, intraperitoneally, orally, intramuscularly, or intracranially. The antibody or fragment thereof may be administered at a dose of about 0.1 mg/kg of body weight to about 100 mg/kg of body weight of the subject.

The present invention also includes use of an anti-PD-1 antibody or antigen-binding fragment thereof of the invention in the manufacture of a medicament for the treatment of a disease or disorder that would benefit from the blockade or enhancement of PD-1 binding and/or signaling.

Other embodiments will become apparent from a review of the ensuing detailed description.

DETAILED DESCRIPTION

Figure 1:
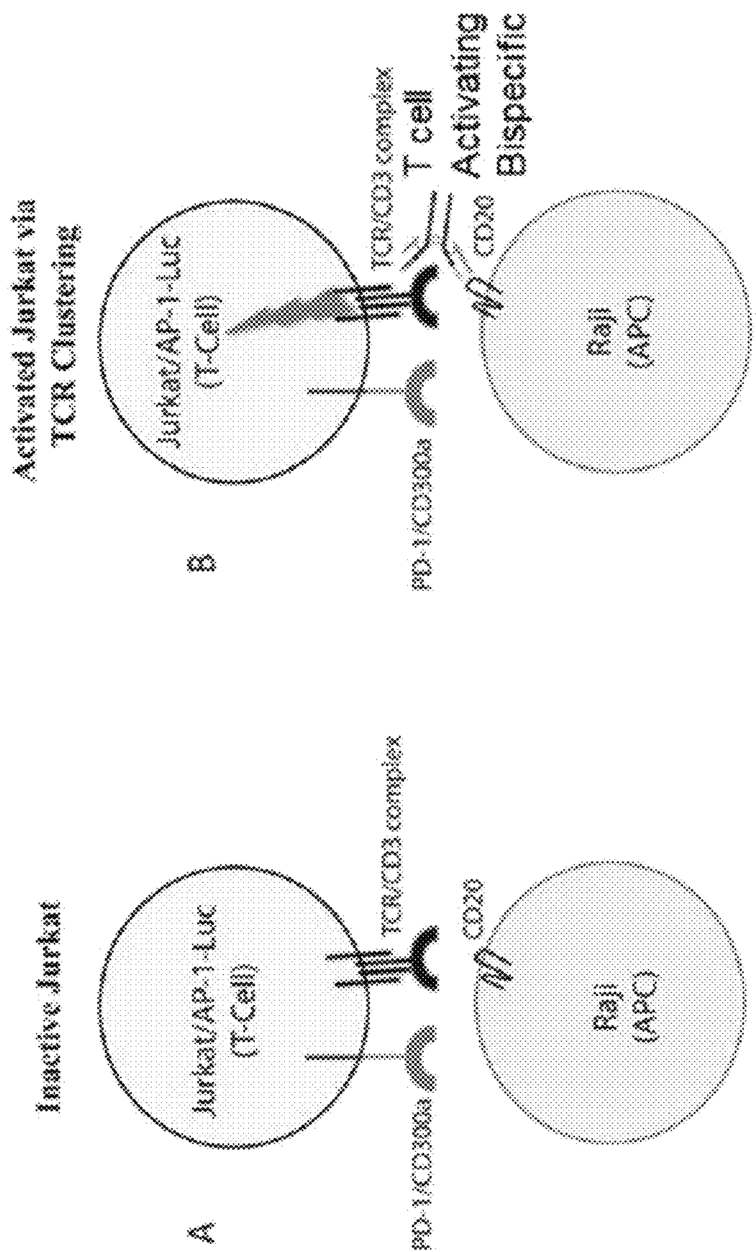
FIG. 1 is a schematic of the luciferase-based PD-1 bioassay described in Example 8 herein. Panel A: Inactive Jurkat cells; Panel B: Jurkat cells are activated by T-cell receptor (TCR) clustering through the CD3xCD20 bispecific antibody; Panel C: PD-1 activation attenuates response in activated Jurkat cells; Panel D: Blocking PD-1 rescues the response in activated Jurkat cells.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

The term "PD-1" refers to the programmed death-1 protein, a T-cell co-inhibitor, also known as CD279. The amino acid sequence of full-length PD-1 is provided in GenBank as accession number NP_005009.2 and is also referred to herein as SEQ ID NO: 327. The term "PD-1" also includes protein variants of PD-1 having the amino acid sequence of SEQ ID NOs: 321, 322, 323, or 324. The term "PD-1" includes recombinant PD-1 or a fragment thereof. The term also encompasses PD-1 or a fragment thereof coupled to, for example, histidine tag, mouse or human Fc, or a signal sequence such as ROR1. For example, the term includes sequences exemplified by SEQ ID NOs: 323 or 324, comprising a mouse Fc (mIgG2a) or human Fc (hIgG1) at the C-terminal, coupled to amino acid residues 25-170 of full-length PD-1 with a C93S change. Protein variants as exemplified by SEQ ID NO: 321 comprise a histidine tag at the C-terminal, coupled to amino acid residues 25-170 of full length PD-1. Unless specified as being from a non-human species, the term "PD-1" means human PD-1.

PD-1 is a member of the CD28/CTLA-4/ICOS family of T-cell co-inhibitors. PD-1 is a 288-amino acid protein with an extracellular N-terminal domain which is IgV-like, a transmembrane domain and an intracellular domain containing an immunoreceptor tyrosine-based inhibitory (ITIM) motif and an immunoreceptor tyrosine-based switch (ITSM) motif (Chattopadhyay et al 2009, Immunol. Rev.). The PD-1 receptor has two ligands, PD-ligand-1 (PD-L1) and PD-L2.

The term "PD-L1" refers to the ligand of the PD-1 receptor also known as CD274 and B7H1. The amino acid sequence of full-length PD-L1 is provided in GenBank as accession number NP_054862.1 and is also referred to herein as SEQ ID NO: 328. The term also encompasses PD-L1 or a fragment thereof coupled to, for example, histidine tag, mouse or human Fc, or a signal sequence such as ROR1. For example, the term includes sequences exemplified by SEQ ID NOs: 325 or 326, comprising a mouse Fc (mIgG2a) or human Fc (hIgG1) at the C-terminal, coupled to amino acid residues 19-239 of full-length PD-L1. PD-L1 is a 290 amino acid protein with an extracellular IgV-like domain, a transmembrane domain and a highly conserved intracellular domain of approximately 30 amino acids. PD-L1 is constitutively expressed on many cells such as antigen presenting cells (e.g., dendritic cells, macrophages, and B-cells) and on hematopoietic and non-hematopoietic cells (e.g., vascular endothelial cells, pancreatic islets, and sites of immune privilege). PD-L1 is also expressed on a wide variety of tumors, virally-infected cells and autoimmune tissue, and is a component of the immunosuppressive milieu (Ribas 2012, NEJM 366: 2517-2519).

As used herein, the term "T-cell co-inhibitor" refers to a ligand and/or receptor which modulates the immune response via T-cell activation or suppression. The term "T-cell co-inhibitor", also known as T-cell co-signaling molecule, includes, but is not limited to, lymphocyte activation gene 3 protein (LAG-3, also known as CD223), cytotoxic T-lymphocyte antigen-4 (CTLA-4), B and T lymphocyte attenuator (BTLA), CD-28, 2B4, LY108, T-cell immunoglobulin and mucin 3(TIM3), T-cell immunoreceptor with immunoglobulin and ITIM (TIGIT; also known as VSIG9), leucocyte associated immunoglobulin-like receptor 1 (LAIR1; also known as CD305), inducible T-cell costimulator (ICOS; also known as CD278), V-domain Ig suppressor of T-cell activation (VISTA) and CD160.

As used herein, the term "Fc receptor" refers to the surface receptor protein found on immune cells including B lymphocytes, natural killer cells, macrophages, basophils, neutrophils, and mast cells, which has a binding specificity for the Fc region of an antibody. The term "Fc receptor" includes, but is not limited to, a Fcγ receptor [e.g., FcγRI (CD64), FcγRIIA (CD32), FcγRIIB (CD32), FcγRIIIA (CD16a), and FcγRIIIB (CD16b)], Fcα receptor (e.g., FcαRI or CD89) and Fcε receptor [e.g., FcεRI, and FcεRII (CD23)].

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-PD-1 monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human anti-PD-1 monoclonal antibodies comprising variants of any of the HCVR, LCVR, and/or CDR amino acid sequences disclosed herein having one or more conservative substitutions. For example, the present invention includes anti-PD-1 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "recombinant", as used herein, refers to antibodies or antigen-binding fragments thereof of the invention created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

The term "multi-specific antigen-binding molecules", as used herein refers to bispecific, tri-specific or multi-specific antigen-binding molecules, and antigen-binding fragments thereof. Multi-specific antigen-binding molecules may be specific for different epitopes of one target polypeptide or may contain antigen-binding domains specific for epitopes of more than one target polypeptide. A multi-specific antigen-binding molecule can be a single multifunctional polypeptide, or it can be a multimeric complex of two or more polypeptides that are covalently or non-covalently associated with one another. The term "multi-specific antigen-binding molecules" includes antibodies of the present invention that may be linked to or co-expressed with another functional molecule, e.g., another peptide or protein. For example, an antibody or fragment thereof can be functionally linked (e.g., by chemical coupling, genetic fusion, non-covalent association or otherwise) to one or more other molecular entities, such as a protein or fragment thereof to produce a bi-specific or a multi-specific antigen-binding molecule with a second binding specificity. According to the present invention, the term "multi-specific antigen-binding molecules" also includes bi-specific, tri-specific or multi-specific antibodies or antigen-binding fragments thereof. In certain embodiments, an antibody of the present invention is functionally linked to another antibody or antigen-binding fragment thereof to produce a bispecific antibody with a second binding specificity. Bispecific and multi-specific antibodies of the present invention are described elsewhere herein.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to PD-1. Moreover, multi-specific antibodies that bind to one domain in PD-1 and one or more additional antigens or a bi-specific that binds to two different regions of PD-1 are nonetheless considered antibodies that "specifically bind", as used herein.

The term "high affinity" antibody refers to those mAbs having a binding affinity to PD-1, expressed as $K_D$, of at least $10^{-7}$ M; preferably $10^{-8}$ M; more preferably $10^{-9}$M, even more preferably $10^{-10}$ M, even more preferably $10^{-11}$ M, as measured by surface plasmon resonance, e.g., BIACORE™ or solution-affinity ELISA.

By the term "slow off rate", "Koff" or "kd" is meant an antibody that dissociates from PD-1, with a rate constant of $1\times10^{-3}$ $s^{-1}$ or less, preferably $1\times10^{-4}$ $s^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to PD-1.

In specific embodiments, antibody or antibody fragments of the invention may be conjugated to a moiety such a ligand or a therapeutic moiety ("immunoconjugate"), such as an antibiotic, a second anti-PD-1 antibody, or an antibody to another antigen such a tumor-specific antigen, an autoimmune tissue antigen, a virally-infected cell antigen, a Fc receptor, a T-cell receptor, or a T-cell co-inhibitor, or an immunotoxin, or any other therapeutic moiety useful for treating a disease or condition including cancer, autoimmune disease or chronic viral infection.

An "isolated antibody", as used herein, is intended to refer to an antibody that is substantially free of other antibodies (Abs) having different antigenic specificities (e.g., an isolated antibody that specifically binds PD-1, or a fragment thereof, is substantially free of Abs that specifically bind antigens other than PD-1.

A "blocking antibody" or a "neutralizing antibody", as used herein (or an "antibody that neutralizes PD-1 activity" or "antagonist antibody"), is intended to refer to an antibody whose binding to PD-1 results in inhibition of at least one biological activity of PD-1. For example, an antibody of the invention may prevent or block PD-1 binding to PD-L1.

An "activating antibody" or an "enhancing antibody", as used herein (or an "agonist antibody"), is intended to refer to an antibody whose binding to PD-1 results in increasing or stimulating at least one biological activity of PD-1. For example, an antibody of the invention may increase PD-1 binding to PD-L1.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, in need of amelioration, prevention and/or treatment of a disease or disorder such as chronic viral infection, cancer or autoimmune disease.

As used herein, "anti-cancer drug" means any agent useful to treat cancer including, but not limited to, cytotoxins and agents such as antimetabolites, alkylating agents, anthracyclines, antibiotics, antimitotic agents, procarbazine, hydroxyurea, asparaginase, corticosteroids, mytotane (O,P'-(DDD)), biologics (e.g., antibodies and interferons) and radioactive agents. As used herein, "a cytotoxin or cytotoxic agent", also refers to a chemotherapeutic agent and means any agent that is detrimental to cells. Examples include Taxol® (paclitaxel), temozolamide, cytochalasin B, gramicidin D, ethidium bromide, emetine, cisplatin, mitomycin, etoposide, tenoposide, vincristine, vinbiastine, coichicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

As used herein, the term "anti-viral drug" refers to any drug or therapy used to treat, prevent, or ameliorate a viral infection in a host subject. The term "anti-viral drug" includes, but is not limited to zidovudine, lamivudine, abacavir, ribavirin, lopinavir, efavirenz, cobicistat, tenofovir, rilpivirine, analgesics and corticosteroids. In the context of the present invention, the viral infections include long-term or chronic infections caused by viruses including, but not limited to, human immunodeficiency virus (HIV), hepatitis B virus (HBV), hepatitis C virus (HCV), human papilloma virus (HPV), lymphocytic choriomeningitis virus (LCMV), and simian immunodeficiency virus (SIV).

The antibodies and antigen-binding fragments of the present invention specifically bind to PD-1 and modulate the interaction of PD-1 with PD-L1. The anti-PD-1 antibodies may bind to PD-1 with high affinity or with low affinity. In certain embodiments, the antibodies of the present invention may be blocking antibodies wherein the antibodies may bind to PD-1 and block the interaction of PD-1 with PD-L1. In some embodiments, the blocking antibodies of the invention may block the binding of PD-1 to PD-L1 and/or stimulate or enhance T-cell activation. In some embodiments, the blocking antibodies may be useful for stimulating or enhancing the immune response and/or for treating a subject suffering from cancer, or a chronic viral infection. The antibodies when administered to a subject in need thereof may reduce the chronic infection by a virus such as HIV, LCMV or HBV in the subject. They may be used to inhibit the growth of tumor cells in a subject. They may be used alone or as adjunct therapy with other therapeutic moieties or modalities known in the art for treating cancer, or viral infection.

In other embodiments, the antibodies of the present invention may be activating antibodies, wherein the antibodies may bind to PD-1 and enhance the interaction of PD-1 and PD-L1. In some embodiments, the activating antibodies may enhance binding of PD-1 to PD-L1 and/or inhibit or suppress T-cell activation. The activating antibodies of the present invention may be useful for inhibiting the immune response in a subject and/or for treating autoimmune disease.

In certain embodiments, the anti-PD-1 antibodies may be multi-specific antigen-binding molecules, wherein they comprise a first binding specificity to PD-1 and a second binding specificity to an antigen selected from the group consisting of another T-cell co-inhibitor, an autoimmune tissue antigen, T-cell receptor, Fc receptor, T-cell receptor, PD-L1, and a different epitope of PD-1.

In certain embodiments, the antibodies of the invention are obtained from mice immunized with a primary immunogen, such as a full length PD-1 [See GenBank accession number NP_005009.2 (SEQ ID NO: 327)] or with a recombinant form of PD-1 or modified human PD-1 fragments (SEQ ID NOs: 321, 323, or 324) or with modified cynomolgus PD-1 fragments (SEQ ID NO: 322), followed by immunization with a secondary immunogen, or with an immunogenically active fragment of PD-1.

The immunogen may be a biologically active and/or immunogenic fragment of PD-1 or DNA encoding the active fragment thereof. The fragment may be derived from the N-terminal or C-terminal domain of PD-1. In certain embodiments of the invention, the immunogen is a fragment of PD-1 that ranges from amino acid residues 25-170 of SEQ ID NO: 327 with a C93S change.

The peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization.

The full-length amino acid sequence of full length human PD-1 is shown as SEQ ID NO: 327.

In certain embodiments, antibodies that bind specifically to PD-1 may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of PD-1 specific antibodies. In certain embodiments, any one or more of the above-noted regions of PD-1, or fragments thereof may be used for preparing monospecific, bispecific, or multispecific antibodies.

Certain anti-PD-1 antibodies of the present invention are able to bind to and neutralize the activity of PD-1, as determined by in vitro or in vivo assays. The ability of the antibodies of the invention to bind to and neutralize the activity of PD-1 may be measured using any standard method known to those skilled in the art, including binding assays, or activity assays, as described herein.

Non-limiting, exemplary in vitro assays for measuring binding activity are illustrated in Examples herein. In Example 3, the binding affinities and kinetic constants of human anti-PD-1 antibodies for human PD-1 and cynomolgus PD-1 were determined by surface plasmon resonance and the measurements were conducted on a Biacore 4000 or T200 instrument. In Examples 4 and 5, blocking assays were used to determine the ability of the anti-PD-1 antibodies to block PD-L1-binding ability of PD-1 in vitro. In Example 6, blocking assays were used to determine cross-competition between anti-PD-1 antibodies. Example 7 describes the binding of the antibodies to cells overexpressing PD-1. In Example 8, a luciferase assay was used to determine the ability of anti-PD-1 antibodies to antagonize PD-1/PD-L1 signaling in T-cells.

In certain embodiments, the antibodies of the present invention are able to enhance or stimulate T-cell activation in vitro and in a subject with cancer or in a subject infected with a virus such as LCMV. In certain embodiments, the antibodies of the present invention are used in combination with a second therapeutic agent, such as an antibody to a second T-cell co-inhibitor, to enhance the immune response and inhibit tumor growth in a subject.

The antibodies specific for PD-1 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antibodies may be used in diagnostic assays including imaging assays.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to PD-1. An antibody fragment may include a Fab fragment, a $F(ab')_2$ fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. In such embodiments, the term" antigen-binding fragment" includes, e.g., an extracellular domain of PD-L1 which binds specifically to PD-1. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to PD-1.

An immunogen comprising any one of the following can be used to generate antibodies to PD-1. In certain embodiments, the antibodies of the invention are obtained from mice immunized with a full length, native PD-1 (See GenBank accession number NP_005009.2) (SEQ ID NO: 327), or with a recombinant PD-1 peptide. Alternatively, PD-1 or a fragment thereof may be produced using standard biochemical techniques and modified (SEQ ID NOS: 321-324) and used as immunogen.

In certain embodiments, the immunogen may be a peptide from the N terminal or C terminal end of PD-1. In one embodiment, the immunogen is the extracellular domain or the IgV-like domain of PD-1. In certain embodiments of the invention, the immunogen is a fragment of PD-1 that ranges from about amino acid residues 25-170 of SEQ ID NO: 327 with a C93S change.

In some embodiments, the immunogen may be a recombinant PD-1 peptide expressed in *E. coli* or in any other eukaryotic or mammalian cells such as Chinese hamster ovary (CHO) cells.

In certain embodiments, antibodies that bind specifically to PD-1 may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of PD-1 specific antibodies.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to PD-1 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Bioequivalents

The anti-PD-1 antibodies and antibody fragments of the present invention encompass proteins having amino acid sequences that vary from those of the described antibodies, but that retain the ability to bind PD-1. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-PD-1 Antibodies Comprising Fc Variants

According to certain embodiments of the present invention, anti-PD-1 antibodies are provided comprising an Fc domain comprising one or more mutations which enhance or diminish antibody binding to the FcRn receptor, e.g., at acidic pH as compared to neutral pH. For example, the present invention includes anti-PD-1 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-PD-1 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). In one embodiment, the present invention includes anti-PD-1 antibodies comprising an Fc domain comprising a S108P mutation in the hinge region of IgG4 to promote dimer stabilization. All possible combinations of the foregoing Fc domain mutations, and other mutations within the antibody variable domains disclosed herein, are contemplated within the scope of the present invention.

The present invention also includes anti-PD-1 antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Ser. No. 14/170,166, filed Jan. 31, 2014, the disclosure of which is hereby incorporated by reference in its entirety).

Biological Characteristics of the Antibodies

In general, the antibodies of the present invention function by binding to PD-1. The present invention includes anti-PD-1 antibodies and antigen-binding fragments thereof that bind soluble monomeric or dimeric PD-1 molecules with high affinity. For example, the present invention includes antibodies and antigen-binding fragments of antibodies that bind monomeric PD-1 (e.g., at 25° C. or at 37° C.) with a $K_D$ of less than about 50 nM as measured by surface plasmon resonance, e.g., using the assay format as defined in Example 3 herein. In certain embodiments, the antibodies or antigen-binding fragments thereof bind monomeric PD-1 with a $K_D$ of less than about 40 nM, less than about 30 nM, less than about 20 nM, less than about 10 nM less than about 5 nM, less than about 2 nM or less than about 1 nM, as measured by surface plasmon resonance, e.g., using the assay format as defined in Example 3 herein, or a substantially similar assay.

The present invention also includes antibodies and antigen-binding fragments thereof that bind dimeric PD-1 (e.g., at 25° C. or at 37° C.) with a $K_D$ of less than about 400 pM as measured by surface plasmon resonance, e.g., using the assay format as defined in Example 3 herein. In certain embodiments, the antibodies or antigen-binding fragments thereof bind dimeric PD-1 with a $K_D$ of less than about 300 pM, less than about 250 pM, less than about 200 pM, less than about 100 pM, or less than about 50 pM, as measured by surface plasmon resonance, e.g., using the assay format as defined in Example 3 herein, or a substantially similar assay.

The present invention also includes antibodies or antigen-binding fragments thereof that bind cynomolgus (*Macaca fascicularis*) PD-1 (e.g., at 25° C. or at 37° C.) with a $K_D$ of less than about 35 nM as measured by surface plasmon resonance, e.g., using the assay format as defined in Example 3 herein. In certain embodiments, the antibodies or antigen-binding fragments thereof bind cynomolgus PD-1 with a $K_D$ of less than about 30 nM, less than about 20 nM, less than about 15 nM, less than about 10 nM, or less than about 5 nM, as measured by surface plasmon resonance, e.g., using the assay format as defined in Example 3 herein, or a substantially similar assay.

The present invention also includes antibodies and antigen-binding fragments thereof that bind PD-1 with a dissociative half-life (t½) of greater than about 1.1 minutes as measured by surface plasmon resonance at 25° C. or 37° C., e.g., using an assay format as defined in Example 3 herein, or a substantially similar assay. In certain embodiments, the antibodies or antigen-binding fragments of the present invention bind PD-1 with a t½ of greater than about 5 minutes, greater than about 10 minutes, greater than about 30 minutes, greater than about 50 minutes, greater than about 60 minutes, greater than about 70 minutes, greater than about 80 minutes, greater than about 90 minutes, greater than about 100 minutes, greater than about 200 minutes, greater than about 300 minutes, greater than about 400 minutes, greater than about 500 minutes, greater than about 600 minutes, greater than about 700 minutes, greater than about 800 minutes, greater than about 900 minutes, greater than about 1000 minutes, or greater than about 1200 minutes, as measured by surface plasmon resonance at 25° C. or 37° C., e.g., using an assay format as defined in Example 3 herein (e.g., mAb-capture or antigen-capture format), or a substantially similar assay.

The present invention also includes antibodies or antigen-binding fragments thereof that block PD-1 binding to PD-L1 with an IC50 of less than about 3 nM as determined using a ELISA-based immunoassay assay, e.g., as shown in Example 4, or a substantially similar assay. The present invention also includes antibodies and antigen-binding fragments thereof that bind to PD-1 and enhance the binding of PD-1 to PD-L1.

In some embodiments, the antibodies of the present invention may bind to the extracellular domain of PD-1 or to a fragment of the domain. In some embodiments, the antibodies of the present invention may bind to more than one domain (cross-reactive antibodies). In certain embodiments, the antibodies of the present invention may bind to an epitope located in the extracellular domain comprising amino acid residues 21-171 of PD-1 (SEQ ID NO: 327). In one embodiment, the antibodies may bind to an epitope comprising one or more amino acids selected from the group consisting of amino acid residues 1-146 of SEQ ID NOs: 321-324.

In certain embodiments, the antibodies of the present invention may function by blocking or inhibiting the PD-L1-binding activity associated with PD-1 by binding to any other region or fragment of the full length protein, the amino acid sequence of which is shown in SEQ ID NO: 327. In certain embodiments, the antibodies may attenuate or modulate the interaction between PD-1 and PD-L1.

In certain embodiments, the antibodies of the present invention may be bi-specific antibodies. The bi-specific antibodies of the invention may bind one epitope in one domain and may also bind a second epitope in a different domain of PD-1. In certain embodiments, the bi-specific antibodies of the invention may bind two different epitopes in the same domain. In one embodiment, the multi-specific antigen-binding molecule comprises a first binding specificity wherein the first binding specificity comprises the extracellular domain or fragment thereof of PD-L1; and a second binding specificity to another epitope of PD-1.

In one embodiment, the invention provides an isolated fully human monoclonal antibody or antigen-binding fragment thereof that binds to PD-1, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 218, 226, 234, 242, 250, 258, 266, 274, 282, 290, 298, 306, and 314, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, and 202, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 224, 232, 240, 248, 256, 264, 272, 280, 288, 296, 304, 312, and 320, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, and 208, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 220, 228, 236, 244, 252, 260, 268, 276, 284, 292, 300, 308, and 316, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 222, 230, 238, 246, 254, 262, 270, 278, 286, 294, 302, 310, and 318, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, and 204, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, and 206, or a substantially similar sequence thereof having at least 90%, at least 95%, at least 98% or at least 99% sequence identity; (v) is a multi-specific antigen-binding molecule comprising a first binding specificity to PD-1 and a second binding specificity to an antigen selected from the group consisting of PD-1, a tumor specific antigen, an autoimmune tissue specific antigen, a virally infected cell antigen, a different T-cell co-inhibitor, T-cell receptor, and a Fc receptor; (vi) binds to human PD-1 with a $K_D$ of about 28 pM to about 1.5 pM; (vii) binds to cynomolgus PD-1 with a $K_D$ of about 3 nM to about 7.5 pM; (viii) blocks or enhances the binding of PD-1 to PD-L1 with an IC50 about 3.3 nM; (ix) blocks PD-1-induced T-cell down regulation and/or rescues T-cell signaling in a T-cell/APC luciferase reporter assay; (x) stimulates T-cell proliferation and activity in a mixed lymphocyte reaction (MLR) assay; (xi) induces IL-2 and/or IFNγ production in a MLR assay; and (xii) suppresses tumor growth and increases survival in subjects with cancer.

In one embodiment, the invention provides an isolated fully human monoclonal antibody or antigen-binding fragment thereof that blocks PD-1 binding to PD-L1, wherein the antibody or fragment thereof exhibits one or more of the following characteristics: (i) comprises a HCVR having an amino acid sequence selected from the group consisting of SEQ ID NO: 130, 162, 234 and 314, or a substantially similar sequence thereof having at least 90%, at least 95%, at least 98% or at least 99% sequence identity; (ii) comprises a LCVR having an amino acid sequence selected from the group consisting of SEQ ID NO: 138, 170, 186, and 202, or a substantially similar sequence thereof having at least 90%, at least 95%, at least 98% or at least 99% sequence identity; (iii) comprises a HCDR3 domain having an amino acid sequence selected from the group consisting of SEQ ID NO: 136, 168, 240, and 320, or a substantially similar sequence thereof having at least 90%, at least 95%, at least 98% or at least 99% sequence identity; and a LCDR3 domain having an amino acid sequence selected from the group consisting of SEQ ID NO: 144, 176, 192, and 208, or a substantially similar sequence thereof having at least 90%, at least 95%, at least 98% or at least 99% sequence identity; (iv) comprises a HCDR1 domain having an amino acid sequence selected from the group consisting of SEQ ID NO: 132, 164, 236, and 316, or a substantially similar sequence thereof having at least 90%, at least 95%, at least 98% or at least 99% sequence identity; a HCDR2 domain having an amino acid sequence selected from the group consisting of SEQ ID NO: 134, 166, 238, and 318, or a substantially similar sequence thereof having at least 90%, at least 95%, at least 98% or at least 99% sequence identity; a LCDR1 domain having an amino acid sequence selected from the group consisting of SEQ ID NO: 140, 172, 188, and 204, or a substantially similar sequence thereof having at least 90%, at least 95%, at least 98% or at least 99% sequence identity; and a LCDR2 domain having an amino acid sequence selected from the group consisting of SEQ ID NO: 142, 174, 190, and 206, or a substantially similar sequence thereof having at least 90%, at least 95%, at least 98% or at least 99% sequence identity; (v) is a multi-specific antigen-binding molecule comprising a first binding specificity to PD-1 and a second binding specificity to an antigen selected from the group consisting of a different epitope of PD-1, a tumor specific antigen, an autoimmune tissue specific antigen, a virally infected cell antigen, a different T-cell co-inhibitor, T-cell receptor, and a Fc receptor; (vi) binds to human PD-1 with a $K_D \leq 10^{-9}$M; (vii) binds to cynomolgus PD-1 with a $K_D \leq 10^{-8}$M; (viii) blocks the binding of PD-1 to PD-L1 with an IC50≤$10^{-10}$M; (ix) blocks PD-1-induced T-cell down regulation and/or rescues T-cell signaling in a T-cell/APC luciferase reporter assay; (x) stimulates T-cell proliferation and activity in a mixed lymphocyte reaction (MLR) assay; (xi) induces IL-2 and/or IFNγ production in a MLR assay; and (xii) suppresses tumor growth and increases survival in subjects with cancer.

The antibodies of the present invention may possess one or more of the aforementioned biological characteristics, or any combinations thereof. Other biological characteristics of the antibodies of the present invention will be evident to a person of ordinary skill in the art from a review of the present disclosure including the working Examples herein.

Species Selectivity and Species Cross-Reactivity

According to certain embodiments of the invention, the anti-PD-1 antibodies bind to human PD-1 but not to PD-1 from other species. Alternatively, the anti-PD-1 antibodies of the invention, in certain embodiments, bind to human PD-1 and to PD-1 from one or more non-human species. For example, the anti-PD-1 antibodies of the invention may bind to human PD-1 and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee PD-1. In certain embodiments, the anti-PD-1 antibodies of the invention may bind to human and cynomolgus PD-1 with the same affinities or with different affinities, but do not bind to rat and mouse PD-1.

Epitope Mapping and Related Technologies

The present invention includes anti-PD-1 antibodies which interact with one or more amino acids found within one or more domains of the PD-1 molecule including, e.g., extracellular (IgV-like) domain, a transmembrane domain, and an intracellular domain containing the immunoreceptor tyrosine-based inhibition motif (ITIM) and immunoreceptor tyrosine-based switch motif (ITSM). The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned domains of the PD-1 molecule (e.g. a linear epitope in a domain). Alternatively, the epitope may consist of a plurality of non-contiguous amino acids (or amino acid sequences) located within either or both of the aforementioned domains of the PD-1 molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the anti-PD-1 antibodies or antigen-binding fragments thereof bind an epitope within any one or more of the regions exemplified in PD-1, either in natural form, as exemplified in SEQ ID NO: 327, or recombinantly produced, as exemplified in SEQ ID NOS: 321-324, or to a fragment thereof. In some embodiments, the antibodies of the invention bind to an extracellular region comprising one or more amino acids selected from the group consisting of amino acid residues 21-171 of PD-1. In some embodiments, the antibodies of the invention bind to an extracellular region comprising one or more amino acids selected from the group consisting of amino acid residues 1-146 of cynomolgus PD-1, as exemplified by SEQ ID NO: 322.

In certain embodiments, the antibodies of the invention, as shown in Table 1, interact with at least one amino acid sequence selected from the group consisting of amino acid residues ranging from about position 21 to about position 136 of SEQ ID NO: 327; or amino acid residues ranging from about position 136 to about position 171 of SEQ ID NO: 327. These regions are partially exemplified in SEQ ID NOs: 321-324.

The present invention includes anti-PD-1 antibodies that bind to the same epitope, or a portion of the epitope, as any of the specific exemplary antibodies described herein in Table 1, or an antibody having the CDR sequences of any of the exemplary antibodies described in Table 1. Likewise, the present invention also includes anti-PD-1 antibodies that compete for binding to PD-1 or a PD-1 fragment with any of the specific exemplary antibodies described herein in Table 1, or an antibody having the CDR sequences of any of the exemplary antibodies described in Table 1. For example, the present invention includes anti-PD-1 antibodies that cross-compete for binding to PD-1 with one or more antibodies as defined in Example 6 herein (e.g., H2aM7788N, H4xH8992P, H4xH8999P, H1M7799N, H2aM7780N, H1M7800N, H2aM7794N, H2aM7798N, H4xH9145P2, H4H9057P2, H4xH9120P2, H4xH9128P2, H4H9019P, H4xH9119P2, H4xH9135P2, H4xH9034P, H2aM7790N, H4xH9035P, H4xH9037P, H4xH9045P and H2aM7795N).

One can easily determine whether an antibody binds to the same epitope as, or competes for binding with, a reference anti-PD-1 antibody by using routine methods known in the art. For example, to determine if a test antibody binds to the same epitope as a reference anti-PD-1 antibody of the invention, the reference antibody is allowed to bind to a PD-1 protein or peptide under saturating conditions. Next, the ability of a test antibody to bind to the PD-1 molecule is assessed. If the test antibody is able to bind to PD-1 following saturation binding with the reference anti-PD-1 antibody, it can be concluded that the test antibody binds to a different epitope than the reference anti-PD-1 antibody. On the other hand, if the test antibody is not able to bind to the PD-1 protein following saturation binding with the reference anti-PD-1 antibody, then the test antibody may bind to the same epitope as the epitope bound by the reference anti-PD-1 antibody of the invention.

To determine if an antibody competes for binding with a reference anti-PD-1 antibody, the above-described binding methodology is performed in two orientations: In a first orientation, the reference antibody is allowed to bind to a PD-1 protein under saturating conditions followed by assessment of binding of the test antibody to the PD-1 molecule. In a second orientation, the test antibody is allowed to bind to a PD-1 molecule under saturating conditions followed by assessment of binding of the reference antibody to the PD-1 molecule. If, in both orientations, only the first (saturating) antibody is capable of binding to the PD-1 molecule, then it is concluded that the test antibody and the reference antibody compete for binding to PD-1. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-PD-1 monoclonal antibody conjugated to a therapeutic moiety ("immunoconjugate"), such as a cytotoxin or a chemotherapeutic agent to treat cancer. As used herein, the term "immunoconjugate" refers to an antibody which is chemically or biologically linked to a cytotoxin, a radioactive agent, a cytokine, an interferon, a target or reporter moiety, an enzyme, a toxin, a peptide or protein or a therapeutic agent. The antibody may be linked to the cytotoxin, radioactive agent, cytokine, interferon, target or reporter moiety, enzyme, toxin, peptide or therapeutic agent at any location along the molecule so long as it is able to bind its target. Examples of immunoconjugates include antibody drug conjugates and antibody-toxin fusion proteins. In one embodiment, the agent may be a second different antibody to PD-1. In certain embodiments, the antibody may be conjugated to an agent specific for a tumor cell or a virally infected cell. The type of therapeutic moiety that may be conjugated to the anti-PD-1 antibody and will take into account the condition to be treated and the desired therapeutic effect to be achieved. Examples of suitable agents for forming immunoconjugates are known in the art; see for example, WO 05/103081.

Multi-Specific Antibodies

The antibodies of the present invention may be mono-specific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244.

In one aspect, the present invention includes multi-specific antigen-binding molecules or antigen-binding fragments thereof wherein one specificity of an immunoglobulin is specific for the extracellular domain of PD-1, or a fragment thereof, and the other specificity of the immunoglobulin is specific for binding outside the extracellular domain of PD-1, or a second therapeutic target, or is conjugated to a therapeutic moiety. In certain embodiments, the first antigen-binding specificity may comprise PD-L1 or PD-L2, or a fragment thereof. In certain embodiments of the invention, one specificity of an immunoglobulin is specific for an epitope comprising amino acid residues 21-171 of PD-1 (SEQ ID NO: 327) or a fragment thereof, and the other specificity of the immunoglobulin is specific for a second target antigen. The second target antigen may be on the same cell as PD-1 or on a different cell. In one embodiment, the second target cell is on an immune cell other than a T-cell such as a B-cell, antigen-presenting cell, monocyte, macrophage, or dendritic cell. In some embodiments, the second target antigen may be present on a tumor cell or an autoimmune tissue cell or on a virally infected cell.

In another aspect, the invention provides multi-specific antigen-binding molecules or antigen-binding fragments thereof comprising a first antigen-binding specificity that binds to PD-1 and a second antigen-binding specificity that binds to a T-cell receptor, a B-cell receptor or a Fc receptor. In a related aspect, the invention provides multi-specific antigen-binding molecules or antigen-binding fragments thereof comprising a first antigen-binding specificity that binds to PD-1 and a second antigen-binding specificity that binds to a different T-cell co-inhibitor such as LAG-3, CTLA-4, BTLA, CD-28, 2B4, LY108, TIGIT, TIM3, LAIR1, ICOS and CD160.

In another aspect, the invention provides multi-specific antigen-binding molecules or antigen-binding fragments thereof comprising a first antigen-binding specificity that binds to PD-1 and a second antigen-binding specificity that binds to an autoimmune tissue-specific antigen. In certain embodiments, the antibodies may be activating or agonist antibodies.

Any of the multi-specific antigen-binding molecules of the invention, or variants thereof, may be constructed using standard molecular biological techniques (e.g., recombinant DNA and protein expression technology), as will be known to a person of ordinary skill in the art.

In some embodiments, PD-1-specific antibodies are generated in a bi-specific format (a "bi-specific") in which variable regions binding to distinct domains of PD-1 are linked together to confer dual-domain specificity within a single binding molecule. Appropriately designed bi-specifics may enhance overall PD-1 inhibitory efficacy through increasing both specificity and binding avidity. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind more than one domains and a second target, such as, but not limited to, for example, a second different anti-PD-1 antibody, may be prepared in a bi-specific format using techniques described herein, or other techniques known to those skilled in the art. Antibody variable regions binding to distinct regions may be linked together with variable regions that bind to relevant sites on, for example, the extracellular domain of PD-1, to confer dual-antigen specificity within a single binding molecule. Appropriately designed bi-specifics of this nature serve a dual function. Variable regions with specificity for the extracellular domain are combined with a variable region with specificity for outside the extracellular domain and are paired on a structural scaffold that allows each variable region to bind to the separate antigens.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mabe bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Administration and Formulations

The invention provides therapeutic compositions comprising the anti-PD-1 antibodies or antigen-binding fragments thereof of the present invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When an antibody of the present invention is used for treating a disease or disorder in an adult patient, or for preventing such a disease, it is advantageous to administer the antibody of the present invention normally at a single dose of about 0.1 to about 60 mg/kg body weight, more preferably about 5 to about 60, about 10 to about 50, or about 20 to about 50 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389), incorporated herein by reference. Nanoparticles may be developed and conjugated to antibodies contained in pharmaceutical compositions to target tumor cells or autoimmune tissue cells or virally infected cells. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 100 mg and in about 10 to about 250 mg for the other dosage forms.

Therapeutic Uses of the Antibodies

The antibodies of the invention are useful, inter alia, for the treatment, prevention and/or amelioration of any disease or disorder associated with or mediated by PD-1 expression, signaling, or activity, or treatable by blocking the interaction between PD-1 and a PD-1 ligand (e.g., PD-L1, or PD-L2) or otherwise inhibiting PD-1 activity and/or signaling. For example, the present invention provides methods for treating cancer (tumor growth inhibition), chronic viral infections and/or autoimmune disease by administering an anti-PD-1 antibody (or pharmaceutical composition comprising an anti-PD-1 antibody) as described herein to a patient in need of such treatment. The antibodies of the present invention are useful for the treatment, prevention, and/or amelioration of disease or disorder or condition such as cancer, autoimmune disease or a viral infection and/or for ameliorating at least one symptom associated with such disease, disorder or condition. In the context of the methods of treatment described herein, the anti-PD-1 antibody may be administered as a monotherapy (i.e., as the only therapeutic agent) or in combination with one or more additional therapeutic agents (examples of which are described elsewhere herein).

In some embodiments of the invention, the antibodies described herein are useful for treating subjects suffering from primary or recurrent cancer, including, but not limited to, renal cell carcinoma, colorectal cancer, non-small-cell lung cancer, brain cancer (e.g., glioblastoma multiforme), squamous cell carcinoma of head and neck, gastric cancer, prostate cancer, ovarian cancer, kidney cancer, breast cancer, multiple myeloma, and melanoma.

The antibodies may be used to treat early stage or late-stage symptoms of cancer. In one embodiment, an antibody or fragment thereof of the invention may be used to treat metastatic cancer. The antibodies are useful in reducing or inhibiting or shrinking tumor growth of both solid tumors and blood cancers. In certain embodiments, treatment with an antibody or antigen-binding fragment thereof of the invention leads to more than 50% regression, more than 60% regression, more than 70% regression, more than 80% regression or more than 90% regression of a tumor in a subject. In certain embodiments, the antibodies may be used to prevent relapse of a tumor. In certain embodiments, the antibodies are useful in extending overall survival in a subject with cancer. In some embodiments, the antibodies are useful in reducing toxicity due to chemotherapy or radiotherapy while maintaining long-term survival in a patient suffering from cancer.

In certain embodiments, the antibodies of the invention are useful to treat subjects suffering from a chronic viral infection. In some embodiments, the antibodies of the invention are useful in decreasing viral titers in the host and/or rescuing exhausted T-cells. In certain embodiments, an antibody or fragment thereof of the invention may be used to treat chronic viral infection by lymphocytic choriomeningitis virus (LCMV). In some embodiments, an antibody or antigen-binding fragment thereof the invention may be administered at a therapeutic dose to a patient with an infection by human immunodeficiency virus (HIV) or human papilloma virus (HPV) or hepatitis B/C virus (HBV/HCV). In a related embodiment, an antibody or antigen-binding fragment thereof of the invention may be used to treat an infection by simian immunodeficiency virus (SIV) in a simian subject such as cynomolgus.

In certain embodiments, a blocking antibody of the present invention may be administered in a therapeutically effective amount to a subject suffering from a cancer or a viral infection.

In certain embodiments, the antibodies of the invention are useful for treating an autoimmune disease, including but not limited to, alopecia areata, autoimmune hepatitis, celiac disease, Graves' disease, Guillain-Barre syndrome, Hashimoto's disease, hemolytic anemia, inflammatory bowel disease, inflammatory myopathies, multiple sclerosis, primary biliary cirrhosis, psoriasis, rheumatoid arthritis, scleroderma, Sjögren's syndrome, systemic lupus erthyematosus, vitiligo, autoimmune pancreatitis, autoimmune urticaria, autoimmune thrombocytopenic purpura, Crohn's disease, diabetes type I, eosinophilic fasciitis, eosinophilic enterogastritis, Goodpasture's syndrome, myasthenia gravis, psoriatic arthritis, rheumatic fever, ulcerative colitis, vasculitis and Wegener's granulomatosis. In certain embodiments, an activating antibody of the invention may be used to treat a subject suffering from autoimmune disease.

One or more antibodies of the present invention may be administered to relieve or prevent or decrease the severity of one or more of the symptoms or conditions of the disease or disorder.

It is also contemplated herein to use one or more antibodies of the present invention prophylactically to patients at risk for developing a disease or disorder such as cancer, autoimmune disease and chronic viral infection.

In a further embodiment of the invention the present antibodies are used for the preparation of a pharmaceutical composition for treating patients suffering from cancer, autoimmune disease or viral infection. In another embodiment of the invention, the present antibodies are used as adjunct therapy with any other agent or any other therapy known to those skilled in the art useful for treating cancer, autoimmune disease or viral infection.

Combination Therapies and Formulations

Combination therapies may include an anti-PD-1 antibody of the invention and any additional therapeutic agent that may be advantageously combined with an antibody of the invention, or with a biologically active fragment of an antibody of the invention.

The antibodies of the present invention may be combined synergistically with one or more anti-cancer drugs or therapy used to treat cancer, including, for example, renal cell carcinoma, colorectal cancer, glioblastoma multiforme, squamous cell carcinoma of head and neck, non-small-cell lung cancer, colon cancer, ovarian cancer, adenocarcinoma, prostate cancer, glioma, and melanoma. It is contemplated herein to use anti-PD-1 antibodies of the invention in combination with immunostimulatory and/or immunosupportive therapies to inhibit tumor growth, and/or enhance survival of cancer patients. The immunostimulatory therapies include direct immunostimulatory therapies to augment immune cell activity by either "releasing the brake" on suppressed immune cells or "stepping on the gas" to activate an immune response. Examples include targeting other checkpoint receptors, vaccination and adjuvants. The immunosupportive modalities may increase antigenicity of the tumor by promoting immunogenic cell death, inflammation or have other indirect effects that promote an anti-tumor immune response. Examples include radiation, chemotherapy, anti-angiogenic agents, and surgery.

In various embodiments, one or more antibodies of the present invention may be used in combination with an antibody to PD-L1, a second antibody to PD-1 (e.g., nivolumab), a LAG-3 inhibitor, a CTLA-4 inhibitor (e.g., ipilimumab), a TIM3 inhibitor, a BTLA inhibitor, a TIGIT inhibitor, a CD47 inhibitor, an antagonist of another T-cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), an agonist to a co-stimulatory receptor (e.g., an agonist to glucocorticoid-induced TNFR-related protein), an antibody to a tumor-specific antigen (e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9), a vaccine (e.g., *Bacillus* Calmette-Guerin, a cancer vaccine), an adjuvant to increase antigen presentation (e.g., granulocyte-macrophage colony-stimulating factor), a bispecific antibody (e.g., CD3xCD20 bispecific antibody, PSMAxCD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), an anti-inflammatory drug (e.g., corticosteroids, and non-steroidal anti-inflammatory drugs), a dietary supplement such as anti-oxidants or any palliative care to treat cancer. In certain embodiments, the anti-PD-1 antibodies of the present invention may be used in combination with cancer vaccines including dendritic cell vaccines, oncolytic viruses, tumor cell vaccines, etc. to augment the anti-tumor response. Examples of cancer vaccines that can be used in combination with anti-PD-1 antibodies of the present invention include MAGE3 vaccine for melanoma and bladder cancer, MUC1 vaccine for breast cancer, EGFRv3 (e.g., Rindopepimut) for brain cancer (including glioblastoma multiforme), or ALVAC-CEA (for CEA+ cancers).

In certain embodiments, the anti-PD-1 antibodies of the invention may be administered in combination with radiation therapy in methods to generate long-term durable anti-tumor responses and/or enhance survival of patients with cancer. In some embodiments, the anti-PD-1 antibodies of the invention may be administered prior to, concomitantly or after administering radiation therapy to a cancer patient. For example, radiation therapy may be administered in one or more doses to tumor lesions followed by administration of one or more doses of anti-PD-1 antibodies of the invention. In some embodiments, radiation therapy may be administered locally to a tumor lesion to enhance the local immunogenicity of a patient's tumor (adjuvinating radiation) and/or to kill tumor cells (ablative radiation) followed by systemic administration of an anti-PD-1 antibody of the invention. For example, intracranial radiation may be administered to a patient with brain cancer (e.g., glioblastoma multiforme) in combination with systemic administration of an anti-PD-1 antibody of the invention. In certain embodiments, the anti-PD-1 antibodies of the invention may be administered in combination with radiation therapy and a chemotherapeutic agent (e.g., temozolomide) or a VEGF antagonist (e.g., aflibercept).

In certain embodiments, the anti-PD-1 antibodies of the invention may be administered in combination with one or more anti-viral drugs to treat chronic viral infection caused by LCMV, HIV, HPV, HBV or HCV. Examples of anti-viral drugs include, but are not limited to, zidovudine, lamivudine, abacavir, ribavirin, lopinavir, efavirenz, cobicistat, tenofovir, rilpivirine and corticosteroids. In some embodiments, the anti-PD-1 antibodies of the invention may be administered in combination with a LAG3 inhibitor, a CTLA-4 inhibitor or any antagonist of another T-cell co-inhibitor to treat chronic viral infection.

In certain embodiments, the anti-PD-1 antibodies of the invention may be combined with an antibody to a Fc receptor on immune cells for the treatment of an autoimmune disease. In one embodiment, an antibody or fragment thereof of the invention is administered in combination with an antibody or antigen-binding protein targeted to an antigen specific to autoimmune tissue. In certain embodiments, an antibody or antigen-binding fragment thereof of the invention is administered in combination with an antibody or antigen-binding protein targeted to a T-cell receptor or a B-cell receptor, including but not limited to, Fcα (e.g., CD89), Fcγ (e.g., CD64, CD32, CD16a, and CD16b), CD19, etc. The antibodies of fragments thereof of the invention may be used in combination with any drug or therapy known in the art (e.g., corticosteroids and other immunosuppressants) to treat an autoimmune disease or disorder including, but not limited to alopecia areata, autoimmune hepatitis, celiac disease, Graves' disease, Guillain-Barre syndrome, Hashimoto's disease, hemolytic anemia, inflammatory bowel disease, inflammatory myopathies, multiple sclerosis, primary biliary cirrhosis, psoriasis, rheumatoid arthritis, scleroderma, Sjögren's syndrome, systemic lupus erthyematosus, vitiligo, autoimmune pancreatitis, autoimmune urticaria, autoimmune thrombocytopenic purpura, Crohn's disease, diabetes type I, eosinophilic fasciitis, eosinophilic enterogastritis, Goodpasture's syndrome, myasthenia gravis, psoriatic arthritis, rheumatic fever, ulcerative colitis, vasculitis and Wegener's granulomatosis.

The additional therapeutically active agent(s)/component(s) may be administered prior to, concurrent with, or after the administration of the anti-PD-1 antibody of the present invention. For purposes of the present disclosure, such administration regimens are considered the administration of an anti-PD-1 antibody "in combination with" a second therapeutically active component.

The additional therapeutically active component(s) may be administered to a subject prior to administration of an anti-PD-1 antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-PD-1 antibody of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-PD-1 antibody of the present invention. "Concurrent" administration, for purposes of the present invention, includes, e.g., administration of an anti-PD-1 antibody and an additional therapeutically active component to a subject in a single dosage form (e.g., co-formulated), or in separate dosage forms administered to the subject within about 30 minutes or less of each other. If administered in separate dosage forms, each dosage form may be administered via the same route (e.g., both the anti-PD-1 antibody and the additional therapeutically active component may be administered intravenously, subcutaneously, etc.); alternatively, each dosage form may be administered via a different route (e.g., the anti-PD-1 antibody may be administered intravenously, and the additional therapeutically active component may be administered subcutaneously). In any event, administering the components in a single dosage from, in separate dosage forms by the same route, or in separate dosage forms by different routes are all considered "concurrent administration," for purposes of the present disclosure. For purposes of the present disclosure, administration of an anti-PD-1 antibody "prior to", "concurrent with," or "after" (as those terms are defined herein above) administration of an additional therapeutically active component is considered administration of an anti-PD-1 antibody "in combination with" an additional therapeutically active component).

The present invention includes pharmaceutical compositions in which an anti-PD-1 antibody of the present invention is co-formulated with one or more of the additional therapeutically active component(s) as described elsewhere herein using a variety of dosage combinations.

In exemplary embodiments in which an anti-PD-1 antibody of the invention is administered in combination with a VEGF antagonist (e.g., a VEGF trap such as aflibercept), including administration of co-formulations comprising an anti-PD-1 antibody and a VEGF antagonist, the individual components may be administered to a subject and/or co-formulated using a variety of dosage combinations. For example, the anti-PD-1 antibody may be administered to a subject and/or contained in a co-formulation in an amount selected from the group consisting of 0.01 mg, 0.02 mg, 0.03 mg, 0.04 mg, 0.05 mg, 0.1 mg, 0.2 mg, 0.3 mg, 0.4 mg, 0.5 mg, 0.6 mg, 0.7 mg, 0.8 mg, 0.9 mg, 1.0 mg, 1.5 mg, 2.0 mg, 2.5 mg, 3.0 mg, 3.5 mg, 4.0 mg, 4.5 mg, 5.0 mg, 6.0 mg, 7.0 mg, 8.0 mg, 9.0 mg, and 10.0 mg; and the VEGF antagonist (e.g., a VEGF trap such as aflibercept) may be administered to the subject and/or contained in a co-formulation in an amount selected from the group consisting of 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg and 3.0 mg. The combinations/co-formulations may be administered to a subject according to any of the administration regimens disclosed elsewhere herein, including, e.g., twice a week, once every week, once every 2 weeks, once every 3 weeks, once every month, once every 2 months, once every 3 months, once every 4 months, once every 5 months, once every 6 months, etc.

Administrative Regimens

According to certain embodiments of the present invention, multiple doses of an anti-PD-1 antibody (or a pharmaceutical composition comprising a combination of an anti-PD-1 antibody and any of the additional therapeutically active agents mentioned herein) may be administered to a subject over a defined time course. The methods according to this aspect of the invention comprise sequentially administering to a subject multiple doses of an anti-PD-1 antibody of the invention. As used herein, "sequentially administering" means that each dose of anti-PD-1 antibody is administered to the subject at a different point in time, e.g., on different days separated by a predetermined interval (e.g., hours, days, weeks or months). The present invention includes methods which comprise sequentially administering to the patient a single initial dose of an anti-PD-1 antibody, followed by one or more secondary doses of the anti-PD-1 antibody, and optionally followed by one or more tertiary doses of the anti-PD-1 antibody. The anti-PD-1 antibody may be administered at a dose between 0.1 mg/kg to 100 mg/kg.

The terms "initial dose," "secondary doses," and "tertiary doses," refer to the temporal sequence of administration of the anti-PD-1 antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-PD-1 antibody, but generally may differ from one another in terms of frequency of administration. In certain embodiments, however, the amount of anti-PD-1 antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-PD-1 antibody which is administered to a patient prior to the administration of the very next dose in the sequence with no intervening doses.

The methods according to this aspect of the invention may comprise administering to a patient any number of secondary and/or tertiary doses of an anti-PD-1 antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the invention, if the loading doses are administered at a frequency of, e.g., once a month (e.g., two, three, four, or more loading doses administered once a month), then the maintenance doses may be administered to the patient once every five weeks, once every six weeks, once every seven weeks, once every eight weeks, once every ten weeks, once every twelve weeks, etc.).

Diagnostic Uses of the Antibodies

The anti-PD-1 antibodies of the present invention may be used to detect and/or measure PD-1 in a sample, e.g., for diagnostic purposes. Some embodiments contemplate the use of one or more antibodies of the present invention in assays to detect a disease or disorder such as cancer, autoimmune disease or chronic viral infection. Exemplary diagnostic assays for PD-1 may comprise, e.g., contacting a sample, obtained from a patient, with an anti-PD-1 antibody of the invention, wherein the anti-PD-1 antibody is labeled with a detectable label or reporter molecule or used as a capture ligand to selectively isolate PD-1 from patient samples. Alternatively, an unlabeled anti-PD-1 antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure PD-1 in a sample include enzyme-linked immunosorbent assay (ELISA), radioimmunoassay (RIA), and fluorescence-activated cell sorting (FACS).

Samples that can be used in PD-1 diagnostic assays according to the present invention include any tissue or fluid sample obtainable from a patient, which contains detectable quantities of either PD-1 protein, or fragments thereof, under normal or pathological conditions. Generally, levels of PD-1 in a particular sample obtained from a healthy patient (e.g., a patient not afflicted with cancer or an autoimmune disease) will be measured to initially establish a baseline, or standard, level of PD-1. This baseline level of PD-1 can then be compared against the levels of PD-1 measured in samples obtained from individuals suspected of having a cancer-related condition, or symptoms associated with such condition.

The antibodies specific for PD-1 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

Aspects of the invention relate to use of the disclosed antibodies as markers for predicting prognosis of cancer or an autoimmune disorder in patients. Antibodies of the present invention may be used in diagnostic assays to evaluate prognosis of cancer in a patient and to predict survival.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1

Generation of Human Antibodies to PD-1

Human antibodies to PD-1 were generated using a fragment of PD-1 that ranges from about amino acids 25-170 of GenBank Accession NP_005009.2 (SEQ ID NO: 327) with a C93S change. The immunogen was administered directly, with an adjuvant to stimulate the immune response, to a VELOCIMMUNE® mouse comprising DNA encoding human Immunoglobulin heavy and kappa light chain variable regions. The antibody immune response was monitored by a PD-1-specific immunoassay. When a desired immune response was achieved splenocytes were harvested and fused with mouse myeloma cells to preserve their viability and form hybridoma cell lines. The hybridoma cell lines were screened and selected to identify cell lines that produce PD-1-specific antibodies. Using this technique, and the immunogen described above, several anti-PD-1 chimeric antibodies (i.e., antibodies possessing human variable domains and mouse constant domains) were obtained; exemplary antibodies generated in this manner were designated as H1M7789N, H1M7799N, H1M7800N, H2M7780N, H2M7788N, H2M7790N, H2M7791N, H2M7794N, H2M7795N, H2M7796N, and H2M7798N.

Anti-PD-1 antibodies were also isolated directly from antigen-positive B cells without fusion to myeloma cells, as described in U.S. 2007/0280945A1, herein specifically incorporated by reference in its entirety. Using this method, several fully human anti-PD-1 antibodies (i.e., antibodies possessing human variable domains and human constant domains) were obtained; exemplary antibodies generated in this manner were designated as follows: H4H9019P, H4xH9034P2, H4xH9035P2, H4xH9037P2, H4xH9045P2, H4xH9048P2, H4H9057P2, H4H9068P2, H4xH9119P2, H4xH9120P2, H4xH9128P2, H4xH9135P2, H4xH9145P2, H4xH8992P, H4xH8999P, and H4xH9008P.

The biological properties of the exemplary antibodies generated in accordance with the methods of this Example are described in detail in the Examples set forth below.

Example 2

Heavy and Light Chain Variable Region Amino Acid and Nucleotide Sequences

Table 1 sets forth the amino acid sequence identifiers of the heavy and light chain variable regions and CDRs of selected anti-PD-1 antibodies of the invention. The corresponding nucleic acid sequence identifiers are set forth in Table 2.

TABLE 1

Amino Acid Sequence Identifiers

| Antibody | SEQ ID NOs: | | | | | | | |
|---|---|---|---|---|---|---|---|---|
| Designation | HCVR | HCDR1 | HCDR2 | HCDR3 | LCVR | LCDR1 | LCDR2 | LCDR3 |
| H1M7789N | 2 | 4 | 6 | 8 | 10 | 12 | 14 | 16 |
| H1M7799N | 18 | 20 | 22 | 24 | 26 | 28 | 30 | 32 |
| H1M7800N | 34 | 36 | 38 | 40 | 42 | 44 | 46 | 48 |
| H2M7780N | 50 | 52 | 54 | 56 | 58 | 60 | 62 | 64 |
| H2M7788N | 66 | 68 | 70 | 72 | 74 | 76 | 78 | 80 |
| H2M7790N | 82 | 84 | 86 | 88 | 90 | 92 | 94 | 96 |
| H2M7791N | 98 | 100 | 102 | 104 | 106 | 108 | 110 | 112 |
| H2M7794N | 114 | 116 | 118 | 120 | 122 | 124 | 126 | 128 |
| H2M7795N | 130 | 132 | 134 | 136 | 138 | 140 | 142 | 144 |
| H2M7796N | 146 | 148 | 150 | 152 | 154 | 156 | 158 | 160 |
| H2M7798N | 162 | 164 | 166 | 168 | 170 | 172 | 174 | 176 |
| H4H9019P | 178 | 180 | 182 | 184 | 186 | 188 | 190 | 192 |
| H4xH9034P2 | 194 | 196 | 198 | 200 | 202 | 204 | 206 | 208 |
| H4xH9035P2 | 210 | 212 | 214 | 216 | 202 | 204 | 206 | 208 |
| H4xH9037P2 | 218 | 220 | 222 | 224 | 202 | 204 | 206 | 208 |
| H4xH9045P2 | 226 | 228 | 230 | 232 | 202 | 204 | 206 | 208 |
| H4xH9048P2 | 234 | 236 | 238 | 240 | 202 | 204 | 206 | 208 |
| H4H9057P2 | 242 | 244 | 246 | 248 | 202 | 204 | 206 | 208 |
| H4H9068P2 | 250 | 252 | 254 | 256 | 202 | 204 | 206 | 208 |
| H4xH9119P2 | 258 | 260 | 262 | 264 | 202 | 204 | 206 | 208 |
| H4xH9120P2 | 266 | 268 | 270 | 272 | 202 | 204 | 206 | 208 |
| H4xH9128P2 | 274 | 276 | 278 | 280 | 202 | 204 | 206 | 208 |
| H4xH9135P2 | 282 | 284 | 286 | 288 | 202 | 204 | 206 | 208 |
| H4xH9145P2 | 290 | 292 | 294 | 296 | 202 | 204 | 206 | 208 |
| H4xH8992P | 298 | 300 | 302 | 304 | 186 | 188 | 190 | 192 |
| H4xH8999P | 306 | 308 | 310 | 312 | 186 | 188 | 190 | 192 |
| H4xH9008P | 314 | 316 | 318 | 320 | 186 | 188 | 190 | 192 |

TABLE 2

Nucleic Acid Sequence Identifiers

| Antibody | SEQ ID NOs: | | | | | | | |
|---|---|---|---|---|---|---|---|---|
| Designation | HCVR | HCDR1 | HCDR2 | HCDR3 | LCVR | LCDR1 | LCDR2 | LCDR3 |
| H1M7789N | 1 | 3 | 5 | 7 | 9 | 11 | 13 | 15 |
| H1M7799N | 17 | 19 | 21 | 23 | 25 | 27 | 29 | 31 |
| H1M7800N | 33 | 35 | 37 | 39 | 41 | 43 | 45 | 47 |
| H2M7780N | 49 | 51 | 53 | 55 | 57 | 59 | 61 | 63 |
| H2M7788N | 65 | 67 | 69 | 71 | 73 | 75 | 77 | 79 |
| H2M7790N | 81 | 83 | 85 | 87 | 89 | 91 | 93 | 95 |
| H2M7791N | 97 | 99 | 101 | 103 | 105 | 107 | 109 | 111 |
| H2M7794N | 113 | 115 | 117 | 119 | 121 | 123 | 125 | 127 |
| H2M7795N | 129 | 131 | 133 | 135 | 137 | 139 | 141 | 143 |
| H2M7796N | 145 | 147 | 149 | 151 | 153 | 155 | 157 | 159 |
| H2M7798N | 161 | 163 | 165 | 167 | 169 | 171 | 173 | 175 |
| H4H9019P | 177 | 179 | 181 | 183 | 185 | 187 | 189 | 191 |
| H4xH9034P2 | 193 | 195 | 197 | 199 | 201 | 203 | 205 | 207 |
| H4xH9035P2 | 209 | 211 | 213 | 215 | 201 | 203 | 205 | 207 |
| H4xH9037P2 | 217 | 219 | 221 | 223 | 201 | 203 | 205 | 207 |
| H4xH9045P2 | 225 | 227 | 229 | 231 | 201 | 203 | 205 | 207 |
| H4xH9048P2 | 233 | 235 | 237 | 239 | 201 | 203 | 205 | 207 |
| H4H9057P2 | 241 | 243 | 245 | 247 | 201 | 203 | 205 | 207 |
| H4H9068P2 | 249 | 251 | 253 | 255 | 201 | 203 | 205 | 207 |

TABLE 2-continued

| Nucleic Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H4xH9119P2 | 257 | 259 | 261 | 263 | 201 | 203 | 205 | 207 |
| H4xH9120P2 | 265 | 267 | 269 | 271 | 201 | 203 | 205 | 207 |
| H4xH9128P2 | 273 | 275 | 277 | 279 | 201 | 203 | 205 | 207 |
| H4xH9135P2 | 281 | 283 | 285 | 287 | 201 | 203 | 205 | 207 |
| H4xH9145P2 | 289 | 291 | 293 | 295 | 201 | 203 | 205 | 207 |
| H4xH8992P | 297 | 299 | 301 | 303 | 185 | 187 | 189 | 191 |
| H4xH8999P | 305 | 307 | 309 | 311 | 185 | 187 | 189 | 191 |
| H4xH9008P | 313 | 315 | 317 | 319 | 185 | 187 | 189 | 191 |

Antibodies are typically referred to herein according to the following nomenclature: Fc prefix (e.g. "H4xH," "H1M," "H2M," etc.), followed by a numerical identifier (e.g. "7789," "7799," etc., as shown in Table 1), followed by a "P," "P2," "N," or "B" suffix. Thus, according to this nomenclature, an antibody may be referred to herein as, e.g., "H1H7789N," "H1M7799N," "H2M7780N," etc. The H4xH, HIM, H2M and H2aM prefixes on the antibody designations used herein indicate the particular Fc region isotype of the antibody. For example, an "H4xH" antibody has a human IgG4 Fc with 2 or more amino acid changes as disclosed in US20100331527, an "H1M" antibody has a mouse IgG1 Fc, and an "H2M" antibody has a mouse IgG2 Fc (a or b isotype) (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 1—will remain the same, and the binding properties to antigen are expected to be identical or substantially similar regardless of the nature of the Fc domain.

In certain embodiments, selected antibodies with a mouse IgG1 Fc were converted to antibodies with human IgG4 Fc. In one embodiment, the IgG4 Fc domain comprises a serine to proline mutation in the hinge region (S108P) to promote dimer stabilization. Table 3 sets forth the amino acid sequence identifiers of heavy chain and light chain sequences of selected anti-PD-1 antibodies with human IgG4 Fc.

TABLE 3

| Antibody | SEQ ID NOs: | |
|---|---|---|
| Designation | Heavy Chain | Light Chain |
| H4H7798N | 330 | 331 |
| H4H7795N2 | 332 | 333 |
| H4H9008P | 334 | 335 |
| H4H9048P2 | 336 | 337 |

Each heavy chain sequence in Table 3 comprised a variable region ($V_H$ or HCVR; comprising HCDR1, HCDR2 and HCDR3) and a constant region (comprising $C_H1$, $C_H2$ and $C_H3$ domains). Each light chain sequence in Table 3 comprised a variable region ($V_L$ or LCVR; comprising LCDR1, LCDR2 and LCDR3) and a constant region ($C_L$). SEQ ID NO: 330 comprised a HCVR comprising amino acids 1-117 and a constant region comprising amino acids 118-444. SEQ ID NO: 331 comprised a LCVR comprising amino acids 1-107 and a constant region comprising amino acids 108-214. SEQ ID NO: 332 comprised a HCVR comprising amino acids 1-122 and a constant region comprising amino acids 123-449. SEQ ID NO: 333 comprised a LCVR comprising amino acids 1-107 and a constant region comprising amino acids 108-214. SEQ ID NO: 334 comprised a HCVR comprising amino acids 1-119 and a constant region comprising amino acids 120-446. SEQ ID NO: 335 comprised a LCVR comprising amino acids 1-108 and a constant region comprising amino acids 109-215. SEQ ID NO: 336 comprised a HCVR comprising amino acids 1-121 and a constant region comprising amino acids 122-448. SEQ ID NO: 337 comprised a LCVR comprising amino acids 1-108 and a constant region comprising amino acids 109-215.

Example 3

Antibody Binding to PD-1 as Determined by Surface Plasmon Resonance

Binding association and dissociation rate constants ($k_a$ and $k_d$, respectively), equilibrium dissociation constants and dissociation half-lives ($K_D$ and $t_{1/2}$, respectively) for antigen binding to purified anti-PD1 antibodies were determined using a real-time surface plasmon resonance biosensor assay on a Biacore 4000 or Biacore T200 instrument. The Biacore sensor surface was derivatized with either a polyclonal rabbit anti-mouse antibody (GE, #BR-1008-38) or with a monoclonal mouse anti-human Fc antibody (GE, #BR-1008-39) to capture approximately 100-900 RUs of anti-PD-1 monoclonal antibodies, expressed with either a mouse Fc or a human Fc, respectively. The PD-1 reagents tested for binding to the anti-PD-1 antibodies included recombinant human PD-1 expressed with a C-terminal myc-myc-hexahistidine tag (hPD-1-MMH; SEQ ID NO: 321), recombinant cynomolgus monkey PD-1 expressed with a C-terminal myc-myc-hexahistidine tag (MfPD-1-MMH; SEQ ID NO: 322), recombinant human PD-1 dimer expressed with either a C-terminal mouse IgG2a Fc tag (hPD-1-mFc; SEQ ID NO: 323) or with a C-terminal human IgG1 Fc (hPD1-hFc; SEQ ID NO: 324), and monkey PD-1 with mFc (SEQ ID NO: 329). Different concentrations of PD-1 reagents ranging from 200 nM to 3.7 nM were injected over the anti-PD-1 monoclonal antibody captured surface at a flow rate of 30 μL/min on Biacore 4000 or at 50 μL/min on Biacore T200. The binding of the PD-1 reagents to captured monoclonal antibodies was monitored for 3 to 5 minutes while their dissociation from the antibodies was monitored for 7 to 10 minutes in HBST running buffer (0.01 M HEPES pH 7.4, 0.15 M NaCl, 3 mM EDTA, 0.05% v/v Surfactant P20).

Experiments were performed at 25° C. and 37° C. Kinetic association ($k_a$) and dissociation ($k_d$) rate constants were determined by processing and fitting the data to a 1:1 binding model using Scrubber 2.0c curve fitting software. Binding dissociation equilibrium constants ($K_D$) and dissociative half-lives ($t_{1/2}$) were then calculated from the kinetic rate constants as: $K_D$ (M)=$k_d/k_a$ and $t_{1/2}$ (min)=[In2/(60*$k_d$)]. Binding kinetics parameters for different anti-PD-1 monoclonal antibodies binding to different PD-1 reagents at 25° C. and 37° C. are tabulated in Tables 4-11.

TABLE 4

Binding Kinetics parameters of anti-PD-1 monoclonal antibodies binding to human PD-1-MMH at 25° C.

| Antibody | $k_a$ (1/Ms) | $k_d$ (1/s) | $K_D$ (M) | t½ (min) |
|---|---|---|---|---|
| H2aM7780N | 9.32E+03 | 3.59E−04 | 3.85E−08 | 32 |
| H2aM7788N | 1.97E+04 | 3.88E−04 | 1.96E−08 | 30 |
| H1M7789N | 2.53E+04 | 5.31E−05 | 2.10E−09 | 218 |
| H2aM7790N | 4.63E+04 | 8.23E−04 | 1.78E−08 | 14 |
| H2aM7791N | 3.01E+04 | 7.06E−04 | 2.34E−08 | 16 |
| H2aM7794N | 5.50E+04 | 2.12E−03 | 3.80E−08 | 5.4 |
| H2aM7795N | 4.91E+04 | 1.15E−03 | 2.35E−08 | 10 |
| H2aM7796N | 6.73E+03 | 1.93E−03 | 2.86E−07 | 6.0 |
| H2aM7798N | 1.32E+05 | 3.06E−04 | 2.31E−09 | 38 |
| H1M7799N | 5.04E+04 | 1.23E−02 | 2.44E−07 | 0.9 |
| H1M7800N | 5.88E+04 | 9.47E−03 | 1.61E−07 | 1.2 |
| H4H9019P | 2.05E+04 | 8.08E−04 | 3.94E−08 | 14 |
| H4xH9034P | 1.02E+05 | 1.49E−03 | 1.45E−08 | 7.8 |
| H4xH9035P | 1.03E+05 | 4.75E−04 | 4.62E−09 | 24 |
| H4xH9037P | 7.32E+04 | 7.95E−04 | 1.09E−08 | 15 |
| H4xH9045P | 5.40E+04 | 4.03E−03 | 7.46E−08 | 2.9 |
| H4xH9048P2 | 1.37E+05 | 1.23E−03 | 8.95E−09 | 9.4 |
| H4H9057P2 | 4.60E+04 | 1.34E−02 | 2.91E−07 | 0.9 |
| H4H9068P2 | NB* | NB* | NB* | NB* |
| H4xH9119P2 | 7.84E+04 | 1.22E−03 | 1.56E−08 | 9.5 |
| H4xH9120P2 | 3.32E+04 | 9.98E−04 | 3.01E−08 | 12 |
| H4xH9128P2 | 4.95E+04 | 7.19E−04 | 1.45E−08 | 16 |
| H4xH9135P2 | 1.17E+05 | 1.20E−03 | 1.02E−08 | 10 |
| H4xH9145P2 | 3.47E+04 | 1.34E−03 | 3.85E−08 | 8.6 |
| H4xH8992P | 1.50E+05 | 2.13E−02 | 1.41E−07 | 0.5 |
| H4xH8999P | 2.83E+05 | 1.23E−03 | 4.33E−09 | 9.4 |
| H4xH9008P | 4.29E+04 | 1.33E−03 | 3.10E−08 | 8.7 |
| H4H7795N2 | 6.35E+04 | 1.48E−03 | 2.33E−08 | 8 |
| H4H7798N | 1.47E+05 | 4.43E−04 | 3.01E−09 | 26 |

*NB indicates that under the experimental conditions, PD-1 reagent did not bind to the captured anti-PD-1 monoclonal antibody

TABLE 5

Binding Kinetics parameters of anti-PD-1 monoclonal antibodies binding to human PD-1-MMH at 37° C.

| Antibody | $k_a$ (1/Ms) | $k_d$ (1/s) | $K_D$ (M) | t½ (min) |
|---|---|---|---|---|
| H2aM7780N | 2.72E+04 | 1.52E−03 | 5.58E−08 | 7.6 |
| H2aM7788N | 2.88E+04 | 1.49E−03 | 5.19E−08 | 7.7 |
| H1M7789N | 4.53E+04 | 2.95E−04 | 6.52E−09 | 39 |
| H2aM7790N | 6.13E+04 | 5.20E−03 | 8.49E−08 | 2.2 |
| H2aM7791N | 4.18E+04 | 2.24E−03 | 5.35E−08 | 5.2 |
| H2aM7794N | 1.20E+05 | 7.92E−03 | 6.61E−08 | 1.5 |
| H2aM7795N | 6.75E+04 | 4.58E−03 | 6.78E−08 | 2.5 |
| H2aM7796N | 1.09E+04 | 1.65E−02 | 1.51E−06 | 0.7 |
| H2aM7798N | 1.73E+05 | 6.56E−04 | 3.79E−09 | 18 |
| H1M7799N | 7.94E+04 | 4.25E−02 | 5.36E−07 | 0.3 |
| H1M7800N | 7.83E+04 | 3.99E−02 | 5.10E−07 | 0.3 |
| H4H9019P | 1.20E+04 | 5.44E−03 | 4.53E−07 | 2.1 |
| H4xH9034P | 2.79E+05 | 1.12E−02 | 4.02E−08 | 1.0 |
| H4xH9035P | 2.98E+05 | 4.26E−03 | 1.43E−08 | 2.7 |
| H4xH9037P | 2.26E+05 | 6.68E−03 | 2.95E−08 | 1.7 |
| H4xH9045P | 8.04E+04 | 5.32E−02 | 6.62E−07 | 0.2 |
| H4xH9048P2 | 3.70E+05 | 8.60E−03 | 2.32E−08 | 1.3 |
| H4H9057P2 | NB* | NB* | NB* | NB* |
| H4H9068P2 | NB* | NB* | NB* | NB* |
| H4xH9119P2 | 2.40E+05 | 1.04E−02 | 4.35E−08 | 1.1 |
| H4xH9120P2 | 6.88E+04 | 7.01E−03 | 1.02E−07 | 1.6 |
| H4xH9128P2 | 1.04E+05 | 4.36E−03 | 4.20E−08 | 2.6 |
| H4xH9135P2 | 4.18E+05 | 1.11E−02 | 2.66E−08 | 1.0 |
| H4xH9145P2 | 1.31E+05 | 1.23E−02 | 9.40E−08 | 0.9 |
| H4xH8992P | IC* | IC* | IC* | IC* |
| H4xH8999P | 5.99E+05 | 9.42E−03 | 1.57E−08 | 1.2 |
| H4xH9008P | 1.29E+05 | 8.09E−03 | 6.26E−08 | 1.4 |
| H4H7795N2 | 6.41E+04 | 6.64E−03 | 1.04E−07 | 1.7 |
| H4H7798N | 2.27E+05 | 1.70E−03 | 7.48E−09 | 7 |

*NB indicates that under the experimental conditions, PD-1 reagent did not bind to the captured anti-PD-1 monoclonal antibody. IC indicates that under the experimental conditions, PD-1 binding is inconclusive.

TABLE 6

Binding Kinetics parameters of anti-PD-1 monoclonal antibodies binding to human PD-1 dimer (human PD-1-mFc or human PD-1-hFc) at 25° C.

| Antibody | $k_a$ (1/Ms) | $k_d$ (1/s) | $K_D$ (M) | t½ (min) |
|---|---|---|---|---|
| H2aM7780N | 4.21E+04 | 9.94E−06 | 2.36E−10 | 1162 |
| H2aM7788N | 8.94E+04 | 2.82E−05 | 3.15E−10 | 410 |
| H1M7789N | 3.91E+04 | 4.31E−05 | 1.10E−09 | 268 |
| H2aM7790N | 1.86E+05 | 3.02E−05 | 1.62E−10 | 383 |
| H2aM7791N | 4.05E+04 | 1.01E−04 | 2.49E−09 | 114 |
| H2aM7794N | 1.79E+05 | 1.06E−04 | 5.93E−10 | 109 |
| H2aM7795N | 1.38E+05 | 3.14E−05 | 2.27E−10 | 368 |
| H2aM7796N | 2.61E+04 | 8.67E−05 | 3.32E−09 | 133 |
| H2aM7798N | 3.50E+05 | 2.29E−05 | 6.55E−11 | 505 |
| H1M7799N | 2.38E+05 | 8.55E−05 | 3.60E−10 | 135 |
| H1M7800N | 1.52E+05 | 7.72E−05 | 5.09E−10 | 150 |
| H4H9019P | 4.38E+04 | 8.61E−05 | 1.97E−09 | 134 |
| H4xH9034P | 2.15E+05 | 1.51E−04 | 7.01E−10 | 77 |
| H4xH9035P | 2.01E+05 | 1.03E−04 | 5.13E−10 | 112 |
| H4xH9037P | 1.50E+05 | 1.29E−04 | 8.62E−10 | 89 |
| H4xH9045P | 9.13E+04 | 1.60E−04 | 1.75E−09 | 72 |
| H4xH9048P2 | 2.36E+05 | 1.88E−04 | 7.98E−10 | 61 |
| H4H9057P2 | 1.01E+05 | 1.77E−04 | 1.75E−09 | 65 |
| H4H9068P2 | 4.72E+04 | 2.80E−03 | 5.94E−08 | 4 |
| H4xH9119P2 | 1.63E+05 | 1.62E−04 | 9.92E−10 | 71 |
| H4xH9120P2 | 6.52E+04 | 1.19E−04 | 1.82E−09 | 97 |
| H4xH9128P2 | 8.37E+04 | 1.33E−04 | 1.59E−09 | 87 |
| H4xH9135P2 | 2.12E+05 | 1.38E−04 | 6.51E−10 | 84 |
| H4xH9145P2 | 6.58E+04 | 1.58E−04 | 2.40E−09 | 73 |
| H4xH8992P | 2.35E+05 | 1.60E−04 | 6.80E−10 | 72 |
| H4xH8999P | 5.55E+05 | 1.20E−04 | 2.17E−10 | 96 |
| H4xH9008P | 3.52E+04 | 2.80E−05 | 7.96E−10 | 412 |
| H4H7795N2 | 1.50E+05 | 9.25E−05 | 6.15E−10 | 125 |
| H4H7798N | 4.41E+05 | 5.40E−05 | 1.22E−10 | 214 |

TABLE 7

Binding Kinetics parameters of anti-PD-1 monoclonal antibodies binding to human PD-1 dimer (human PD-1-mFc or human PD-1-hFc) at 37° C.

| Antibody | $k_a$ (1/Ms) | $k_d$ (1/s) | $K_D$ (M) | t½ (min) |
|---|---|---|---|---|
| H2aM7780N | 9.94E+04 | 2.29E−05 | 2.30E−10 | 505 |
| H2aM7788N | 1.31E+05 | 2.13E−05 | 1.63E−10 | 542 |
| H1M7789N | 1.09E+05 | ≤1.0E−05 | ≤9.17E−11 | ≥1155 |
| H2aM7790N | 2.01E+05 | 8.49E−05 | 4.22E−10 | 136 |
| H2aM7791N | 4.98E+04 | 1.79E−04 | 3.59E−09 | 65 |
| H2aM7794N | 4.68E+05 | 2.11E−04 | 4.52E−10 | 55 |
| H2aM7795N | 1.65E+05 | 6.13E−05 | 3.71E−10 | 188 |
| H2aM7796N | 2.21E+04 | 4.34E−04 | 1.96E−08 | 27 |
| H2aM7798N | 4.90E+05 | 1.40E−05 | 2.80E−11 | 825 |
| H1M7799N | 4.41E+05 | 1.81E−04 | 4.11E−10 | 64 |

TABLE 7-continued

Binding Kinetics parameters of anti-PD-1 monoclonal antibodies binding to human PD-1 dimer (human PD-1-mFc or human PD-1-hFc) at 37° C.

| Antibody | $k_a$ (1/Ms) | $k_d$ (1/s) | $K_D$ (M) | t½ (min) |
|---|---|---|---|---|
| H1M7800N | 4.00E+05 | 1.81E−04 | 4.50E−10 | 64 |
| H4H9019P | 7.17E+04 | 1.95E−04 | 2.71E−09 | 59 |
| H4xH9034P | 3.02E+05 | 6.30E−04 | 2.09E−09 | 18 |
| H4xH9035P | 3.16E+05 | 5.54E−04 | 1.75E−09 | 21 |
| H4xH9037P | 2.63E+05 | 9.21E−04 | 3.50E−09 | 13 |
| H4xH9045P | 2.14E+05 | 1.10E−03 | 5.13E−09 | 11 |
| H4xH9048P2 | 3.61E+05 | 1.10E−03 | 3.05E−09 | 10 |
| H4H9057P2 | 2.33E+05 | 2.11E−03 | 9.07E−09 | 5 |
| H4H9068P2 | 9.69E+04 | 1.20E−02 | 1.24E−07 | 1 |
| H4xH9119P2 | 2.40E+05 | 9.09E−04 | 3.80E−09 | 13 |
| H4xH9120P2 | 8.08E+04 | 4.82E−04 | 5.96E−09 | 24 |
| H4xH9128P2 | 1.86E+05 | 6.86E−04 | 3.68E−09 | 17 |
| H4xH9135P2 | 3.10E+05 | 7.02E−04 | 2.27E−09 | 16 |
| H4xH9145P2 | 1.60E+05 | 5.71E−04 | 3.58E−09 | 20 |
| H4xH8992P | 3.49E+05 | 1.02E−03 | 2.91E−09 | 11 |
| H4xH8999P | 7.57E+05 | 4.51E−04 | 5.96E−10 | 26 |
| H4xH9008P | 5.52E+04 | ≤1.0E−05 | ≤1.81E−10 | ≥1155 |
| H4H7795N2 | 1.60E+05 | 2.64E−04 | 1.65E−09 | 44 |
| H4H7798N | 6.60E+05 | 1.15E−04 | 1.75E−10 | 100 |

TABLE 8

Binding Kinetics parameters of anti-PD-1 monoclonal antibodies binding to MfPD-1-MMH at 25° C.

| Antibody | $k_a$ (1/Ms) | $k_d$ (1/s) | $K_D$ (M) | t½ (min) |
|---|---|---|---|---|
| H2aM7780N | 1.00E+04 | 3.15E−04 | 3.15E−08 | 37 |
| H2aM7788N | 8.63E+03 | 6.62E−04 | 7.66E−08 | 17 |
| H1M7789N | 1.55E+04 | 1.23E−04 | 7.89E−09 | 94 |
| H2aM7790N | 3.11E+04 | 9.37E−04 | 3.01E−08 | 12 |
| H2aM7791N | 1.61E+04 | 5.53E−04 | 3.44E−08 | 21 |
| H2aM7794N | 3.60E+04 | 5.99E−03 | 1.66E−07 | 1.9 |
| H2aM7795N | 4.44E+04 | 8.89E−04 | 2.01E−08 | 13 |
| H2aM7796N | NB* | NB* | NB* | NB* |
| H2aM7798N | 8.72E+04 | 3.93E−04 | 4.50E−09 | 29 |
| H1M7799N | 5.78E+04 | 1.30E−02 | 2.24E−07 | 0.9 |
| H1M7800N | 5.89E+04 | 1.04E−02 | 1.76E−07 | 1.1 |
| H4H9019P | 1.94E+04 | 8.33E−04 | 4.29E−08 | 14 |
| H4xH9034P | 9.61E+04 | 2.69E−03 | 2.80E−08 | 4.3 |
| H4xH9035P | 9.36E+04 | 4.34E−04 | 4.64E−09 | 27 |
| H4xH9037P | 6.99E+04 | 9.15E−04 | 1.31E−08 | 13 |
| H4xH9045P | 6.25E+04 | 7.05E−03 | 1.13E−07 | 1.6 |
| H4xH9048P2 | 1.28E+05 | 8.97E−04 | 7.00E−09 | 13 |
| H4H9057P2 | 3.46E+04 | 1.91E−02 | 5.51E−07 | 0.6 |
| H4H9068P2 | NB* | NB* | NB* | NB* |
| H4xH9119P2 | 7.50E+04 | 1.66E−03 | 2.22E−08 | 6.9 |
| H4xH9120P2 | 3.17E+04 | 1.08E−03 | 3.41E−08 | 11 |
| H4xH9128P2 | 3.68E+04 | 6.49E−04 | 1.77E−08 | 18 |
| H4xH9135P2 | 1.24E+05 | 1.31E−03 | 1.06E−08 | 8.8 |
| H4xH9145P2 | 2.86E+04 | 1.24E−03 | 4.31E−08 | 9.3 |
| H4xH8992P | 1.88E+05 | 3.76E−02 | 2.00E−07 | 0.3 |
| H4xH8999P | 4.29E+05 | 1.33E−03 | 3.09E−09 | 8.7 |
| H4xH9008P | 1.05E+05 | 2.49E−03 | 2.38E−08 | 4.6 |
| H4H7795N2 | 6.59E+04 | 1.48E−03 | 2.24E−08 | 8 |
| H4H7798N | 1.43E+05 | 5.51E−04 | 3.86E−09 | 21 |

*NB indicates that under the experimental conditions, PD-1 reagent did not bind to the captured anti-PD-1 monoclonal antibody

TABLE 9

Binding Kinetics parameters of anti-PD-1 monoclonal antibodies binding to MfPD-1-MMH at 37° C.

| Antibody | $k_a$ (1/Ms) | $k_d$ (1/s) | $K_D$ (M) | t½ (min) |
|---|---|---|---|---|
| H2aM7780N | 2.29E+04 | 1.38E−03 | 6.05E−08 | 8.3 |
| H2aM7788N | 1.88E+04 | 3.28E−03 | 1.74E−07 | 3.5 |
| H1M7789N | 4.79E+04 | 4.08E−04 | 8.50E−09 | 28 |
| H2aM7790N | 2.55E+04 | 6.93E−03 | 2.71E−07 | 1.7 |
| H2aM7791N | 3.79E+04 | 1.91E−03 | 5.05E−08 | 6.0 |
| H2aM7794N | 6.66E+04 | 2.01E−02 | 3.02E−07 | 0.6 |
| H2aM7795N | 6.47E+04 | 3.89E−03 | 6.02E−08 | 3.0 |
| H2aM7796N | NB* | NB* | NB* | NB* |
| H2aM7798N | 1.42E+05 | 9.93E−04 | 7.00E−09 | 12 |
| H1M7799N | 8.80E+04 | 4.67E−02 | 5.30E−07 | 0.2 |
| H1M7800N | 8.40E+04 | 4.43E−02 | 5.27E−07 | 0.3 |
| H4H9019P | 2.14E+04 | 7.63E−03 | 3.56E−07 | 1.5 |
| H4xH9034P | 2.83E+05 | 2.47E−02 | 8.73E−08 | 0.5 |
| H4xH9035P | 3.06E+05 | 4.29E−03 | 1.40E−08 | 2.7 |
| H4xH9037P | 2.22E+05 | 8.80E−03 | 3.97E−08 | 1.3 |
| H4xH9045P | 1.40E+04 | 1.05E−01 | 7.54E−06 | 0.1 |
| H4xH9048P2 | 4.15E+05 | 6.97E−03 | 1.68E−08 | 1.7 |
| H4H9057P2 | NB* | NB* | NB* | NB* |
| H4H9068P2 | NB* | NB* | NB* | NB* |
| H4xH9119P2 | 2.40E+05 | 1.23E−02 | 5.14E−08 | 0.9 |
| H4xH9120P2 | 6.98E+04 | 7.48E−03 | 1.07E−07 | 1.5 |
| H4xH9128P2 | 9.06E+04 | 4.18E−03 | 4.61E−08 | 2.8 |
| H4xH9135P2 | 4.62E+05 | 1.34E−02 | 2.89E−08 | 0.9 |
| H4xH9145P2 | 1.71E+05 | 1.43E−02 | 8.37E−08 | 0.8 |
| H4xH8992P | IC* | IC* | IC* | IC* |
| H4xH8999P | 9.83E+05 | 9.26E−03 | 9.41E−09 | 1.2 |
| H4xH9008P | 5.86E+05 | 1.38E−02 | 2.35E−08 | 0.8 |
| H4H7795N2 | 7.80E+04 | 6.89E−03 | 8.83E−08 | 1.7 |
| H4H7798N | 2.13E+05 | 2.23E−3 | 1.05E−08 | 5 |

*NB indicates that under the experimental conditions, PD-1 reagent did not bind to the captured anti-PD-1 monoclonal antibody. IC indicates that under the experimental conditions, PD-1 binding is inconclusive.

TABLE 10

Binding Kinetics parameters of anti-PD-1 monoclonal antibodies binding to monkey PD-1 dimer (monkey PD-1-mFc) at 25° C.

| Antibody | Amount of mAb Captured (RU) | 100 nM Monkey PD-1-mFc Bound (RU) | $k_a$ (1/Ms) | $k_d$ (1/s) | $K_D$ (M) | t½ (min) |
|---|---|---|---|---|---|---|
| H4H9019P | 116 | 31 | 4.55E+04 | 8.96E−05 | 1.97E−09 | 129 |
| H4xH9034P | 215 | 95 | 2.03E+05 | 1.66E−04 | 8.18E−10 | 70 |
| H4xH9035P | 153 | 78 | 2.16E+05 | 9.96E−05 | 4.60E−10 | 116 |
| H4xH9037P | 137 | 58 | 1.50E+05 | 1.37E−04 | 9.12E−10 | 84 |
| H4xH9045P | 202 | 78 | 9.78E+04 | 1.68E−04 | 1.72E−09 | 69 |
| H4xH9048P2 | 227 | 115 | 2.43E+05 | 1.84E−04 | 7.54E−10 | 63 |
| H4H9057P2 | 196 | 75 | 1.02E+05 | 3.03E−04 | 2.98E−09 | 38 |
| H4H9068P2 | 178 | 17 | 5.70E+04 | 3.09E−03 | 5.42E−08 | 4 |

TABLE 10-continued

Binding Kinetics parameters of anti-PD-1 monoclonal antibodies binding to monkey PD-1 dimer (monkey PD-1-mFc) at 25° C.

| Antibody | Amount of mAb Captured (RU) | 100 nM Monkey PD-1-mFc Bound (RU) | $k_a$ (1/Ms) | $k_d$ (1/s) | $K_D$ (M) | t½ (min) |
|---|---|---|---|---|---|---|
| H4xH9119P2 | 209 | 83 | 1.63E+05 | 1.72E−04 | 1.05E−09 | 67 |
| H4xH9120P2 | 195 | 52 | 5.84E+04 | 1.12E−04 | 1.91E−09 | 104 |
| H4xH9128P2 | 175 | 64 | 7.87E+04 | 1.24E−04 | 1.57E−09 | 94 |
| H4xH9135P2 | 150 | 74 | 2.38E+05 | 1.43E−04 | 6.02E−10 | 81 |
| H4xH9145P2 | 304 | 84 | 7.24E+04 | 1.50E−04 | 2.08E−09 | 77 |
| H4xH8992P | 260 | 122 | 2.03E+05 | 2.51E−04 | 1.24E−09 | 46 |
| H4xH8999P | 217 | 126 | 5.50E+05 | 1.15E−04 | 2.10E−10 | 100 |
| H4xH9008P | 248 | 93 | 1.20E+05 | 5.77E−05 | 4.80E−10 | 200 |
| H4H7795N2 | 204 | 60 | 1.60E+05 | 9.92E−05 | 6.21E−10 | 116 |
| H4H7798N | 223 | 93 | 4.49E+05 | 6.14E−05 | 1.37E−10 | 188 |

TABLE 11

Binding Kinetics parameters of anti-PD-1 monoclonal antibodies binding to monkey PD-1 dimer (monkey PD-1-mFc) at 37° C.

| Antibody | Amount of mAb Captured (RU) | 100 nM Monkey PD-1-mFc Bound (RU) | $k_a$ (1/Ms) | $k_d$ (1/s) | $K_D$ (M) | t½ (min) |
|---|---|---|---|---|---|---|
| H4H9019P | 89 | 36 | 8.16E+04 | 2.59E−04 | 3.17E−09 | 45 |
| H4xH9034P | 184 | 81 | 3.07E+05 | 7.49E−04 | 2.44E−09 | 15 |
| H4xH9035P | 88 | 40 | 3.67E+05 | 6.23E−04 | 1.70E−09 | 19 |
| H4xH9037P | 55 | 24 | 2.80E+05 | 8.97E−04 | 3.21E−09 | 13 |
| H4xH9045P | 161 | 65 | 2.41E+05 | 1.36E−03 | 5.66E−09 | 8 |
| H4xH9048P2 | 184 | 84 | 4.94E+05 | 1.13E−03 | 2.29E−09 | 10 |
| H4H9057P2 | 105 | 28 | 1.61E+05 | 4.77E−03 | 2.96E−08 | 2.4 |
| H4H9068P2 | 90 | 6 | 1.21E+05 | 1.05E−02 | 8.63E−08 | 1.1 |
| H4xH9119P2 | 98 | 40 | 2.79E+05 | 8.85E−04 | 3.17E−09 | 13 |
| H4xH9120P2 | 141 | 46 | 8.29E+04 | 5.02E−04 | 6.06E−09 | 23 |
| H4xH9128P2 | 148 | 60 | 1.87E+05 | 8.16E−04 | 4.36E−09 | 14 |
| H4xH9135P2 | 106 | 52 | 3.42E+05 | 7.94E−04 | 2.32E−09 | 15 |
| H4xH9145P2 | 284 | 94 | 1.51E+05 | 6.09E−04 | 4.04E−09 | 19 |
| H4xH8992P | 206 | 86 | 3.50E+05 | 1.53E−03 | 4.38E−09 | ‘8 |
| H4xH8999P | 160 | 83 | 7.30E+05 | 5.10E−04 | 7.00E−10 | 23 |
| H4xH9008P | 216 | 98 | 2.04E+05 | 1.00E−05* | 4.90E−11* | 1155* |
| H4H7795N2 | 164 | 47 | 1.70E+05 | 2.90E−04 | 1.71E−09 | 40 |
| H4H7798N | 203 | 88 | 6.30E+05 | 1.27E−04 | 2.02E−10 | 91 |

*indicates that under the current experimental conditions, no dissociation of PD-1 reagent was observed and the value of kd was manually fixed at 1.00E−05

As shown in Table 4, at 25° C., 28 of the 29 anti-PD-1 antibodies of the invention bound to hPD-1-MMH with $K_D$ values ranging from 2.1 nM to 291 nM. One antibody, H4H9068P2, did not demonstrate any measurable binding to hPD-1-MMH at 25° C. As shown in Table 5, at 37° C., 26 of the 29 anti-PD-1 antibodies of the invention bound to hPD-1-MMH with $K_D$ values ranging from 3.79 nM to 1.51 μM. Three antibodies of the invention did not demonstrate any conclusive binding to hPD-1-MMH at 37° C. As shown in Table 6, at 25° C., all 29 anti-PD-1 antibodies of the invention bound to hPD-1 dimer proteins with $K_D$ values ranging from 65.5 pM to 59.4 nM. As shown in Table 7, at 37° C., all 27 anti-PD-1 antibodies of the invention bound to hPD-1 dimer proteins with $K_D$ values ranging from 3.09 μM to 551 nM. As shown in Table 8, at 25° C., 27 of the 29 anti-PD-1 antibodies of the invention bound to MfPD-1-MMH with $K_D$ values ranging from 3.09 nM to 551 nM. Two antibodies of the invention did not demonstrate any conclusive binding to MfPD-1-MMH at 25° C. As shown in Table 9, at 37° C., 25 of the 29 anti-PD-1 antibodies of the invention bound to MfPD-1-MMH with $K_D$ values ranging from 7.00 nM to 7.54 μM. Four antibodies of the invention did not demonstrate any conclusive binding to MfPD-1-MMH at 37° C. As shown in Table 10, at 25° C., all 18 of the tested anti-PD-1 antibodies of the invention bound to MfPD-1 dimer with $K_D$ values ranging from 137 μM to 54.2 nM. As shown in Table 11, at 37° C., all 18 of the tested anti-PD-1 antibodies of the invention bound to MfPD-1 dimer with $K_D$ values ranging from less than 49 μM to 86.3 nM.

Example 4

Blocking of PD-1 Binding to PD-L1 as Determined by ELISA

The ability of anti-PD-1 antibodies to block human PD-1 binding to its ligand, the PD-L1 receptor, was measured using three competition sandwich ELISA formats. Dimeric human PD-L1 proteins, comprised of a portion of the human PD-L1 extracellular domain expressed with either a C-terminal human Fc tag (hPD-L1-hFc; SEQ ID: 325) or a C-terminal mouse Fc tag (hPD-L1-mFc; SEQ ID: 326), or dimeric human PD-L2, comprised of the human PD-L2 extracellular region produced with a C-terminal human Fc tag (hPD-L2-hFc; R&D Systems, #1224-PL) were separately coated at a concentration of 2 μg/mL in PBS on a 96-well microtiter plate overnight at 4° C. Nonspecific binding sites were subsequently blocked using a 0.5% (w/v) solution of BSA in PBS. In a first competition format, a constant concentration of 1.5 nM of a dimeric human PD-1 protein, comprised of the human PD-1 extracellular domain expressed with a C-terminal mouse Fc tag (hPD-1-mFc; SEQ ID: 323) was added to serial dilutions of anti-PD-1 antibodies or isotype control antibodies so that the final concentrations of antibodies ranged from 0 to 200 nM. In a second competition format, a constant concentration of 200 pM of dimeric biotinylated human PD-1 protein, comprised of the human PD-1 extracellular domain that was expressed with a C-terminal human Fc tag (biot-hPD-1-hFc; SEQ ID: 323), was similarly added to serial dilutions of anti-PD-1 antibodies or an isotype control at final antibody concentrations ranging from 0 to 50 nM. In a third competition format, a constant concentration of 100 pM of dimeric hPD-1-mFc protein was similarly added to serial dilutions of anti-PD-1 antibodies or an isotype control at final antibody concentrations ranging from 0 to 100 nM. These antibody-protein complexes were then incubated for 1 hour at room temperature (RT). Antibody-protein complexes with 1.5 nM constant hPD-1-mFc were transferred to microtiter plates coated with hPD-L1-hFc, antibody-protein complexes with 200 pM constant biot-hPD-1-hFc were transferred to hPD-L1-mFc coated plates, and antibody-protein complexes with 100 pM constant hPD-1-mFc were transferred to microtiter plates coated with hPD-L2-hFc. After incubating for 1 hour at RT, the wells were washed, and plate-bound hPD-1-mFc was detected with an anti-mFc polyclonal antibody conjugated with horseradish peroxidase (HRP) (Jackson ImmunoResearch Inc., #115-035-164), and plate-bound biot-hPD-1-hFc was detected with streptavidin conjugated with HRP (Thermo Scientific, #N200). Samples were developed with a TMB solution (BD Biosciences, #51-2606KC and #51-2607KC) to produce a colorimetric reaction and then color development was stabilized by addition of 1M sulfuric acid before measuring absorbance at 450 nm on a Victor X5 plate reader. Data analysis was performed using a sigmoidal dose-response model within Prism™ software (GraphPad). The calculated $IC_{50}$ value, defined as the concentration of antibody required to reduce 50% of human PD-1 binding to human PD-L1 or PD-L2, was used as an indicator of blocking potency. Percent maximum blockade was calculated as a measure of the ability of the antibodies to completely block binding of human PD-1 to human PD-L1 or PD-L2 on the plate as determined from the dose curve. This percent maximum blockade was calculated by subtracting from 100% the ratio of the reduction in signal observed in the presence of the highest tested concentration for each antibody relative to the difference between the signal observed for a sample of human PD-1 containing no anti-PD-1 antibody (0% blocking) and the background signal from HRP-conjugated secondary antibody alone (100% blocking).

Percent maximum blockade and the calculated $IC_{50}$ values for antibodies blocking greater than 35% of the hPD-1 binding signal are shown in Tables 12-14. Antibodies that showed a decrease in the hPD-1 binding signal of 35% or less were defined as non-blockers. Antibodies that showed an increase of 35% or more in the binding signal of human PD-1 were characterized as non-blocker/enhancers. The theoretical assay bottom, defined as the minimum antibody concentration theoretically needed to occupy 50% binding sites of human PD-1 in the assay, is 0.75 nM for the format using 1.5 nM constant hPD-1-mFc, 100 pM for the format using 200 pM constant biot-hPD-1-hFc, and 50 pM for the format using 100 pM constant hPD-1-mFc, indicating that lower calculated $IC_{50}$ values may not represent quantitative protein-antibody site binding. For this reason, antibodies with calculated $IC_{50}$ values less than 0.75 nM in the assay with hPD-1-mFc constant and hPD-L1 coat, less than 100 pM in the assay with biot-hPD-1-hFc constant and hPD-L1 coat, and less than 50 pM in the assay with hPD-1-mFc constant and hPD-L2 coat are reported in Tables 12-14 as <7.5E-10M, <1.0E-10M and <5.0E-11M, respectively.

TABLE 12

ELISA blocking of human PD-1 binding to human PD-L1 by anti-PD-1 antibodies

| Antibody | Blocking 1.5 nM of hPD-1-mFc binding to hPD-L1-hFc, $IC_{50}$ (M) | 200 nM Antibody blocking 1.5 nM hPD-1-mFc binding to hPD-L1-hFc, % blocking |
|---|---|---|
| H4H9019P | 1.3E−09 | 98 |
| H4xH9034P | 5.1E−10* | 98 |
| H4xH9045P | 2.8E−10* | 98 |
| H4xH9048P2 | 3.3E−09 | 67 |
| H4xH9120P2 | 1.0E−09 | 98 |
| H4xH9128P2 | 6.4E−10* | 98 |
| H4xH9035P | 6.2E−10* | 99 |
| H4xH9135P2 | 1.1E−09 | 97 |
| H4xH9145P2 | 9.3E−10 | 90 |
| H4xH9119P2 | 2.0E−10* | 78 |
| H4H9057P2 | 1.9E−10* | 98 |
| H4H9068P2 | NBI/Enchancer | −142 |
| H4xH9037P | 8.9E−10 | 100 |
| H2aM7780N | 6.9E−10* | 94 |
| H2aM7788N | 2.2E−10* | 74 |
| H1M7789N | NBI/Enchancer | −170 |
| H2aM7790N | 1.5E−09 | 74 |
| H2aM7791N | NBI/Enchancer | −154 |
| H2aM7794N | 1.1E−09 | 95 |
| H2aM7795N2 | 8.6E−10 | 93 |
| H2aM7796N | NBI | −20 |
| H2aM7798N | 6.8E−10* | 93 |
| H1M7799N | 2.2E−10* | 82 |
| H1M7800N | 6.0E−10* | 83 |
| H4xH8992P | 1.3E−09 | 93 |
| H4xH8999P | 1.3E−09 | 88 |
| H4xH9008P | 2.4E−09 | 88 |
| Isotype control 1 | NBI | −3 |
| Isotype control 2 | NBI | −34 |
| Isotype control 2 | NBI | −7 |
| Isotype control 2 | NBI | −16 |

Assay theoretical bottom: for blocking ELISA with hPD-1-mFc constant and hPD-L1 coat is 7.5E−10M
*Below theoretical bottom of the assay;
NT - not tested;
NBI - non-blocker;
NBI/Enhancer - non-blocker/enhancer;
IC - inconclusive

TABLE 13

ELISA blocking of biotinylated human PD-1 binding to human PD-L1 by anti-PD-1 antibodies

| Antibody | Blocking 200 pM biot-hPD-1-hFc binding to hPD-L1-mFc, $IC_{50}$ (M) | 50 nM Antibody blocking 200 pM biot-hPD-1-hFc binding to hPD-L1-mFc, % blocking |
|---|---|---|
| H4H9019P | 6.4E−10 | 97 |
| H4xH9034P | 6.6E−11* | 96 |
| H4xH9045P | 1.3E−10 | 95 |
| H4xH9048P2 | IC | 76 |
| H4xH9120P2 | 3.9E−10 | 96 |
| H4xH9128P2 | 1.9E−10 | 97 |
| H4xH9035P | 8.0E−11* | 95 |
| H4xH9135P2 | 1.5E−10 | 96 |
| H4xH9145P2 | 3.5E−10 | 97 |
| H4xH9119P2 | 8.2E−11* | 96 |
| H4H9057P2 | NBI/Enhancer | −57 |
| H4H9068P2 | NBI/Enhancer | −43 |
| H4xH9037P | 7.8E−11* | 95 |
| H2aM7780N | 9.1E−11* | 100 |
| H2aM7788N | 6.5E−11* | 100 |
| H1M7789N | NBI | 9 |
| H2aM7790N | 1.9E−10 | 99 |
| H2aM7791N | NBI/Enhancer | −45 |
| H2aM7794N | 2.3E−10 | 99 |
| H2aM7795N2 | 6.9E−11* | 99 |
| H2aM7796N | 1.3E−09 | 60 |
| H2aM7798N | 7.3E−11* | 100 |
| H1M7799N | 5.9E−11* | 100 |
| H1M7800N | 6.5E−11* | 99 |
| H4xH8992P | 1.6E−10 | 97 |
| H4xH8999P | 1.8E−10 | 92 |
| H4xH9008P | 1.3E−09 | 93 |
| Isotype control 1 | NBI | 19 |
| Isotype control 2 | NBI | 35 |
| Isotype control 2 | NBI | −18 |
| Isotype control 2 | NBI | −11 |

Assay theoretical bottom: for blocking ELISA with biot-hPD-1-mFc constant and hPD-L1 coat is 1.0E−10M
*Below theoretical bottom of the assay;
NT - not tested;
NBI - non-blocker;
NBI/Enhancer - non-blocker/enhancer;
IC - inconclusive

TABLE 14

ELISA blocking of human PD-1 binding to human PD-L2 by anti-PD-1 antibodies

| Antibody | Blocking 100 pM of hPD-1-mFc binding to hPD-L2-hFc, $IC_{50}$ (M) | 100 nM Antibody blocking 100 pM hPD-1-mFc binding to hPD-L2-hFc, % blocking |
|---|---|---|
| H4xH9048P2 | 1.4E−10 | 98 |
| H2aM7795N2 | 2.6E−10 | 100 |
| H2aM7798N | 1.3E−10 | 100 |
| H4xH9008P | 1.3E−09 | 94 |
| Isotype control 2 | NBI | −27 |

Assay theoretical bottom: blocking ELISA with hPD-1-mFc constant and hPD-L2 coat is 5.0E−11M
NBI—non-blocker As indicated in Table 12, in the first assay format, 23 of the 27 anti-PD-1 antibodies blocked 1.5 nM of hPD-1-mFc from binding to hPD-L1-hFc with $IC_{50}$ values ranging from 190 pM to 3.3 nM with the percent maximum blockage ranging from 67% to 100%. One antibody, H2aM7796N, was identified as a non-blocker. Three anti-PD-1 antibodies (H4H9068P2, H1M7789N, and H2aM7791N) were identified as non-blockers/enhancers.

As shown in Table 13, in the second assay format, 23 of the 27 anti-PD-1 antibodies blocked 200 pM of biot-hPD-1-hFc from binding to hPD-L1-mFc with $IC_{50}$ values ranging from 59 pM to 1.3 nM with maximum percent blockade ranging from 60% to 101%. One antibody, H1M7789N, was identified as a non-blocker. Three anti-PD-1 antibodies (H4H9057P2, H4H9068P2, and H2aM7791N) were identified as non-blockers/enhancers.

In the third assay format as shown in Table 14, four anti-PD-1 antibodies of the invention, and an Isotype control were tested. All 4 anti-PD-1 antibodies of the invention blocked 100 pM (fixed concentration) of hPD-1-mFc from binding to plate-coated hPD-L2-hFc with $IC_{50}$ values ranging from 0.13 nM to 1.3 nM and with maximum percent blockade ranging from 94% to 100%.

Example 5

Blocking of PD-1 Binding to PD-L1 as Determined by Biosensor Assay and by Surface Plasmon Resonance Inhibition of human PD-1 from binding to human PD-L1 by different anti-PD-1 monoclonal antibodies was studied either using real time bio-layer interferometry assay on an Octet Red96 biosensor instrument (Fortebio Inc.) or using a real-time surface plasmon resonance biosensor assay on a Biacore 3000 instrument.

Inhibition studies for anti-PD-1 monoclonal antibodies expressed with a mouse Fc were performed on an Octet Red 96 instrument. First, 100 nM of a recombinant human PD-1 expressed with a C-terminal mouse IgG2a Fc tag (hPD-1-mFc; SEQ ID NO: 323) was incubated with 500 nM of each anti-PD-1 monoclonal antibody for at least 1 hour before running the inhibition assay. Around 0.8 nm to 1.2 nm of recombinant human PD-L1 expressed with a C-terminal human IgG1 Fc tag (hPD-L1-hFc; SEQ ID NO: 325) was captured using anti-human IgG Fc capture Octet biosensor. The Octet biosensors coated with hPD-L1-hFc were then dipped into wells containing the mixture of hPD-1-mFc and different anti-PD-1 monoclonal antibodies. The entire experiment was performed at 25° C. in Octet HBST buffer (0.01 M HEPES pH7.4, 0.15M NaCl, 3 mM EDTA, 0.05% v/v Surfactant P20, 0.1 mg/mL BSA) with the plate shaking at a speed of 1000 rpm. The biosensors were washed in Octet HBST buffer in between each step of the experiment. The real-time binding responses were monitored during the entire course of the experiment and the binding response at the end of every step was recorded. Binding of hPD-1-mFc to the captured hPD-L1-hFc was compared in the presence and absence of different anti-PD-1 monoclonal antibodies and was used to determine the blocking behavior of the tested antibodies as shown in Table 15.

TABLE 15

Inhibition of human PD-L1 binding to PD-1 by anti-PD-1 monoclonal antibodies expressed with mouse Fc as measured on an Octet Red 96 instrument

| Anti-PD-1 antibody | Amount of hPD-L1-hFc Captured (nm) | Binding of the mixture of 100 nM hPD-1-mFc and 500 nM anti-PD-1 monoclonal antibody (nm) | % Blocking |
|---|---|---|---|
| No Antibody | 0.77 | 0.07 | 0 |
| H2aM7780N | 1.07 | −0.01 | 114 |
| H2aM7788N | 0.74 | 0.00 | 100 |
| H1M7789N | 0.80 | 0.05 | 29 |
| H2aM7790N | 0.90 | −0.01 | 114 |
| H2aM7791N | 1.17 | 0.23 | −229 |
| H2aM7794N | 0.87 | −0.01 | 114 |

TABLE 15-continued

Inhibition of human PD-L1 binding to PD-1 by anti-PD-1 monoclonal antibodies expressed with mouse Fc as measured on an Octet Red 96 instrument

| Anti-PD-1 antibody | Amount of hPD-L1-hFc Captured (nm) | Binding of the mixture of 100 nM hPD-1-mFc and 500 nM anti-PD-1 monoclonal antibody (nm) | % Blocking |
|---|---|---|---|
| H2aM7795N | 0.28 | −0.01 | 114 |
| H2aM7796N | 0.82 | −0.02 | 129 |
| H2aM7798N | 0.85 | 0.01 | 86 |
| H1M7799N | 0.79 | 0.00 | 100 |
| H1M7800N | 0.96 | 0.00 | 100 |

As shown in Table 15, 9 of the 11 anti-PD-1 antibodies tested on the Octet Red 96 instrument demonstrated strong blocking of hPD-1-mFc from binding to hPD-L1-hFc ranging from 86% to complete blockade of binding. One anti-PD-1 antibody (H1M7789N) tested showed weaker blocking of hPD-1-mFc binding to hPD-L1-hFc with 29% blockade. One antibody (H2aM7791N) tested demonstrated the ability to enhance the binding of hPD-1-mFc to hPD-L1-hFc.

Next, inhibition studies for anti-PD-1 monoclonal antibodies expressed with human Fc were performed on a Biacore 3000 instrument. First, 100 nM of a recombinant human PD-1 expressed with a C-terminal human IgG1 Fc tag (hPD-1-hFc; SEQ ID: 324) was incubated with 500 nM of each anti-PD-1 monoclonal antibody for at least 2 hours before running the inhibition assay. A CM5 Biacore sensor surface was first derivatized with polyclonal rabbit anti-mouse antibody (GE Catalog#BR-1008-38) using standard EDC-NHS chemistry. Around 730 RUs of recombinant human PD-L1 expressed with a C-terminal mouse IgG2a Fc tag (hPD-L1.mFc; SEQ ID: 326) was then captured followed by the injection of 100 nM of hPD-1.hFc in the presence and absence of different anti-PD-1 monoclonal antibodies at a flow rate of 25 μL/min for 3 minutes. The entire experiment was performed at 25° C. in running buffer comprised of 0.01 M HEPES pH7.4, 0.15M NaCl, 3mM EDTA, 0.05% v/v Surfactant Tween-20 (HBS-ET running buffer).The real-time binding responses were monitored during the entire course of the experiment and the binding response at the end of every step was recorded. Binding of hPD-1-hFc to the captured hPD-L1-mFc was compared in the presence and absence of different anti-PD-1 monoclonal antibodies and was used to determine the blocking behavior of the tested antibodies as shown in Table 16.

TABLE 16

Inhibition of human PD-L1 binding to PD-1 by anti-PD-1 monoclonal antibodies expressed with human Fc as measured on a Biacore 3000 instrument

| Anti-PD-1 monoclonal antibody | 500 nM of anti-PD-1 monoclonal antibody (RU) | Binding of the mixture of 100 nM hPD-1.hFc and 500 nM anti-PD-1 monoclonal antibody (RU) | % Blocking |
|---|---|---|---|
| No Antibody | N/A | 100 ± 1.78 | N/A |
| H4H9019P | −2 | −1 | 101 |
| H4xH9034P | −4 | −5 | 105 |
| H4xH9035P | −3 | −4 | 104 |
| H4xH9037P | −4 | −4 | 104 |
| H4xH9045P | −4 | −5 | 105 |
| H4H9048P2 | −7 | 9 | 91 |
| H4H9057P2 | 58 | 57 | 43 |
| H4H9068P2 | −2 | 365 | −265 |
| H4xH9119P2 | −5 | −5 | 105 |
| H4xH9120P2 | 1 | 0 | 100 |
| H4xH9128P2 | −5 | −5 | 105 |
| H4xH9135P2 | −3 | −3 | 102 |
| H4xH9145P2 | −8 | −6 | 106 |
| H4xH8992P | 3 | 2 | 98 |
| H4xH8999P | 1 | 0 | 100 |
| H4xH9008P | 0 | 1 | 99 |
| H4H7795N2 | −5 | −6 | 106 |
| H4H7798N | −6 | −6 | 106 |
| H4H9008P | −7 | −7 | 107 |
| H4H9048P2 | −4 | 6 | 94 |

As shown in Table 16, 18 out of 20 anti-PD-1 antibodies of the invention tested on the Biacore 3000 instrument demonstrated strong blocking of hPD-1-hFc from binding to hPD-L1-mFc with the blockade ranging from 96% to 100%. One antibody demonstrated the ability to enhance the binding of hPD-1-hFc binding to hPD-L1-mFc. In this study, one of the tested antibodies of the invention (H4H9057P2) demonstrated non-specific background binding to the anti-mouse Fc capture surface.

Example 6

Octet Cross-Competition Between Anti-PD-1 Antibodies

Binding competition between anti-PD-1 monoclonal antibodies was determined using a real time, label-free bio-layer interferometry assay on an Octet RED384 biosensor (Pall ForteBio Corp.). The entire experiment was performed at 25° C. in 0.01 M HEPES pH7.4, 0.15M NaCl, 3 mM EDTA, 0.05% v/v Surfactant Tween-20, 0.1 mg/mL BSA (Octet HBS-ET buffer) with the plate shaking at the speed of 1000 rpm. To assess whether 2 antibodies were able to compete with one another for binding to their respective epitopes on a recombinantly expressed human PD-1 with a C-terminal myc-myc-hexahistidine tag (hPD-1-MMH; SEQ ID: 321), around 0.1 nM of hPD-1-MMH was first captured onto anti-Penta-His antibody coated Octet biosensor tips (Pall ForteBio Corp., #18-5079) by submerging the tips for 5 minutes into wells containing a 50 μg/mL solution of hPD-1-MMH. The antigen captured biosensor tips were then saturated with the first anti-PD-1 monoclonal antibody (subsequently referred to as mAb-1) by dipping into wells containing 50 μg/mL solution of mAb-1 for 5 minutes. The biosensor tips were then subsequently dipped into wells containing a 50 μg/mL solution of a second anti-PD-1 monoclonal antibody (subsequently referred to as mAb-2). The biosensor tips were washed in Octet HBS-ET buffer in between every step of the experiment. The real-time binding response was monitored during the course of the experiment and the binding response at the end of every step was recorded. The response of mAb-2 binding to hPD-1-MMH pre-complexed with mAb-1 was compared and competitive/non-competitive behavior of different anti-PD-1 monoclonal antibodies was determined. Results are summarized in Table 17 (*Self-competing mAb2s are not listed).

TABLE 17

Cross-competition between pairs of selected anti-PD-1 antibodies

| First antibody applied ("mAb1") | mAb2 Antibodies shown to compete with mAb1* |
|---|---|
| H4xH8992P | H4xH8999P, H1M7799N, H2aM7780N, H1M7800N, H2aM7788N, H2aM7794N, H2aM7798N, H4xH9145P2, H4H9057P2, H4xH9120P2, H4xH9128P2, H4H9019P, H4xH9119P2, H4xH9135P2, H4xH9034P, H2aM7790N, H4xH9035P, H4xH9037P, H4xH9045P, H2aM7795N |
| H4xH8999P | H4xH8992P, H1M7799N, H2aM7780N, H1M7800N, H2aM7788Nf H2aM7794N, H2aM7798N, H4xH9145P2, H4H9057P2, H4xH9120P2, H4xH9128P2, H4H9019P, H4xH9119P2, H4xH9135P2, H4xH9034P, H2aM7790N, H4xH9035P, H4xH9037P, H4xH9045P, H2aM7795N, H4xH9008P |
| H1M7799N | H4xH8992P, H4xH8999P, H2aM7780N, H1M7800N, H2aM7788N, H2aM7794N, H2aM7798N, H4xH9145P2, H4H9057P2, H4xH9120P2, H4xH9128P2, H4H9019P, H4xH9119P2, H4xH9135P2, H4xH9034P, H2aM7790N, H4xH9035P, H4xH9037P, H4xH9045P, H2aM7795N |
| H2aM7780N | H4xH8992P, H4xH8999P, H1M7799N, H1M7800N, H2aM7788N, H2aM7794N, H2aM7798N, H4xH9145P2, H4H9057P2, H4xH9120P2, H4xH9128P2, H4H9019P, H4xH9119P2, H4xH9135P2, H4xH9034P, H2aM7790N, H4xH9035P, H4xH9037P, H4xH9045P, H2aM7795N, H4xH9008P |
| H1M7800N | H4xH8992P, H4xH8999P, H1M7799N, H2aM7780N, H2aM7788N, H2aM7794N, H2aM7798N, H4xH9145P2, H4H9057P2, H4xH9120P2, H4xH9128P2, H4H9019P, H4xH9119P2, H4xH9135P2, H4xH9034P, H2aM7790N, H4xH9035P, H4xH9037P, H4xH9045P, H2aM7795N, H4xH9008P |
| H2aM7788N | H4xH8992P, H4xH8999P, H1M7799N, H2aM7780N, H1M7800N, H2aM7794N, H2aM7798N, H4xH9145P2, H4H9057P2, H4xH9120P2, H4xH9128P2, H4H9019P, H4xH9119P2, H4xH9135P2, H4xH9034P, H2aM7790N, H4xH9035P, H4xH9037P, H4xH9045P, H2aM7795N, H2aM7791N |
| H2aM7794N | H4xH8992P, H4xH8999P, H1M7799N, H2aM7780N, H1M7800N, H2aM7788N, H2aM7798N, H4xH9145P2, H4H9057P2, H4xH9120P2, H4xH9128P2, H4H9019P, H4xH9119P2, H4xH9135P2, H4xH9034P, H2aM7790N, H4xH9035P, H4xH9037P, H4xH9045P, H2aM7795N, H4xH9008P |
| H2aM7798N | H4xH8992P, H4xH8999P, H1M7799N, H2aM7780N, H1M7800N, H2aM7788N, H2aM7794N, H4xH9145P2, H4H9057P2, H4xH9120P2, H4xH9128P2, H4H9019P, H4xH9119P2, H4xH9135P2, H4xH9034P, H2aM7790N, H4xH9035P, H4xH9037P, H4xH9045P, H2aM7795N, H4xH9008P |
| H4xH9145P2 | H4xH8992P, H4xH8999P, H1M7799N, H2aM7780N, H1M7800N, H2aM7788N, H2aM7794N, H2aM7798N, H4H9057P2, H4xH9120P2, H4xH9128P2, H4H9019P, H4xH9119P2, H4xH9135P2, H4xH9034P, H2aM7790N, H4xH9035P, H4xH9037P, H4xH9045P, H4xH9008P |
| H4H9057P2 | H4xH8992P, H4xH8999P, H1M7799N, H2aM7780N, H1M7800N, H2aM7788N, H2aM7794N, H2aM7798N, H4xH9145P2, H4xH9120P2, H4xH9128P2, H4H9019P, H4xH9119P2, H4xH9135P2, H4xH9034P, H2aM7790N, H4xH9035P, H4xH9037P, H4xH9045P, H2aM7795N, H2aM7791N, H4xH9048P2 |
| H4xH9120P2 | H4xH8992P, H4xH8999P, H1M7799N, H2aM7780N, H1M7800N, H2aM7788N, H2aM7794N, H2aM7798N, H4xH9145P2, H4H9057P2, H4xH9128P2, H4H9019P, H4xH9119P2, H4xH9135P2, H4xH9034P, H2aM7790N, H4xH9035P, H4xH9037P, H4xH9045P, H4xH9048P2 |
| H4xH9128P2 | H4xH8992P, H4xH8999P, H1M7799N, H2aM7780N, H1M7800N, H2aM7788N, H2aM7794N, H2aM7798N, H4xH9145P2, H4H9057P2, H4xH9120P2, H4H9019P, H4xH9119P2, H4xH9135P2, H4xH9034P, H2aM7790N, H4xH9035P, H4xH9037P, H4xH9045P, H4xH9008P, H4H9066P2, H4xH9048P2 |
| H4H9019P | H4xH8992P, H4xH8999P, H1M7799N, H2aM7780N, H1M7800N, H2aM7794N, H2aM7798N, H4xH9145P2, H4H9057P2, H4xH9120P2, H4xH9128P2, H2aM7788N, H4xH9119P2, H4xH9135P2, H4xH9034P, H4xH9035P, H4xH9037P, H4xH9045P, H2aM7795N, H2aM7791N |
| H4xH9119P2 | H4xH8992P, H4xH8999P, H1M7799N, H2aM7780N, H1M7800N, H2aM7794N, H2aM7798N, H4xH9145P2, H4H9057P2, H4xH9120P2, H4xH9128P2, H2aM7788N, H4H9019P, H4xH9135P2, H4xH9034P, H4xH9035P, H4xH9037P, H4xH9045P, H2aM7795N, H2aM7791N |
| H4xH9135P2 | H4xH8992P, H4xH8999P, H1M7799N, H2aM7780N, H1M7800N, H2aM7794N, H2aM7798N, H4xH9145P2, H4H9057P2, H4xH9120P2, H4xH9128P2, H2aM7788N, H4H9019P, H4xH9119P2, H4xH9034P, H4xH9035P, H4xH9037P, H4xH9045P, H2aM7795N, H2aM7791N |

TABLE 17-continued

Cross-competition between pairs of selected anti-PD-1 antibodies

| First antibody applied ("mAb1") | mAb2 Antibodies shown to compete with mAb1* |
|---|---|
| H4xH9034P | H4xH8992P, H4xH8999P, H1M7799N, H2aM7780N, H1M7800N, H2aM7794N, H2aM7798N, H4xH9145P2, H4H9057P2, H4xH9120P2, H4xH9128P2, H4H9019P, H4xH9119P2, H4xH9135P2, H2aM7788N, H2aM7790N, H4xH9035P, H4xH9037P, H4xH9045P, H2aM7795N, H2aM7791N |
| H2aM7790N | H4xH8992P, H1M7799N, H2aM7780N, H1M7800N, H2aM7788N, H2aM7794N, H2aM7798N, H4xH9145P2, H4H9057P2, H4xH9120P2, H4xH9128P2, H4xH9034P, H4xH8999P, H4xH9008P |
| H4xH9035P | H4xH8992P, H4xH8999P, H1M7799N, H2aM7780N, H1M7800N, H2aM7794N, H2aM7798N, H4xH9145P2, H4H9057P2, H4xH9120P2, H4xH9128P2, H2aM7788N, H4H9019P, H4XH9119P2, H4xH9034P, H4xH9135P2, H4xH9037P, H4xH9045P, H2aM7795N, H2aM7791N |
| H4xH9037P | H4xH8992P, H4xH8999P, H1M7799N, H2aM7780N, H1M7800N, H2aM7794N, H2aM7798N, H4xH9145P2, H4H9057P2, H4xH9120P2, H4xH9128P2, H2aM7788N, H4H9019P, H4xH9119P2, H4xH9034P, H4xH9135P2, H4xH9035P, H4xH9045P, H2aM7795N, H2aM7791N |
| H4xH9045P | H4xH8992P, H4xH8999P, H1M7799N, H2aM7780N, H1M7800N, H2aM7794N, H2aM7798N, H4xH9145P2, H4H9057P2, H4xH9120P2, H4xH9128P2, H2aM7788N, H4H9019P, H4xH9119P2, H4xH9034P, H4xH9135P2, H4xH9035P, H4xH9037P, H2aM7795N, H2aM7791N |
| H2aM7795N | H4xH8992P, H4xH8999P, H1M7799N, H2aM7780N, H1M7800N, H2aM7794N, H2aM7798N, H4H9057P2, H2aM7788N, H4H9019P, H4xH9119P2, H4xH9034P, H4xH9135P2, H4xH9035P, H4xH9037P, H4xH9045P, H2aM7791N |
| H4xH9008P | H4xH8999P, H2aM7780N, H2aM7794N, H2aM7798N, H4xH9145P2, H4xH9128P2, H2aM7790N, H4H9068P2, H1M7799N, H4xH9048P2 |
| H2aM7791N | H2aM7788N, H4H9057P2, H4H9019P, H4xH9119P2, H4xH9135P2, H4xH9034P, H4xH9035P, H4xH9037P, H4xH9045P, H2aM7795N |
| H4H9068P2 | H4xH9128P2, H4xH9008P, H1M7789N, H4xH9048P2 |
| H1M7789N | H4xH9008P, H4H9068P2, H4xH9048P2 |
| H4xH9048P2 | H4H9057P2, H4xH9120P2, H4xH9128P2, H4H9019P, H4xH9008P, H4H9068P2, H1M7799N |

Figure 2:
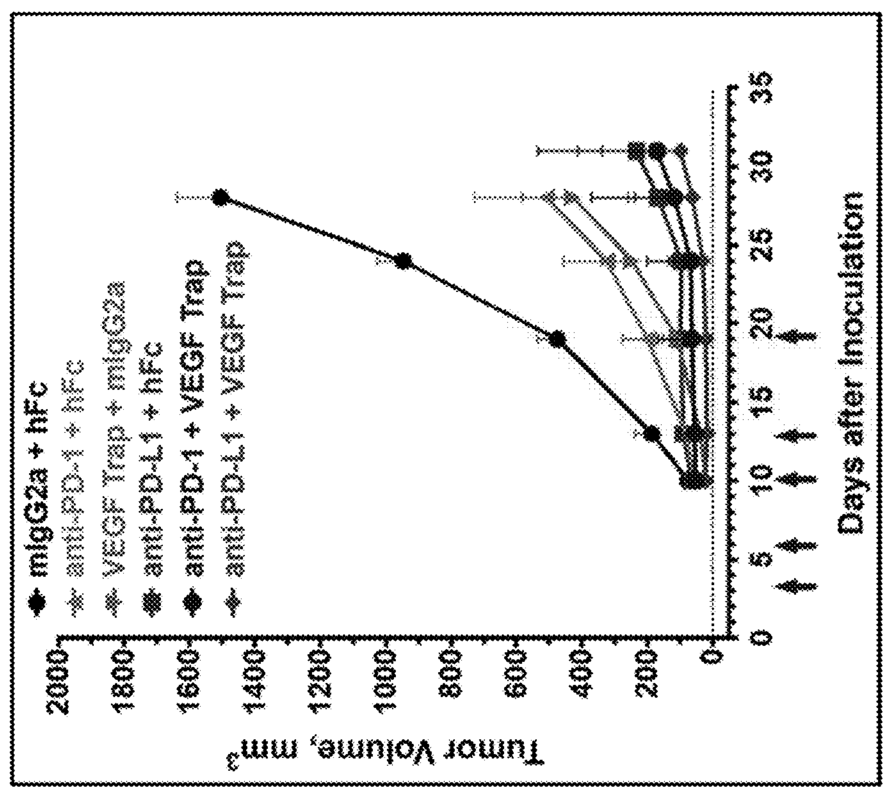
FIG. 2 illustrates tumor growth and survival results for mice implanted with Colon-26 tumor cells at Day 0 and treated with the indicated combinations of molecules by injection at Days 3, 6, 10, 13 and 19 ("early-treatment tumor model"). The graph depicts tumor volume (in $mm^3$) for the different experimental groups at various time points after implantation. Upward arrows along the X-axis indicate the timing of treatment injections. "mIgG2a" is IgG2 isotype control; "Fc" is human Fc control; "VEGF Trap" is aflibercept; "anti-PD-1" is anti-mouse PD-1 clone RPMI-14; "anti-PD-L1" is an anti-PD-L1 monoclonal antibody as described elsewhere herein.

A second binding competition between a panel of selected anti-PD-1 monoclonal antibodies was determined using a real time, label-free bio-layer interferometry assay on an Octet HTX biosensor (Pall ForteBio Corp.). The entire experiment was performed at 25° C. in 0.01 M HEPES pH7.4, 0.15M NaCl, 3 mM EDTA, 0.05% v/v Surfactant Tween-20, 0.1 mg/mL BSA (Octet HBS-ET buffer) with the plate shaking at the speed of 1000 rpm. To assess whether 2 antibodies were able to compete with one another for binding to their respective epitopes on the hPD-1-MMH, around 0.25 nm of hPD-1-MMH was first captured onto anti-Penta-His antibody coated Octet biosensor tips (Fortebio Inc, #18-5079) by submerging the tips for 150 seconds into wells containing a 10 μg/mL solution of hPD-1-MMH. The antigen-captured biosensor tips were then saturated with a first anti-PD-1 monoclonal antibody (subsequently referred to as mAb-1) by dipping into wells containing 100 μg/mL solution of mAb-1 for 5 minutes. The biosensor tips were then subsequently dipped into wells containing a 100 μg/mL solution of second anti-PD-1 monoclonal antibody (subsequently referred to as mAb-2) for 4 minutes. All the biosensors were washed in Octet HBS-ET buffer in between every step of the experiment. The real-time binding response was monitored during the course of the experiment and the binding response at the end of every step was recorded as shown in FIG. 2. The response of mAb-2 binding to hPD-1-MMH pre-complexed with mAb-1 was compared and competitive/non-competitive behavior of different anti-PD-1 monoclonal antibodies was determined. Results are summarized in Table 18 (*Self-competing mAb2s are not listed).

TABLE 18

Cross-competition between pairs of selected anti-PD-1 antibodies

| First Antibody applied ("mAb1") | mAb2 Antibodies Shown to Compete with mAb1* |
|---|---|
| H4H7795N2 | H4H7798N |
| H4H7798N | H4H7795N2; H4H9008P |
| H4H9008P | H4H7798N; H4H9068P2 |
| H4H9068P2 | H4H9008P; H4H9048P2 |
| H4H9048P2 | H4H9068P2 |

Under the experimental conditions disclosed in this Example, H4H7795N2 cross-competed with H4H7798N; H4H7798N cross-competed with H4H7795N2 and H4H9008P; H4H9008P cross-competed with H4H7798N and H4H9068P2; H4H9068P2 cross-competed with H4H9008P and H4H9048P2.

Example 7

Antibody Binding to Cells Overexpressing PD-1

The binding of anti-PD-1 antibodies to a human embryonic kidney cell line (HEK293; ATCC, #CRL-1573) stably transfected with full length human PD-1 (amino acids 1 to 289 of accession number NP_005009.2) (HEK293/hPD-1) was determined by FACS.

For the assay, adherent cells were detached using trypsin or enzyme-free dissociation buffer and blocked with complete medium. Cells were centrifuged and resuspended at a concentration of 2.5-6×10^6 cells/mL in cold PBS containing 2% FBS. HEK293 parental and HEK293/hPD-1 cells were then incubated for 15-30min on ice with 100 nM of each anti-PD-1 antibody. Unbound antibodies were removed by washing with D-PBS containing 2% FBS, and cells were subsequently incubated with an allophycocyanin-conjugated secondary F(ab')2 recognizing either human Fc (Jackson ImmunoResearch, #109-136-170) or mouse Fc (Jackson ImmunoResearch, #115-136-146) for 15-30 minutes on ice. Cells were washed with D-PBS containing 2% FBS to remove unbound secondary F(ab')2 and fluorescence measurements were acquired using either a HyperCyte (IntelliCyt, Inc.) flow cytometer or an Accuri flow cytometer (BD Biosciences). Data was analyzed using FlowJo software (Tree Star).

TABLE 19

FACS binding of anti-PD-1 antibodies to HEK293/hPD-1 cells and parental HEK293 cells

| Antibody | FACS on HEK293 parental cells [MFI] | FACS on HEK293/hPD-1 cells [MFI] | Ratio of HEK293/hPD-1 to HEK293 parental cells |
|---|---|---|---|
| H1M7789N | 262 | 24166 | 92.3 |
| H1M7799N | 255 | 6855 | 26.9 |
| H1M7800N | 275 | 6812 | 24.7 |
| H2aM7780N | 320 | 23656 | 73.8 |
| H2aM7788N | 305 | 23112 | 75.7 |
| H2aM7790N | 270 | 47310 | 175.5 |
| H2aM7791N | 274 | 4948 | 18.0 |
| H2aM7794N | 270 | 19127 | 71.0 |
| H2aM7795N | 288 | 817 | 2.8 |
| H2aM7796N | 297 | 49755 | 167.8 |
| H2aM7798N | 300 | 23443 | 78.1 |
| H4H9019P | 111 | 8610 | 77.2 |
| H4H9057P2 | 141 | 6501 | 46.1 |
| H4H9068P2 | 285 | 1940 | 6.8 |
| H4xH8992P | 358 | 17502 | 48.9 |
| H4xH8999P | 809 | 28875 | 35.7 |
| H4xH9008P | 509 | 26233 | 51.5 |
| H4xH9034P | 147 | 10115 | 69.0 |
| H4xH9035P | 108 | 9915 | 91.7 |
| H4xH9037P | 108 | 8787 | 81.4 |
| H4xH9045P | 95 | 8884 | 93.7 |
| H4xH9048P2 | 102 | 7196 | 70.8 |
| H4xH9119P2 | 109 | 9142 | 84.0 |
| H4xH9120P2 | 109 | 9975 | 91.9 |
| H4xH9128P2 | 135 | 9081 | 67.5 |
| H4xH9135P2 | 114 | 9380 | 82.2 |
| H4xH9145P2 | 226 | 11552 | 51.2 |

As shown in Table 19, 25 of the 27 anti-PD-1 antibodies of the invention showed strong binding to the HEK293/hPD-1 cells compared to binding on the parental HEK293 line. Two antibodies of the invention (H2aM7795N and H4H9068P2) bound weaker to human PD-1 expressing cells compared to the other antibodies tested.

To further characterize anti-PD1 antibodies of the invention, dose-dependent binding to a human embryonic kidney cell line (HEK293; ATCC, #CRL-1573) stably transfected with full length human PD-1 (amino acids 1 to 289 of accession number NP_005009.2) (HEK293/hPD-1) was determined by FACS.

For the assay, adherent cells were detached using trypsin and blocked with complete medium. Cells were centrifuged and resuspended at a concentration of 6×10^6 cells/mL in staining buffer (1% FBS in PBS). To determine the $EC_{50}$ and $E_{max}$ of the anti-PD1 antibodies, 90 uL of cell suspension was incubated for 30 minutes on ice with a serial dilution of anti-PD-1 antibodies and controls diluted to a final concentration ranging from 5 pM to 100 nM (no mAb sample was included as negative control) in staining buffer. Cells were then centrifuged and pellets were washed once with staining buffer to remove unbound antibodies. Cells were subsequently incubated for 30 minutes on ice either with an allophycocyanin-conjugated secondary F(ab')2 recognizing human Fc (Jackson ImmunoResearch, #109-136-170) or mouse Fc (Jackson ImmunoResearch, #115-136-071). Cells were centrifuged and pellets were washed once with staining buffer to remove unbound secondary F(ab')2 and then fixed overnight with a 1:1 dilution of Cytofix (BD Biosciences, #554655) and staining buffer. The following day, cells were centrifuged and pellets were washed once with staining buffer, resuspended and filtered. Fluorescence measurements were acquired on Hypercyt® cytometer and analyzed in ForeCyt™ (IntelliCyt; Albuquerque, N. Mex.) to determine the mean fluorescence intensities (MFI). The $EC_{50}$ values were calculated from a four-parameter logistic equation over an 11-point response curve using GraphPad Prism. $E_{max}$ for each antibody was defined as the binding at the highest antibody dose (100 nM) tested.

TABLE 20

Dose dependent FACS binding of anti-PD-1 antibodies to HEK293/hPD-1 cells

| Antibody | $EC_{50}$ [M] | Max Geom. Mean [MFI] @ 100 nM |
|---|---|---|
| H2aM7779N | 2.59E−09 | 16832 |
| H2aM7780N | 1.69E−09 | 18415 |
| H2aM7781N | 5.67E−10 | 13740 |
| H2aM7782N | 1.26E−09 | 17302 |
| H2aM7787N | 2.40E−09 | 15744 |
| H2aM7788N | 3.21E−10 | 14827 |
| H2aM7790N | 1.71E−10 | 19196 |
| H2aM7791N | No $EC_{50}$ determined | 1397 |
| H2aM7794N | 1.37E−09 | 16406 |
| H2aM7795N | No $EC_{50}$ determined | 624 |
| H2aM7798N | 6.985E−11 | 20900 |
| H1M7799N | 3.318E−11 | 24405 |
| H1M7800N | 4.80E−11 | 20763 |
| H4xH8992P | 5.45E−11 | 11368 |
| H4xH8999P | 5.27E−11 | 28341 |
| H4H9019P | 1.40E−09 | 29201 |
| H4xH9034P | 2.09E−10 | 32388 |
| H4xH9035P | 1.15E−10 | 28708 |
| H4xH9037P | 6.74E−10 | 36441 |
| H4xH9045P | 9.17E−11 | 24662 |
| H4xH9048P2 | 6.68E−10 | 33687 |
| H4H9057P2 | 2.363E−10 | 19953 |
| H4H9068P2 | No $EC_{50}$ determined | 639 |
| H4xH9119P2 | 3.476E−10 | 37789 |
| H4xH9120P2 | 4.797E−10 | 34057 |
| H4xH9128P2 | 1.551E−09 | 37167 |
| H4xH9135P2 | 1.048E−10 | 32793 |
| H4xH9145P2 | 2.321E−10 | 30613 |
| mlgG1 isotype | N/A | 200 |
| mlgG2a isotype | N/A | 239 |
| hlgG4 isotype | N/A | 459 |

TABLE 21

Dose dependent FACS binding of anti-PD-1 antibodies to HEK293/hPD-1 cells

| Antibody | $EC_{50}$ [M] | Max Geom. Mean [MFI] @ 100 nM |
|---|---|---|
| H4H7795N2 | Inconclusive | 15188 |
| H4H7798N | 5.09E−10 | 20305 |
| H4H9008P | Inconclusive | 32230 |
| H4H9048P2 | 1.60E−09 | 39774 |

TABLE 21-continued

| Dose dependent FACS binding of anti-PD-1 antibodies to HEK293/hPD-1 cells | | |
|---|---|---|
| Antibody | $EC_{50}$ [M] | Max Geom. Mean [MFI] @ 100 nM |
| H1M7789N | Inconclusive | 35574 |
| H2aM7796N | 4.81E−09 | 14111 |
| mlgG1 isotype | N/A | 858 |
| mlgG2a isotype | N/A | 352 |
| hlgG4 isotype | N/A | 809 |

As shown in Table 20, 25 of 28 anti-PD1 antibodies of the invention showed dose dependent binding to HEK293/hPD-1 cells with $EC_{50}$ values ranging from 33.18 pM to 2.59 nM and $E_{max}$ values ranging from 37,789 to 11,368 MFI. Three anti-PD1 antibodies of the invention did not demonstrate strong binding to HEK293/hPD-1 cells and therefore an $EC_{50}$ value could not be determined. None of the isotype controls demonstrated any measurable binding in this assay.

As shown in Table 21, 3 of 6 anti-PD1 antibodies of the invention showed dose dependent binding to HEK293/hPD-1 cells with $EC_{50}$ values ranging from 509 pM to 4.81 nM and $E_{max}$ values ranging from 39,774 to 14,111 MFI. Three antibodies of the invention tested bound to HEK293/hPD-1 cells, but did not reach a plateau. Therefore their precise $EC_{50}$ values could not be determined and their $EC_{50}$ values are referred to as inconclusive. None of the isotype controls demonstrated any measurable binding in this assay.

Example 8

Blocking of PD-1-Induced T-Cell Down-Regulation in a T-Cell/APC Luciferase Reporter Assay T-cell activation is achieved by stimulating T-cell receptors (TcR) that recognize specific peptides presented by major histocompatibility complex class I or II proteins on antigen-presenting cells (APC). Activated TcRs in turn initiate a cascade of signaling events that can be monitored by reporter genes driven by transcription factors such as activator-protein 1 (AP-1), Nuclear Factor of Activated T-cells (NFAT) or Nuclear factor kappa-light-chain-enhancer of activated B cells (NFKb). T-cell response is modulated via engagement of co-receptors expressed either constitutively or inducibly on T-cells. One such receptor is PD-1, a negative regulator of T-cell activity. PD-1 interacts with its ligand, PD-L1, which is expressed on target cells including APCs or cancer cells, and acts to deliver inhibitory signals by recruiting phosphatases to the TcR signalosome, resulting in the suppression of positive signaling.

The ability of anti-PD-1 antibodies to antagonize PD-1/PD-L1-mediated signaling through the PD-1 receptor in human T cell lines was assessed using an in vitro cell based assay shown in FIG. 1. The bioassay was developed to measure T cell signaling induced by interaction between APC and T cells by utilizing a mixed culture derived from two mammalian cell lines: Jurkat cells (an immortalized T cell line) and Raji cells (a B cell line). For the first component of the bioassay, Jurkat Clone E6-1 cells (ATCC, #TIB-152) were transduced with the Cignal Lenti AP-1 Luc Reporter (Qiagen—Sabiosciences, #CLS-011L) as per the manufacturer's instructions. The lentivirus encodes the firefly luciferase gene under the control of a minimal CMV promoter, tandem repeats of the TPA-inducible transcriptional response element (TRE) and a puromycin resistance gene. The engineered Jurkat cell line was subsequently transduced with a PD-1 chimera comprising the extracellular domain of human PD-1 (amino acids from 1 to 170 of human PD1; accession number NP_005009.2) and the transmembrane and cytoplasmic domains of human CD300a (amino acids from 181 to 299 of human CD300a; accession number NP_009192.2). The resulting stable cell line (Jurkat/AP1-Luc/hPD1-hCD300a) was selected and maintained in RPMI/10% FBS/penicillin/streptomycin/glutamine supplemented with 500 ug/mL G418+1 ug/mL puromycin.

For the second component of the bioassay, Raji cells (ATCC, #CCL-86) were transduced with human PD-L1 gene (amino acids 1-290 of accession number NP_054862.1) that had been cloned into a lentiviral (pLEX) vector system (Thermo Scientific Biosystems, #OHS4735). Raji cells, positive for PD-L1 (Raji/hPD-L1) were isolated by FACS using a PD-L1 antibody and maintained in Iscove/10% FBS/penicillin/streptomycin/glutamine supplemented with 1 ug/mL puromycin.

To simulate the APC/T cell interaction, a bispecific antibody composed of one Fab arm that binds to CD3 on T cells and the other one Fab arm binding that binds to CD20 on Raji cells (CD3xCD20 bispecific antibody; e.g., as disclosed in US20140088295) was utilized. The presence of the bispecific molecule in the assay results in the activation of the T cell and APC by bridging the CD3 subunits on T-cells to CD20 endogenously expressed on Raji cells. Ligation of CD3 with anti-CD3 antibodies has been demonstrated to lead to activation of T cells. In this bioassay, antibodies blocking the PD1/PD-L1 interaction rescue T-cell activity by disabling the inhibitory signaling and subsequently leading to increased AP1-Luc activation.

In the luciferase-based bioassay, RPMI1640 supplemented with 10% FBS and penicillin/streptomycin/glutamine was used as assay medium to prepare cell suspensions and antibody dilutions to carry out the screening of anti-PD1 monoclonal antibodies (mAbs). On the day of the screening, EC50 values of anti-PD1 mAbs, in the presence of a fixed concentration of CD3xCD20 bispecific antibody (30 pM), as well as the EC50 of the bispecific antibody alone, were determined. In the following order, cells and reagents were added to 96 well white, flat-bottom plates. For the anti-PD1 mAb EC50 determinations, first a fixed concentration of CD3xCD20 bispecific antibody (final 30 pM) was prepared and added to the microtiter plate wells. Then 12-point serial dilutions of anti-PD1 mAbs and controls were added (final concentrations ranging from 1.7 pM to 100 nM; plus wells with assay medium alone). For the bispecific antibody (alone) $EC_{50}$ determination, the bispecific antibody, at final concentrations ranging from 0.17 pM to 10 nM (plus wells with assay medium alone), was added to the microtiter plate wells. Subsequently, a 2.5×10^6/mL Raji/hPD-L1 cell suspension was prepared and 20 uL per well was added (final cell number/well 5×10^4 cells). Plates were left at room temperature (15-20 minutes), while a suspension of 2.5×10^6/mL of Jurkat/AP1-Luc/hPD1(ecto)-hCD300a(TM-Cyto) was prepared. 20 uL of the Jurkat suspension (final cell number/well 5×10^4 cells) was added per well. Plates containing the co-culture were incubated for 5 to 6 hours at 37° C./5% $CO_2$. Samples were tested in duplicates and luciferase activity was then detected after the addition of ONE-Glo™ (Promega, #E6051) reagent and relative light units (RLUs) were measured on a Victor luminometer.

RLU values for each screened antibody were normalized by setting the assay condition with fixed (30 pM) concentration of the CD3/CD20 bispecific antibody, but without anti-PD-1 antibody to 100%. This condition corresponds to the maximal AP1-Luc response elicited by the bispecific molecule in the presence of the PD-1/PD-L1 inhibitory signal. Upon addition of the anti-PD-1 antibody, the inhibitory signal is suppressed, and the increased stimulation is shown here as $E_{max}$, the percentage increase in the signal in the presence of the highest antibody dose tested (100 nM). To compare potency of the anti-PD1 antibodies tested, the concentration of antibody at which the normalized RLU value reached 150% activation was determined from a four-parameter logistic equation over a 12-point response curve using GraphPad Prism. The results are summarized in Table 22 and Table 23, respectively.

TABLE 22

Anti-PD1 antibody blocking PD-1/PD-L1 dependent inhibition of AP1-Luc signaling in Experiment 1

| Antibody | Antagonistic assay Concentration (M) of Antibody at 150% activation Experiment 1 | Antagonistic assay $E_{max}$ mean [%] @ 100 nM Experiment 1 |
|---|---|---|
| H1M7789N | N/A | 135 |
| H1M7799N | 2.97E−08 | 183 |
| H1M7800N | 1.65E−08 | 182 |
| H2aM7779N | 8.92E−09 | 214 |
| H2aM7780N | 6.52E−09 | 228 |
| H2aM7781N | 6.70E−09 | 230 |
| H2aM7782N | 9.96E−09 | 215 |
| H2aM7787N | 1.38E−08 | 215 |
| H2aM7788N | 4.72E−09 | 189 |
| H2aM7790N | 5.24E−09 | 234 |
| H2aM7791N | N/A | 103 |
| H2aM7794N | 4.09E−08 | 170 |
| H2aM7795N | N/A | 109 |
| H2aM7796N | N/A | 121 |
| H2aM7798N | 7.99E−10 | 239 |
| H4H9019P | 1.79E−08 | 180 |
| H4xH9034P | 2.62E−09 | 202 |
| H4xH9035P | 1.20E−09 | 227 |
| H4xH9037P | 2.82E−09 | 195 |
| H4xH9045P | 2.23E−08 | 176 |
| H4xH9048P2 | N/A | 138 |
| H4H9057P2 | 2.68E−08 | 212 |
| H4H9068P2 | N/A | 102 |
| H4xH9119P2 | 1.11E−08 | 163 |
| H4xH9120P2 | 1.10E−08 | 166 |
| H4xH9128P2 | 3.99E−09 | 187 |
| H4xH9135P2 | 1.55E−09 | 193 |
| H4xH9145P2 | 2.40E−09 | 185 |
| H4xH8992P | 5.32E−09 | 178 |
| H4xH8999P | 8.63E−10 | 217 |
| H4H7798N | 1.54E−09 | 202 |
| mlgG1 isotype control | N/A | 92 |
| mlgG2a isotype control | N/A | 91 |
| hlgG4 isotype control | N/A | 94 |

N/A = not applicable because at the concentrations tested these antibodies did not activate 150%

TABLE 23

Anti-PD1 antibody blocking PD-1/PD-L1 dependent inhibition of AP1-Luc signaling in Experiment 2

| Antibody | Antagonistic assay Concentration (M) of Antibody at 150% activation Experiment 2 | Antagonistic assay $E_{max}$ mean [%] @ 100 nM Experiment 2 |
|---|---|---|
| H4H7795N2 | N/A | 110 |
| H4H7798N | 1.59E−10 | 343 |
| H4H9008P | 9.84E−08 | 150 |
| H4H9048P | N/A | 134 |
| hlgG4 isotype control | N/A | 98 |

TABLE 23-continued

Anti-PD1 antibody blocking PD-1/PD-L1 dependent inhibition of AP1-Luc signaling in Experiment 2

| Antibody | Antagonistic assay Concentration (M) of Antibody at 150% activation Experiment 2 | Antagonistic assay $E_{max}$ mean [%] @ 100 nM Experiment 2 |
|---|---|---|

N/A= not applicable because at the concentrations tested these antibodies did not activate 150%

As shown in Table 22, 25 out of the 31 anti-PD-1 antibodies of the invention tested blocked PD-1/PD-L1 inhibition with $E_{max}$ values ranging from 239 to 163. Six out of the 31 anti-PD-1 antibodies of the invention did not demonstrate substantial blockade of PD1/PD-L1 interaction when tested in this assay.

As shown in Table 23, 2 out of the 4 anti-PD-1 antibodies of the invention tested blocked PD-1/PD-L1 inhibition with $E_{max}$ values of 150 and 343%, respectively. 2 out of the 4 anti-PD-1 antibodies of the invention did not demonstrate substantial blockade of PD1/PD-L1 interaction when tested in this assay.

Example 9

In Vivo Efficacy of Anti-PD-1 Antibodies

To determine the effect of a select number of anti-PD-1 antibodies of the invention in a relevant in vivo model, three MC38.ova tumor growth studies, involving subcutaneous injection of tumor cells and started on different days, were conducted in mice that were homozygous for the expression of the extracellular domain of human PD-1 in place of extracellular domain of mouse PD-1 (PD-1 Humin mice) on a 75% C57/BI6/25% 129 strain background.

For the studies, mice were divided evenly according to body weight into 5 treatment or control groups for Study 1 (5 mice per group), 8 treatment or control groups for Study 2 (5 mice per group), and 5 treatment or control groups for Study 3 (7 mice per group). At day 0, mice were anesthetized by isoflurane inhalation and then injected subcutaneously into the right flank with $5\times10^5$ MC38.ova cells in suspension of 100 uL of DMEM for Study 1 or $1\times10^6$ MC38.ova cells in suspension of 100 uL of DMEM for Study 2 and Study 3. For Study 1, treatment groups were intraperitoneally injected with 200 ug of either one of three anti-PD-1 antibodies of the invention, or an isotype control antibody with irrelevant specificity on days 3, 7, 10, 14, and 17 of the experiment, while one group of mice was left untreated. For Study 2, treatment groups were intraperitoneally injected with either one of three anti-PD-1 antibodies of the invention at 10 mg/kg or 5 mg/kg per/dose, one antibody of the invention (H4H7795N2) at 10 mg/kg per dose, or an isotype control antibody with irrelevant specificity at 10 mg/kg on days 3, 7, 10, 14, and 17 of the experiment. For Study 3, treatment groups were intraperitoneally injected with either one of two anti-PD-1 antibodies of the invention at 5 mg/kg or 2.5 mg/kg per/dose, or an isotype control antibody with irrelevant specificity at 5 mg/kg on days 3, 7, 10, 14, and 17 of the experiment. Experimental dosing and treatment protocol for groups of mice are shown in Table 24.

TABLE 24

| Experimental dosing and treatment protocol for groups of mice | | | |
|---|---|---|---|
| Study # | Samples Tested | Dosage amount at each dosage time point | Dosing interval |
| 1 | Isotype Control | 200 ug | Days 3, 7, 10, 14, 17 |
| | No treatment | N/A | N/A |
| | H4H7798N | 200 ug | Days 3, 7, 10, 14, 17 |
| | H4H7795N2 | 200 ug | Days 3, 7, 10, 14, 17 |
| | H4H9008P | 200 ug | Days 3, 7, 10, 14, 17 |
| 2 | Isotype Control | 10 mg/kg | Days 3, 7, 10, 14, 17 |
| | H4H7795N2 | 10 mg/kg | Days 3, 7, 10, 14, 17 |
| | H4H7798N | 10 mg/kg | Days 3, 7, 10, 14, 17 |
| | H4H7798N | 5 mg/kg | Days 3, 7, 10, 14, 17 |
| | H4H9048P2 | 10 mg/kg | Days 3, 7, 10, 14, 17 |
| | H4H9048P2 | 5 mg/kg | Days 3, 7, 10, 14, 17 |
| | H4H9008P | 10 mg/kg | Days 3, 7, 10, 14, 17 |
| | H4H9008P | 5 mg/kg | Days 3, 7, 10, 14, 17 |
| 3 | Isotype Control | 5 mg/kg | Days 3, 7, 10, 14, 17 |
| | H4H7798N | 5 mg/kg | Days 3, 7, 10, 14, 17 |
| | H4H7798N | 2.5 mg/kg | Days 3, 7, 10, 14, 17 |
| | H4H9008P | 5 mg/kg | Days 3, 7, 10, 14, 17 |
| | H4H9008P | 2.5 mg/kg | Days 3, 7, 10, 14, 17 |

For the studies, average tumor volumes determined by caliper measurements and percent survival at Day 14 or 17 and Day 23 or 24 of each experiment for each treatment group were recorded. In addition, the number of tumor-free mice were also assessed at the end of the study (Day 42 for Study 1 and Day 31 for Study 2 and Study 3). Results, expressed as mean tumor volume (mm$^3$)(±SD), percent survival, and number of tumor-free mice are shown in Table 23 for Study 1, Table 3 for Study 2, and Table 4 for Study 3.

TABLE 25

| Mean tumor volume, percent survival and numbers of tumor free mice in each treatment group from in vivo tumor Study 1 | | | | | |
|---|---|---|---|---|---|
| | Tumor Volume, mm$^3$ mean (±SD) | | Survival, % | | Tumor-Free Mice |
| Treatment group (n = 5) | Day 17 200 ug/mouse | Day 23 200 ug/mouse | Day 17 200 ug/mouse | Day 23 200 ug/mouse | Day 42 200 ug/mouse |
| No treatment | 189 (±110) | 554 (±317) | 100% | 100% | 1/5 (20%) |
| Isotype control | 86 (±114) | 515 (±859) | 100% | 60% | 2/5 (40%) |
| H4H7798N | 0 (0) | 0 (0) | 100% | 100% | 5/5 (100%) |
| H4H9008P | 14 (±19) | 205 (±312) | 100% | 100% | 3/5 (60%) |
| H4H7795N2 | 89 (±176) | 445 (±889) | 100% | 80% | 3/5 (60%) |

As shown in Table 25 for Study 1, mice treated with one antibody of the invention, H4H7798N did not develop any detectable tumors during the course of the study. Mice treated with H4H9008P exhibited a sustained reduced tumor volume as compared to controls at days 17 and 24 of the study with 3 out of 5 mice or 4 out of 5 mice being tumor free by the end of the experiment, respectively. In contrast, treatment with one of the anti-PD1 antibodies, H4H7795N2, did not demonstrate significant efficacy in reducing tumor volume in this study as compared to controls. By day 23 of the study, 1 out of 5 mice died in the H4H7795N2 group, and 2 out of 5 mice died in the isotype control treatment group. In non-treatment group and isotype control group some mice exhibited spontaneous regression of tumors (1 out of 5 mice and 2 out of 5 mice, respectively).

TABLE 26

| Mean tumor volume, percent survival and numbers of tumor free mice in each treatment group from in vivo tumor Study 2 | | | | | | | | | | |
|---|---|---|---|---|---|---|---|---|---|---|
| Treatment | Tumor Volume, mm$^3$ mean (±SD) | | | | Survival, % | | | | Tumor-Free Mice | |
| group | Days 17 | | Day 24 | | Day 17 | | Day 24 | | Day 31 | |
| (n = 5) | 5 mg/kg | 10 mg/kg | 5 mg/kg | 10 mg/kg | 5 mg/kg | 10 mg/kg | 5 mg/kg | 10 mg/kg | 5 mg/kg | 10 mg/kg |
| Isotype control | N/A | 449 (±434) | N/A | 824 (±858) | N/A | 100% | N/A | 60% | N/A | 1/5 (20%) |
| H4H7798N | 17 (±38) | 0 (0) | 104 (±233) | 0 (0) | 100% | 100% | 100% | 100% | 4/5 (80%) | 5/5/ (100%) |

TABLE 26-continued

Mean tumor volume, percent survival and numbers of tumor free mice in each treatment group from in vivo tumor Study 2

| Treatment | Tumor Volume, mm$^3$ mean (±SD) | | | | Survival, % | | | | Tumor-Free Mice | |
|---|---|---|---|---|---|---|---|---|---|---|
| group | Days 17 | | Day 24 | | Day 17 | | Day 24 | | Day 31 | |
| (n = 5) | 5 mg/kg | 10 mg/kg | 5 mg/kg | 10 mg/kg | 5 mg/kg | 10 mg/kg | 5 mg/kg | 10 mg/kg | 5 mg/kg | 10 mg/kg |
| H4H9008P | 91 (±204) | 12 (±28) | 228 (±509) | 96 (±215) | 100% | 100% | 80% | 100% | 4/5 (80%) | 4/5 (80%) |
| H4H9048P2 | 94 (±160) | 10 (±21) | 328 (±559) | 67 (±150) | 100% | 100% | 80% | 100% | 3/5 (60%) | 4/5 (80%) |
| H4H7795N2 | N/A | 124 (±209) | N/A | 359 (±657) | N/A | 100% | N/A | 80% | N/A | 2/5 (40%) |

As shown in Table 26 for Study 2, mice treated with one antibody of the invention, H4H7798N at 10 mg/kg did not develop detectable tumors during the course of the study. Groups of mice treated with 10 mg/kg of either H4H9008P or H4H9048P2 exhibited substantially reduced tumor volume as compared to controls at days 17 and 24 of the study. Four out of 5 mice in each group treated with 10 mg/kg of either H4H9008P or H4H9048P2 were tumor free at Day 31, whereas in the isotype control treatment group only 1 out of 5 animals was tumor free as a result of spontaneous tumor regression. One antibody tested at 10 mg/kg, H4H7795N2, demonstrated substantially reduced tumor volume as compared to controls at days 17 and 24 of the study, but this antibody was the least efficacious anti-PD1 antibody with only 2 out of 5 mice surviving at the end of the experiment.

A dose-dependent response in tumor suppression at the tested doses (5 mg/kg and 10 mg/kg) was observed in groups treated with H4H7798N, H4H9008P, and H4H9048P2. H4H7798N or H4H9008P therapy at 5 mg/kg was less efficacious, with 4 out of 5 tumor-free mice at the end of experiment on day 21, whereas 5 out of 5 mice remained tumor-free in both 10 mg/kg dose groups of H4H7798N, and H4H9008P.

Dunett's test in 2 way ANOVA multiple comparisons revealed that the differences in tumor growth between the group treated with isotype control antibody at 10 mg/kg as reference and the groups treated at 10 mg/kg with either H4H7798N, H4H9008P, or H4H9048P2 were statistically significant with p value<0.005. The differences in tumor growth between the group treated with isotype control antibody at 10 mg/kg as reference and the groups treated at 5 mg/kg with either H4H7798N, H4H9008P, or H4H9048P2 were also statistically significant with a p value<0.05.

As shown in Table 27 for Study 3, 6 out or 7 mice treated with one antibody of the invention, H4H7798N, or another antibody of the invention, H4H9008P, at 5 mg/kg were tumor free at the end of the experiment, whereas there were no tumor free animals in the isotype control group. One tumor-bearing mouse in the IgG4 control group died on post-implantation day 17. Only 4 out of 7 mice treated with H4H9008P at 2.5 mg/kg dose remained tumor free at the end of the experiment. The difference in tumor volumes at day 21 between anti-PD-1 antibodies tested and an isotype control group was statistically significant as determined by one-way ANOVA with Dunnett's multiple comparison post-test with p<0.01. All four anti-PD-1 antibodies were equally more efficacious at the 5 mg/kg dose than at the 2.5 mg/kg dose.

Example 10

Anti-Tumor Effects of a Combination of an Anti-PD-1 Antibody and a VEGF Antagonist in a Mouse Early-Treatment Tumor Model An early-treatment tumor model was developed to test the efficacy of a combination of an anti-PD-1 antibody and a VEGF antagonist. In this model, the combination therapy is administered shortly after tumor implantation. The experiment also used an anti-PD-L1 antibody alone and in combination with the VEGF antagonist. The anti-PD-1 antibody used in this experiment was anti-mouse PD-1 clone "RPMI-14" with rat IgG2b (Bio X Cell, West Lebanon, N.H.). The VEGF antagonist used in this experiment was aflibercept (a VEGF receptor-based chimeric molecule, also known as "VEGF-trap" or "VEGFR1R2-FcΔC1(a)," a full description

TABLE 27

Mean tumor volume, percent survival and numbers of tumor free mice in each treatment group from in vivo tumor Study 3

| Treatment | Tumor Volume, mm$^3$ mean (±SD) | | | | Survival, % | | | | Tumor-Free Mice | |
|---|---|---|---|---|---|---|---|---|---|---|
| | Days 14 | | Day 21 | | Day 14 | | Day 21 | | Day 31 | |
| group (n = 7) | 2.5 mg/kg | 5 mg/kg | 2.5 mg/kg | 5 mg/kg | 2.5 mg/kg | 5 mg/kg | 2.5 mg/kg | 5 mg/kg | 2.5 mg/kg | 5 mg/kg |
| Isotype control | N/A | 94 (±44) | N/A | 405 (±326) | N/A | 100% | N/A | 86% | N/A | 0/7 (0%) |
| H4H7798N | 0 (0) | 0 (0) | 19 (±51) | 13 (±35) | 100% | 100% | 100% | 100% | 6/7 (86%) | 6/7 (86%) |
| H4H9008P | 41 (±68) | 7 (±20) | 87 (±123) | 16 (±42) | 100% | 100% | 100% | 100% | 4/7 (57%) | 6/7 (86%) |

of which is provided elsewhere herein). The anti-PD-L1 antibody used in this experiment was an anti-PD-L1 monoclonal antibody with $V_H/V_L$ sequences of antibody "YW243.55S70" according to US20100203056A1 (Genentech, Inc.), with mouse IgG2a and which was cross-reactive with mouse PD-L1.

For this experimental model, $1.0\times10^6$ Colon-26 tumor cells were implanted sub-cutaneously into BALB/c mice at Day 0. Starting on Day 3, prior to the establishment of measurable tumors, mice were treated with one of the mono- or combination therapies, or control combination, as set forth in Table 28.

TABLE 28

Experimental dosing and treatment groups

| Treatment Group | First Agent | Second Agent |
|---|---|---|
| Control Combination | IgG2a isotype control (250 μg, IP) | hFc control (250 μg, SC) |
| VEGF Trap only | IgG2a isotype control (250 μg, IP) | Aflibercept (10 mg/kg, SC) |
| anti-PD-1 only | anti-PD-1 mAb RPMI-14 (250 μg, IP) | hFc control (250 μg, SC) |
| anti-PD-L1 only | anti-PD-L1 mAb (250 μg, IP) | hFc control (250 μg, SC) |
| VEGF Trap + anti-PD-1 | anti-PD-1 mAb RPMI-14 (250 μg, IP) | Aflibercept (10 mg/kg, SC) |
| VEGF Trap + anti-PD-L1 | anti-PD-L1 mAb (250 μg, IP) | Aflibercept (10 mg/kg, SC) |

The various therapies were administered at five different time points over a two week period (i.e., injections at Day 3, Day 6, Day 10, Day 13 and Day 19).

Animals in each therapy group were evaluated in terms of tumor incidence, tumor volume, median survival time, and number of tumor-free animals at Day 50. The extent of tumor growth is summarized in FIG. 2 (tumor growth curves) and FIG. 3 (tumor volume at Day 28). Results are also summarized in Table 29.

TABLE 29

Tumor-free mice in treatment groups

| Treatment Group | No. of Tumor-Free Animals by Day 50 |
|---|---|
| Control Combination | 0/10 |
| VEGF Trap only | 3/10 |
| anti-PD-1 only | 4/10 |
| anti-PD-L1 only | 5/10 |
| VEGF Trap + anti-PD-1 | 7/10 |
| VEGF Trap + anti-PD-L1 | 9/10 |

Figure 3:
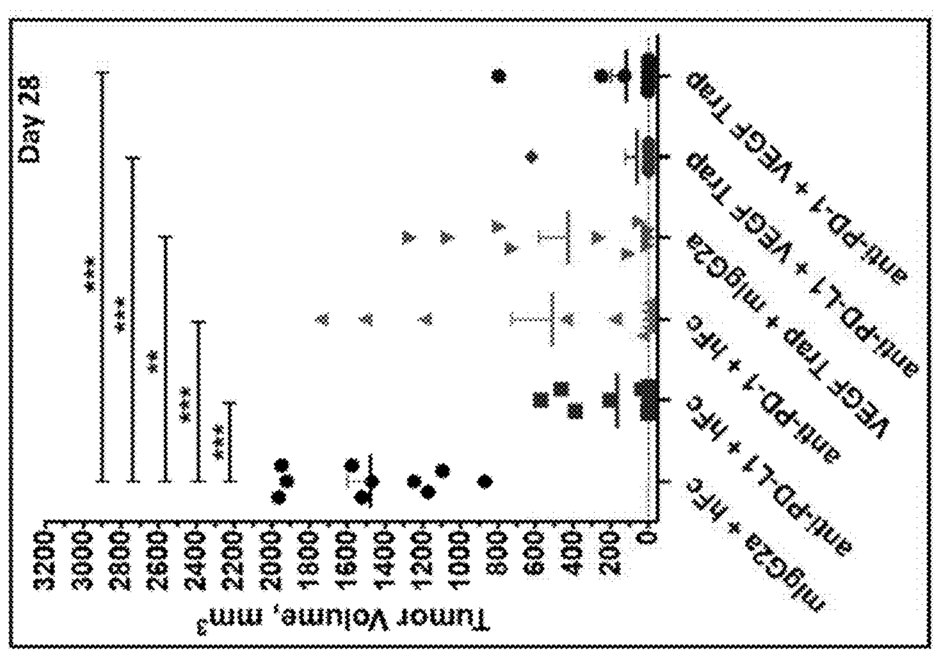
FIG. 3 illustrates tumor growth and survival results for mice implanted with Colon-26 tumor cells at Day 0 and treated with the indicated combinations of molecules by injection at Days 3, 6, 10, 13 and 19 ("early-treatment tumor model"). The graph shows the tumor volume (in $mm^3$) of individual mice in each experimental group at Day 28 after implantation. "mIgG2a" is IgG2 isotype control; "Fc" is human Fc control; "VEGF Trap" is aflibercept; "anti-PD-1" is anti-mouse PD-1 clone RPMI-14; "anti-PD-L1" is an anti-PD-L1 monoclonal antibody as described elsewhere herein.

Tumor growth was substantially reduced in animals treated with the combination of VEGF Trap+anti-PD-1 antibody as compared with treatment regimens involving either therapeutic agent alone (see FIGS. 2 and 3). Furthermore, survival was substantially increased in the VEGF Trap+anti-PD-1 antibody group, with 70% of animals surviving to at least day 50 after tumor implantation. By contrast, for the anti-PD-1 and VEGF Trap monotherapy groups, survival to Day 50 was only 40% and 30% respectively (see FIG. 3 and Table 29).

Example 11

Clinical Trial Study of Repeat Dosing with Anti-PD-1 Antibody as Single Therapy and in Combination with Other Anti-Cancer Therapies in Patients with Advanced Malignancies This is a dose-escalation study of anti-PD-1 antibody, alone or in combination with radiation therapy, cyclophosphamide, or both in patients with advanced malignancies. The exemplary anti-PD-1 antibody ("mAb") used in this Example comprises HCVR of SEQ ID NO: 162 and LCVR of SEQ ID NO: 170.

Study Objectives

The primary objective of the study is to characterize the safety, tolerability, DLTs of mAb administered IV as monotherapy, or in combination with targeted radiation (with the intent to have this serve as an immuno-stimulatory, rather than primarily tumor-ablative therapy), low-dose cyclophosphamide (a therapy shown to inhibit regulatory T-cell responses), or both in patients with advanced malignancies.

The secondary objectives of the study are: (1) to determine a recommended phase 2 dose (RP2D) of mAb as monotherapy and in combination with other anti-cancer therapies (targeted radiation, low-dose cyclophosphamide, or both); (2) to describe preliminary antitumor activity of mAb, alone and with each combination partner (s); (3) to characterize the PK of mAb as monotherapy and in combination with other anti-cancer therapies (targeted radiation, low-dose cyclophosphamide, or both); and (4) to assess immunogenicity of mAb.

Study Design

Safety will be assessed in separate, standard 3+3 dose escalation cohorts (in monotherapy, combination with radiation therapy, combination with cyclophosphamide, and combination with radiation therapy plus cyclophosphamide). The choice of combination therapy with radiation, cyclophosphamide, or both will be based on investigator assessment of the best choice of therapy for an individual patient in consultation with the sponsor. To be enrolled in a radiotherapy cohort, a patient must have a lesion that can be safely irradiated and for which radiation at the limited, palliative doses contemplated would be considered medically appropriate, and at least one other lesion suitable for response evaluation. A patient will be allowed to enroll only if a slot is available in the cohort for the chosen treatment.

Patients will undergo screening procedures to determine eligibility within 28 days prior to the initial administration of mAb. Following enrollment of patients into a mAb monotherapy cohort, enrollment of subsequent cohorts will be determined by occurrence of DLTs in prior cohorts (i.e., no DLT in a cohort of 3 patients, or no more than 1 DLT in an expanded cohort of 6 patients), and the availability of patient slots. The planned monotherapy dose levels are 1, 3, or 10 mg/kg administered IV every 14 days (2 weeks).

Once one or both of the 1 mg/kg or 3 mg/kg mAb monotherapy cohort DLT observation periods are completed without a DLT in a cohort of 3 patients or with no more than 1 DLT in an expanded cohort of 6 patients, patients can be enrolled into a cohort combining cyclophosphamide or radiotherapy with mAb at that monotherapy dose level. Patients can be enrolled into a combination mAb+cyclophosphamide/radiotherapy cohort once the DLT observation periods for both the cohort for that mAb dose level+ cyclophosphamide and the cohort for that mAb dose level+ the same radiotherapy regimen are completed with no DLT in a cohort of 3 patients, or no more than 1 DLT in an expanded cohort of 6 patients.

Once the 3 mg/kg mAb monotherapy cohort DLT observation period is completed with no DLT in a cohort of 3 patients, or no more than 1 DLT in an expanded cohort of 6 patients, a 10 mg/kg mAb monotherapy cohort may also enroll.

mAb 3 mg/kg and 10 mg/kg monotherapy cohorts will enroll only after the requisite number of patients in the prior monotherapy dose cohort (i.e., 1 mg/kg and 3 mg/kg, respectively) have cleared the 28 day DLT observation period without a maximum tolerated dose (MTD) being demonstrated for that dose level. A mAb 1 mg/kg combination treatment cohort will enroll only after completion of the DLT observation period for the 1 mg/kg monotherapy cohort. Combination cohorts receiving 3 mg/kg mAb will enroll only when the requisite number of patients in the respective 1 mg/kg mAb combination cohorts has cleared the DLT observation period without demonstrating a MTD. Triple combination cohorts combining mAb with cyclophosphamide and a radiation regimen will enroll only when the requisite number of patients in both corresponding double combination cohorts at that dosage level have cleared the DLT observation period without a MTD being demonstrated.

Table 30 summarizes the dose-escalation cohorts in which patients will be enrolled.

TABLE 30

Possible Dose-escalation Cohorts

| n | Possible Assigned Treatment Cohort |
|---|---|
| 3-6 | 0.3 mg/kg mAb monotherapy (to be enrolled only if MTD <1 mg/kg mAb) |
| 3-6 | 1 mg/kg mAb monotherapy |
| 3-6 | 3 mg/kg mAb monotherapy[a)] |
| 3-6 | 10 mg/kg mAb monotherapy[b)] |
| 3-6 | 1 mg/kg[a)] mAb + radiotherapy (6 Gy × 5) |
| 3-6 | 1 mg/kg[a)] mAb + radiotherapy (9 Gy × 3) |
| 3-6 | 3 mg/kg[b)] (or MTD) mAb + cyclophosphamide |
| 3-6 | 3 mg/kg[b)] (or MTD) mAb + radiotherapy (6 Gy × 5) |
| 3-6 | 3 mg/kg[b)] (or MTD) mAb + radiotherapy (9 Gy × 3) |
| 3-6 | 3 mg/kg[b)] (or MTD) mAb + radiotherapy (6 Gy × 5) + cyclophosphamide |
| 3-6 | 3 mg/kg[b)] (or MTD) mAb + radiotherapy (9 Gy × 3) + cyclophosphamide |

A DLT is defined as any of the following: a non-hematologic toxicity (e.g., uveitis, or any other irAE), or a hematologic toxicity (e.g., neutropenia, thrombocytopenia, febrile neutropenia).

The maximum tolerated dose (MTD) is defined as the highest dose at which fewer than a third of an expanded cohort of 6 patients experience a DLT during the first cycle of treatment. Thus, the MTD is defined as the dose level immediately below the level at which dosing is stopped due to the occurrence of 2 or more DLTs in an expanded cohort of 6 patients. If dose escalation is not stopped due to the occurrence of DLTs, it will be considered that the MTD has not been determined. It is possible that an MTD may not be defined in this study, either for a monotherapy group or for individual combination groups. Additionally, it is possible that mAb MTDs may differ between monotherapy and each combination treatment regimen.

Study Duration

Patients will receive up to 48 weeks of treatment, after which there will be a 24 week follow-up period. A patient will receive treatment until the 48 week treatment period is complete, or until disease progression, unacceptable toxicity, withdrawal of consent, or meeting of another study withdrawal criterion. After a minimum of 24 weeks of treatment, patients with confirmed complete responses (CR) may elect to discontinue treatment and continue with all relevant study assessments (e.g., efficacy assessments). After a minimum of 24 weeks of treatment, patients with tumor burden assessments of stable disease (SD) or partial response (PR) that have been unchanged for 3 successive tumor evaluations may also elect to discontinue treatment and continue with all relevant study assessments (e.g., efficacy assessments).

Study Population

The target population for this study comprises patients with advanced malignancies who are not candidates for standard therapy, unwilling to undergo standard therapy, or for whom no available therapy is expected to convey clinical benefit; and patients with malignancies that are incurable and have failed to respond to or showed tumor progression despite standard therapy.

Inclusion criteria: A patient must meet with the following criteria to be eligible for inclusion in the study: (1) demonstrated progression of a solid tumor with no alternative standard-of-care therapeutic option available; (2) at least 1 lesion for response assessment. Patients assigned to radiotherapy require at least one additional lesion that can be safely irradiated while sparing the index lesions and for which radiation at the limited, palliative doses contemplated would be considered medically appropriate; (3) Eastern Cooperative Oncology Group (ECOG) performance status ≤1; (4) more than 18 years old; (5) hepatic function: a. total bilirubin ≤1.5× upper limit of normal (ULN; if liver metastases ≤3× ULN), b. transaminases ≤3× ULN (or ≤5.0× ULN, if liver metastases), c. alkaline phosphatase (ALP) ≤2.5× ULN (or 5.0× ULN, if liver metastases); (6) renal function: serum creatinine ≤1.5× ULN; (7) neutrophil count (ANC) ≥1.5×$10^9$/L, c. platelet count ≥75×$10^9$/L; (8) ability to provide signed informed consent; and (9) ability and willingness to comply with scheduled visits, treatment plans, laboratory tests, and other study-related procedures.

Exclusion criteria: A patient who meets any of the following criteria will be excluded from the study: (1) Ongoing or recent (within 5 years) evidence of significant autoimmune disease that required treatment with systemic immunosuppressive treatments, which may suggest risk for irAEs; (2) Prior treatment with an agent that blocks the PD-1/PD-L1 pathway; (3) Prior treatment with other immune modulating agents within fewer than 4 weeks or 4 half-lives, whichever is greater, prior to the first dose of mAb; (4) Examples of immune modulating agents include blockers of CTLA-4, 4-1BB (CD137), OX-40, therapeutic vaccines, or cytokine treatments; (5) Untreated brain metastasis(es) that may be considered active. Patients with previously treated brain metastases may participate provided they are stable (i.e., without evidence of progression by imaging for at least 4 weeks prior to the first dose of study treatment, and any neurologic symptoms have returned to baseline), and there is no evidence of new or enlarging brain metastases; (6) Immunosuppressive corticosteroid doses (>10 mg prednisone daily or equivalent) within 4 weeks prior to the first dose of mAb; (7) Deep vein thrombosis, pulmonary embolism (including asymptomatic pulmonary embolism identified on imaging), or other thromboembolic event within the 6 months preceding the first dose of mAb; (8) Active infection requiring therapy, including known infection with human immunodeficiency virus, or active infection with hepatitis B or hepatitis C virus; (9) History of pneumonitis within the last 5 years; (10) Any investigational or antitumor treatment within 30 days prior to the initial administration of mAb; (11) History of documented allergic reactions or acute hypersensitivity reaction attributed to treatment with antibody therapies in general, or to agents specifically used in the study; (12) Known allergy to doxycycline or tetracycline (precaution due to presence of trace components in mAb); (13) Breast-feeding; (14) Positive serum pregnancy test; (15) History within the last 5 years of an invasive malignancy other than the one treated in this study, with the exception of resected/ablated basal or squamous-cell carcinoma of the skin or carcinoma in situ of the cervix, or other local tumors considered cured by local treatment; (16) Acute or chronic psychiatric problems that, under the evaluation of the investigator, make the patient ineligible for participation; and (17) Continued sexual activity in men or women of childbearing potential who are unwilling to practice adequate contraception during the study.

Study Treatments mAb will be supplied as a liquid in sterile, single-use vials. Each vial will contain a volume sufficient to withdraw 10 mL of mAb at a concentration of 25 mg/mL. Instructions on dose preparation are provided in the study reference manuals. mAb will be administered in an outpatient setting as a 30 minute IV infusion. Each patient's dose will depend on individual body weight. The dose of mAb must be adjusted each cycle for changes in body weight of 0%. mAb will be administered alone and in combination with radiation and or cyclophosphamide.

Monotherapy mAb will be administered in an outpatient setting by IV infusion over 30 minutes every 14 days for 48 weeks (i.e., Days 1, 15±3, 29±3, and 43±3 of a 56 day cycle). Planned monotherapy regimens to be assigned may include: (i) 1 mg/kg IV infusion over 30 minutes every 14 days for 48 weeks; (ii) 3 mg/kg infusion over 30 minutes every 14 days for 48 weeks; (iii) 10 mg/kg infusion over 30 minutes every 14 days for 48 weeks; and (iv) 0.3 mg/kg infusion over 30 minutes every 14 days for 48 weeks (if MTD is determined to be below 1 mg/kg).

Combination Therapy

Concomitant radiation therapy and cyclophosphamide will be supplied through a prescription and their usage, dose, dose modifications, reductions, or delays, as well as any potential AEs resulting from their use, will be tracked along with that of mAb.

Co-administration of mAb and radiation: mAb will be administered by IV infusion over 30 minutes every 14 days for 48 weeks in combination with radiation treatment from day 8 to day 12. Planned combination mAb and radiation therapy regimens may include:

- 1 mg/kg mAb infusion over 30 minutes every 14 days for 48 weeks plus 30 Gy radiotherapy (6 Gy×5 times/week; given 1 week after the first dose of mAb, preferably on consecutive days)
- 1 mg/kg mAb infusion over 30 minutes every 14 days for 48 weeks plus 27 Gy radiotherapy (9 Gy×3 times/week; given 1 week after the first dose of mAb, preferably not on consecutive days)
- 3 mg/kg mAb infusion over 30 minutes every 14 days for 48 weeks plus 30 Gy radiotherapy (6 Gy×5 times/week; given 1 week after the first dose of mAb, preferably on consecutive days)
- 3 mg/kg mAb infusion over 30 minutes every 14 days for 48 weeks plus 27 Gy radiotherapy (9 Gy×3 times/week; given 1 week after the first dose of mAb, preferably not on consecutive days)

Patients will receive either 30 Gy given as 5 fractions of 6 Gy administered daily starting 1 week after the first dose of mAb, or 27 Gy given as 3 fractions of 9 Gy administered every other day starting 1 week after the first dose of mAb. The lesion selected for radiation should be a lesion that can be safely irradiated with focal irradiation while sparing the index lesion(s), and for which radiation at the limited, palliative doses contemplated would be considered medically appropriate. The target dose for a patient will be based on cohort assignment and should conform to the normal tissue requirements, in accord with standard radiation oncology practice. Treatment at the protocol-specified dosing regimen is permitted only if the normal tissue criteria are met. If the normal tissue criteria cannot be met at either of the radiation therapy regiments specified in the protocol, the patient is not eligible for enrollment in a combination radiation treatment cohort in this study.

Co-administration of mAb and cyclophosphamide: mAb will be administered by IV infusion over 30 minutes every 14 days (2 weeks) for 48 weeks in combination with cyclophosphamide 200 mg/m$^2$ every 14 days for 4 doses. Each of the 4 cyclophosphamide doses will be administered 1 day before each of the first 4 mAb doses (days −1, 14, 28, and 42 of the first 56 day cycle).

Though cyclophosphamide has been used successfully concurrently with other drugs, the rate of metabolism and the leukopenic activity of cyclophosphamide reportedly are increased by chronic administration of high doses of phenobarbital. Cyclophosphamide treatment causes a marked and persistent inhibition of cholinesterase activity, thus potentiating the effect of succinylcholine chloride. The planned combination mAb and cyclophosphamide regimen to be assigned is:

- Cyclophosphamide 200 mg/m$^2$ every 14 days (days −1, 14, 28, and 42 of the first 56 day cycle) for a total of 4 doses plus
- 3 mg/kg mAb infusion over 30 minutes every 14 days for 48 weeks (provided monotherapy dose of 3 mg/kg<MTD; if 3 mg/kg>MTD, dose will be 1 mg/kg).

Co-administration of mAb, radiation and cyclophosphamide: The planned combination mAb, radiation, and cyclophosphamide regimen includes:

- Cyclophosphamide 200 mg/m$^2$ every 14 days (days −1, 14, 28, and 42 of the first 56 day cycle) for a total of 4 doses plus
- 27 Gy radiotherapy (9 Gy×3 times/week; given 1 week after the first dose of mAb, preferably not on consecutive days) OR
  - 30 Gy radiotherapy (6 Gy×5 times/week; given 1 week after the first dose of mAb, preferably on consecutive days) plus
- 3 mg/kg mAb infusion over 30 minutes every 14 days for 48 weeks (provided monotherapy dose of 3 mg/kg<MTD; if 3 mg/kg>MTD, dose will be 1 mg/kg)

Study Variables

Primary Variables: Primary safety variables include incidence of DLTs, incidence and severity of treatment-emergent adverse events (TEAEs), and abnormal laboratory findings through 48 weeks of treatment.

Secondary Variables: Key secondary variables include the following:

- Serum concentration and pharmacokinetics (PK) of mAb
- Antitumor activities assessed using the appropriate criteria for the indication:
  - Response Evaluation Criteria in Solid Tumors (RECIST) criteria measured by computed tomography (CT) or magnetic resonance imaging (MRI)

Other assessment criteria should also be used for specific tumors in which RECIST measurements are not the standard.

Immune-Related Response Criteria (irRC) applied to RECIST measurements.

In all cases, irRC will be the governing tool to determine progression of disease (PD), SD, CR, or PR. Standard RECIST data will also be collected for information purposes.

Anti-mAb antibodies

Study Procedures

The following procedures will be performed at screening for the purpose of determining study eligibility or characterizing the baseline population: (i) serum β-HCG (result must be ≤72 hours before first dose); (ii) Collection of archived tumor material: After a patient has given informed consent, the patient will be asked to arrange to provide any available previously collected tumor samples; (iii) Brain MRI: Brain MRI is required at screening if not performed in the prior 60 days; and (iv) Chest x-ray: Chest is x-ray required at screening if not performed in the prior 60 days.

Efficacy Procedures: A CT or MRI for tumor assessment will be performed at the screening visit (within 28 days prior to infusion) and during every cycle (approximately every 8 weeks) on day 56±3, and when disease progression is suspected. Additionally, for patients who have not progressed on study, tumor assessment will be performed for follow-up visits 3, 5, and 7. Once the choice has been made to use CT scan or MRI, subsequent assessments will be made using the same modality.

Tumor response evaluation will be performed according to immune-related response criteria (irRC; Nishino 2013). Assessments according to Response Evaluation Criteria in Solid Tumors (RECIST) version 1.1 (Eisenhauer 2009) will also be performed as a supportive exploration; however, the primary determination of disease progression for an individual patient will be made according to irRC. Measurable lesions selected as target lesions for RECIST assessments will also be included as index lesions for irRC assessments.

Safety Procedures: Vital signs, including temperature, resting blood pressure, pulse, and respiration, will be collected. When scheduled at the same visit as other procedures, vital signs should be measured prior to clinical laboratory assessments, PK, or exploratory sample collection. During cycle 1, vital signs will be recorded on treatment days prior to treatment, at the end of the infusion, every 30 minutes for the first 4 hours post-infusion, and at 6 and 8 hours post study drug administration. On subsequent cycles, vital signs on treatment days will be assessed and documented prior to the infusion, every 30 minutes for the first 2 hours, and then hourly until 4 hours following study drug administration.

A thorough complete or limited physical examination will be performed at visits. Complete physical examination will include examination of skin, head, eyes, nose, throat, neck, joints, lungs, heart, pulse, abdomen (including liver and spleen), lymph nodes, and extremities, as well as a brief neurologic examination. Limited physical examination will include lungs, heart, abdomen, and skin.

A standard 12-lead ECG will be performed. Any ECG finding that is judged by the investigator as a clinically significant change (worsening) compared to the baseline value will be considered an AE, recorded, and monitored.

Immune safety assays consist of rheumatoid factor (RF), thyroid stimulating hormone (TSH), C-reactive protein (CRP), and antinuclear antibody (ANA) titer and pattern. If, during the course of the study, a 4-fold or greater increase from baseline in RF or ANA or abnormal levels of TSH or CRP are observed, the following tests may also be performed: anti-DNA antibody, anti-Sjögren's syndrome A antigen (SSA) antibody (Ro), anti-Sjögren's syndrome B antigen (SSB) antibody (La), antithyroglobulin antibody, anti-LKM antibody, antiphospholipid antibody, anti-islet cell antibody, antineutrophil cytoplasm antibody, C3, C4, CH50. Activated partial thromboplastin time (aPTT) and International Normalized Ratio (INR) will be analyzed by the site's local laboratory.

Safety

An adverse event (AE) is any untoward medical occurrence in a patient administered a study drug which may or may not have a causal relationship with the study drug. Therefore, an AE is any unfavorable and unintended sign (including abnormal laboratory finding), symptom, or disease which is temporally associated with the use of a study drug, whether or not considered related to the study drug. An AE also includes any worsening (i.e., any clinically significant change in frequency and/or intensity) of a pre-existing condition that is temporally associated with the use of the study drug. Progression of underlying malignancy will not be considered an AE if it is clearly consistent with the typical progression pattern of the underlying cancer (including time course, affected organs, etc.). Clinical symptoms of progression may be reported as AEs if the symptom cannot be determined as exclusively due to the progression of the underlying malignancy, or does not fit the expected pattern of progression for the disease under study.

An serious adverse event (SAE) is any untoward medical occurrence that at any dose results in death, is life-threatening, requires in-patient hospitalization or prolongation of existing hospitalization, results in persistent or significant disability/incapacity (substantial disruption of one's ability to conduct normal life functions), is a congenital anomaly/birth defect.

Patient information on all AEs and SAEs will be recorded.

Statistical Plan

The study dose escalation is based on a traditional 3+3 design with 3 to 6 patients assigned per dose level. The exact number of patients enrolled in the study will depend on the number of protocol-defined DLTs observed, and the need to expand currently defined dose levels, or open additional cohorts at lower dose levels. After the required initial enrollment to the next cohort in the dose escalation has occurred, enrollment to each of the previous cohorts below the MTD for that treatment will be expanded (if not previously expanded during escalation) to a total of 6 patients.

Data will be summarized using descriptive statistics only. In general, data will be summarized by dose levels and combinations. The safety summaries and analyses will be performed on the safety analysis set (SAF). The primary analysis of safety will be based on treatment-emergent AEs (TEAEs).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. An isolated nucleic acid molecule comprising a nucleic acid sequence encoding a heavy chain variable domain region (HCVR) of an antibody that binds programmed death 1 (PD-1), wherein the HCVR comprises a heavy chain CDR1 (HCDR1) encoded by the nucleotide sequence of SEQ ID NO: 163, a heavy chain CDR2 (HCDR2) encoded by the nucleotide sequence of SEQ ID NO: 165, and a heavy chain CDR3 (HCDR3) encoded by the nucleotide sequence of SEQ ID NO: 167.

2. The nucleic acid molecule of claim 1, wherein the HCDR1 comprises the amino acid sequence of SEQ ID NO: 164, the HCDR2 comprises the amino acid sequence of SEQ ID NO: 166, and the HCDR3 comprises the amino acid sequence of SEQ ID NO: 168.

3. The nucleic acid molecule of claim 1, wherein the HCVR comprises the amino acid sequence of SEQ ID NO: 162.

4. The nucleic acid molecule of claim 1, wherein the nucleic acid molecule comprises the nucleotide sequence of SEQ ID NO: 161 or a substantially identical sequence having at least 95% homology thereof.

5. The nucleic acid molecule of claim 1, wherein the nucleic acid molecule comprises the nucleotide sequence of SEQ ID NO: 161.

6. An isolated nucleic acid molecule comprising a nucleic acid sequence encoding a light chain variable region (LCVR) of an antibody that binds programmed death 1 (PD-1), wherein the LCVR comprises a light chain CDR1 (LCDR1) encoded by the nucleotide sequence of SEQ ID NO: 171, a light chain CDR2 (LCDR2) encoded by the nucleotide sequence of SEQ ID NO: 173, and a light chain CDR3 (LCDR3) encoded by the nucleotide sequence of SEQ ID NO: 175.

7. The nucleic acid molecule of claim 6, wherein the LDCR1 comprises the amino acid sequence of SEQ ID NO: 172, the LCDR2 comprises the amino acid sequence of SEQ ID NO: 174, and the LCDR3 comprises the amino acid sequence of SEQ ID NO: 176.

8. The nucleic acid molecule of claim 6, wherein the LCVR comprises SEQ ID NO: 170.

9. The nucleic acid molecule of claim 6, wherein the nucleic acid molecule comprises the nucleotide sequence of SEQ ID NO: 169 or a substantially identical sequence having at least 95% homology thereof.

10. The nucleic acid molecule of claim 6, wherein the nucleic acid molecule comprises the nucleotide sequence of SEQ ID NO: 169.

11. An expression vector comprising:

(a) a nucleic acid molecule comprising a nucleic acid sequence encoding a heavy chain variable domain region (HCVR) of an antibody that binds programmed death 1 (PD-1), wherein the HCVR comprises a heavy chain CDR1 (HCDR1) encoded by the nucleotide sequence of SEQ ID NO: 163, a heavy chain CDR2 (HCDR2) encoded by the nucleotide sequence of SEQ ID NO: 165, and a heavy chain CDR3 (HCDR3) encoded by the nucleotide sequence of SEQ ID NO: 167; and/or (b) a nucleic acid molecule comprising a nucleic acid sequence encoding a light chain variable region (LCVR) of an antibody that binds PD-1, wherein the LCVR comprises a light chain CDR1 (LCDR1) encoded by the nucleotide sequence of SEQ ID NO: 171, a light chain CDR2 (LCDR2) encoded by the nucleotide sequence of SEQ ID NO: 173, and a light chain CDR3 (LCDR3) encoded by the nucleotide sequence of SEQ ID NO: 175.

12. An isolated host cell comprising the expression vector of claim 11.

13. The host cell of claim 12, wherein the host cell is a mammalian cell or a prokaryotic cell.

14. The host cell of claim 12, wherein the host cell is a Chinese Hamster Ovary (CHO) cell or an *Escherichia coli* (*E. coli*) cell.

15. A method of producing an anti-PD-1 antibody or antigen-binding fragment thereof, the method comprising growing the host cell of claim 12 under conditions permitting production of the antibody or antigen-binding fragment thereof, wherein said host cell comprises both a nucleic acid molecule comprising a nucleic acid sequence encoding said HCVR and a nucleic acid molecule comprising a nucleic acid sequence encoding said LCVR.

16. The method of claim 15, further comprising formulating the antibody or antigen-binding fragment thereof as a pharmaceutical composition comprising an acceptable carrier.

17. A composition comprising a first nucleic acid molecule and a second nucleic acid molecule;

wherein the first nucleic acid molecule comprises a nucleic acid sequence encoding a heavy chain variable domain region (HCVR) of an antibody that binds programmed death 1 (PD-1), wherein the HCVR comprises a heavy chain CDR1 (HCDR1) encoded by the nucleotide sequence of SEQ ID NO: 163, a heavy chain CDR2 (HCDR2) encoded by the nucleotide sequence of SEQ ID NO: 165, and a heavy chain CDR3 (HCDR3) encoded by the nucleotide sequence of SEQ ID NO: 167; and wherein the second nucleic acid molecule comprises a nucleic acid sequence encoding a light chain variable region (LCVR) of an antibody that binds PD-1, wherein the LCVR comprises a light chain CDR1 (LCDR1) encoded by the nucleotide sequence of SEQ ID NO: 171, a light chain CDR2 (LCDR2) encoded by the nucleotide sequence of SEQ ID NO: 173, and a light chain CDR3 (LCDR3) encoded by the nucleotide sequence of SEQ ID NO: 175.

18. The composition of claim 17, wherein the HCVR comprises SEQ ID NO: 162, and wherein the LCVR comprises SEQ ID NO: 170.

* * * * *